US012773425B1

(12) United States Patent
Rodriguez et al.

(10) Patent No.: US 12,773,425 B1
(45) Date of Patent: Oct. 27, 2026

(54) DIETARY COMPOSITION FOR DAIRY COWS WITH ALUMINUM SUPPLEMENTATION AND CONTROLLED DCAD

(71) Applicant: Innovative Liquids, LLC, Austin, TX (US)

(72) Inventors: Luis Alberto Rodriguez, Austin, TX (US); Joseph M Harris, Rockford, AL (US); Kristen Rose Gallagher-Dmitriiev, Hayward, CA (US); Paul Curtis Mostyn, Magnolia, TX (US)

(73) Assignee: Innovative Liquids, LLC, Austin, TX (US)

( * ) Notice: Subject to any disclaimer, the term of this patent is extended or adjusted under 35 U.S.C. 154(b) by 0 days.

(21) Appl. No.: 19/576,327

(22) Filed: Mar. 24, 2026

Related U.S. Application Data

(60) Provisional application No. 63/872,300, filed on Aug. 28, 2025, provisional application No. 63/894,602, filed on Oct. 6, 2025.

(51) Int. Cl.
*A23K 20/24* (2016.01)
*A23K 20/20* (2016.01)
(Continued)

(52) U.S. Cl.
CPC .............. *A61K 33/10* (2013.01); *A23K 20/24* (2016.05); *A23K 20/26* (2016.05); *A23K 20/30* (2016.05);
(Continued)

(58) Field of Classification Search
CPC ...... A61K 33/10; A61K 9/0056; A61K 33/08; A23K 20/24; A23K 20/26; A23K 20/30; A23K 50/10
See application file for complete search history.

(56) References Cited

U.S. PATENT DOCUMENTS 12,150,954 B1 11/2024 Jakobsen et al.
12,310,984 B1 5/2025 Jakobsen et al.

OTHER PUBLICATIONS

Alber, Jana; Föller, Michael. "Lactic acid induces fibroblast growth factor 23 (FGF23) production in UMR106 osteoblast-like cells." Molecular and Cellular Biochemistry, vol. 477, No. 1-2, 2022, pp. 363-370. Springer, Stuttgart, Germany. Published online Nov. 3, 2021.

(Continued)

*Primary Examiner* — Ernst V Arnold

(57) ABSTRACT

A total dietary composition (TDC) for dairy cows comprises a basal diet and a dietary supplement containing phosphorus-binding elements, including chemical sources of aluminum(III) and/or iron(III). The supplement is formulated to bind phosphorus, contributing to a TDC with a phosphorus-to-aluminum weight ratio of 1.5:1 to 2.5:1 or a phosphorus-to-(aluminum times calcium) ratio of 1.8:1 to 4.0:1, measured on a dry matter basis. The TDC maintains a Dietary Cation-Anion Difference (DCAD) of −15 to +10 mEq/100 g dry matter, calculated as ([Na]+[K])—[Cl]+[S]). Optional ingredients include non-protein nitrogen, molasses, clay, and water. When fed to prepartum dairy cows, the TDC maintains serum phosphorus levels, reduces hypocalcemia, and supports metabolic health, enhancing dietary efficiency, milk yield, and animal well-being.

20 Claims, 42 Drawing Sheets

(51) Int. Cl.
*A23K 20/26* (2016.01)
*A23K 50/10* (2016.01)
*A61K 9/00* (2006.01)
*A61K 33/08* (2006.01)
*A61K 33/10* (2006.01)
*A23K 20/28* (2016.01)

(52) U.S. Cl.
CPC ........... *A23K 50/10* (2016.05); *A61K 9/0056* (2013.01); *A61K 33/08* (2013.01)

(56) References Cited

OTHER PUBLICATIONS

Allen, V. G. "Influence of Dietary Aluminum on Nutrient Utilization in Ruminants." Journal of Animal Science, 1984, vol. 59, No. 3, pp. 836-842. American Society of Animal Science, Champaign, Illinois, USA.

Alshehhi, S. A., T. Mohammed, A. Zewude, B. Bayissa, A. Antony, B. A. Degafa, and G. Ameni. "Retrospective Study on the Cumulative Incidence of Milk Fever in Parturient Cows: A Case Study in the United Arab Emirates." BMC Veterinary Research, 2024, vol. 20, No. 587, pp. 1-9. BMC (Springer Nature), London, United Kingdom.

Ametaj, Burim N. "From Parts to Whole: A Systems Biology Approach to Decoding Milk Fever." Veterinary Sciences, vol. 12, No. 4, 2025, pp. 347 et. seq. (25 pages total). MDPI, Basel, Switzerland. Published Apr. 9, 2025.

Bradford, B. J.; Yuan, K.; Farney, J. K.; Mamedova, L. K.; Carpenter, A. J. "Invited Review: Inflammation During the Transition to Lactation: New Adventures with an Old Flame." Journal of Dairy Science, 2015, vol. 98, No. 10, pp. 6631-6650. American Dairy Science Association®, Champaign, Illinois, USA.

Cook, J. G.; Pepler, P. T.; Viora, L.; Hill, D. L. "Assessing transition cow management in dairy cows for improved health, milk production, pregnancy, and culling outcomes." Journal of Dairy Science, 2024, vol. 107, pp. 11381-11397. Published by Elsevier Inc. on behalf of the American Dairy Science Association, United States.

Crowe, N. A.; Neathery, M. W.; Miller, W. J.; Muse, L. A.; Crowe, C. T.; Varnadoe, J. L.; Blackmon, D. M. "Influence of High Dietary Aluminum on Performance and Phosphorus Bioavailability in Dairy Calves." Journal of Dairy Science, 1990, vol. 73, No. 3, pp. 808-818. American Dairy Science Association, Champaign, Illinois, USA.

Dishington, Inger W. "Prevention of Milk Fever (Hypocalcemic Paresis Puerperalis) by Dietary Salt Supplements." Acta Veterinaria Scandinavica, 1975, vol. 16, pp. 503-512. Veterinary College of Norway, Oslo, Norway.

Eisenberg, S. W. F.; Ravesloot, L.; Koets, A. P.; Grünberg, W. "Effect of dietary phosphorus deprivation on leukocyte function in transition cows." Journal of Dairy Science, 2019, vol. 102, No. 2, pp. 1559-1570. American Dairy Science Association, Champaign, Illinois, USA.

Frizzarini, Waneska S.; Campolina, Joana; Vang, Alysia; Monteiro, Pedro; and Hernandez, Laura L. "Effects of Feeding Synthetic Zeolite A and Negative Dietary Cation-Anion Difference Diets Prepartum on Mineral Metabolism of Multiparous Holstein Cows." Tri-State Dairy Nutrition Conference Proceedings, Apr. 10-12, 2023, pp. 23-31. Tri-State Dairy Nutrition Conference, Madison, Wisconsin, USA.

Frizzarini, W. S.; Monteiro, P. L. J.; Campolina, J. P.; Vang, A. L.; Soudah, O.; Lewandowski, L. R.; Connelly, M. K.; Arriola Apelo, S. I.; Hernandez, L. L. "Mechanisms by Which Feeding Synthetic Zeolite A and Dietary Cation Anion Difference Diets Impact Mineral Metabolism in Multiparous Holstein Cows: Part I." Journal of Dairy Science, 2024, Article in Press (uncorrected proof), since published in vol. 107, No. 7. pp. 5204-5221. American Dairy Science Association / Elsevier Inc., United States.

Goff, J. P.; Liesegang, A.; Horst, R. L. "Diet-induced pseudohypoparathyroidism: A hypocalcemia and milk fever risk factor." Journal of Dairy Science, 2014, vol. 97, No. 3, pp. 1520-1528. American Dairy Science Association, United States.

Grabherr, H.; Spolders, M.; Lebzien, P.; Hüther, L.; Flachowsky, G.; Fürll, M.; Grün, M. "Effect of Zeolite A on Rumen Fermentation and Phosphorus Metabolism in Dairy Cows." Archives of Animal Nutrition, vol. 63, No. 4, Aug. 2009, pp. 321-336. Taylor & Francis, London, United Kingdom.

Hoffman, Patrick C. "Calcium Release Technologies (CaRT): New Innovations to Prevent Hypocalcemia in Dairy Cattle." Western Dairy Management Conference Proceedings, Feb. 28-Mar. 2, 2023, pp. 56-63. Western Dairy Management Conference, Reno, Nevada, USA.

Horst, E. A.; Kvidera, S. K.; Baumgard, L. H. "Invited review: The influence of immune activation on transition cow health and performance—A critical evaluation of traditional dogmas." Journal of Dairy Science, vol. 104, No. 8, 2021, pp. 8380-8410. American Dairy Science Association, published by Elsevier Inc. and Fass Inc., United States.

Huff, W. E.; Moore, P. A., Jr.; Balog, J. M.; Bayyari, G. R.; Rath, N. C. "Evaluation of the Toxicity of Alum (Aluminum Sulfate) in Young Broiler Chickens." Poultry Science, 1996, vol. 75, pp. 1359-1364. Poultry Science Association / Elsevier, United States.

Huyghebaert, G.; De Groote, G.; Keppens, L. "The Relative Biological Availability of Phosphorus in Feed Phosphates for Broilers." Annales de Zootechnie, 1980, pp. 245-263, vol. 29, No. 3. Institut National de la Recherche Agronomique (INRA), Paris, France.

Kerwin, A. L .; Ryan, C. M.; Leno, B. M.; Jakobsen, M.; Theilgaard, P.; Barbano, D. M.; Overton, T. R. "Effects of feeding synthetic zeolite A during the prepartum period on serum mineral concentration, oxidant status, and performance of multiparous Holstein cows." Journal of Dairy Science, Jun. 2019, vol. 102, No. 6, pp. 5191-5207. Published by the American Dairy Science Association, United States.

Kerwin, A. L.; Ryan, C. M.; Leno, B. M.; Jakobsen, M.; Theilgaard, P.; Overton, T. R. "Prepartum Dietary Management of Hypocalcemia Through the Use of a Synthetic Zeolite A." Proceedings of the Cornell Nutrition Conference, 2023, pp. 180-187. Cornell University, Ithaca, New York, USA.

Liang, D., Arnold, L. M., Stowe, C. J., Harmon, R. J., and Bewley, J. M. "Estimating US Dairy Clinical Disease Costs with a Stochastic Simulation Model." Journal of Dairy Science, vol. 100, No. 2, 2017, pp. 1472-1486. American Dairy Science Association, Champaign, Illinois, USA.

Masuda, Yuki; Ohta, Hiroya; Morita, Yumiko; Nakayama, Yoshiaki; Miyake, Ayumi; Itoh, Nobuyuki; and Konishi, Morichika. "Expression of Fgf23 in Activated Dendritic Cells and Macrophages in Response to Immunological Stimuli in Mice." Biological & Pharmaceutical Bulletin, vol. 38, No. 5, The Pharmaceutical Society of Japan, Kobe & Kyoto, Japan, 2015, pp. 687-693.

McArt, J. A. A., and Neves, R. C. "Association of Transient, Persistent, or Delayed Subclinical Hypocalcemia with Early Lactation Disease, Removal, and Milk Yield in Holstein Cows." Journal of Dairy Science, vol. 103, No. 1, American Dairy Science Association, 2020, pp. 690-701, Ithaca, NY & West Lafayette, IN.

Onal, Melda; Carlson, Alex H.; Thostenson, Jeff D.; Benkusky, Nancy A.; Meyer, Mark B.; Lee, Seong M.; Pike, J. Wesley. "A Novel Distal Enhancer Mediates Inflammation-, PTH-, and Early Onset Murine Kidney Disease-Induced Expression of the Mouse Fgf23 Gene." JBMR Plus, vol. 2, No. 1, Jan. 2018, pp. 31-46. Wiley Periodicals, Inc., on behalf of the American Society for Bone and Mineral Research. Published in Madison, WI, USA.

Peterson, A. B.; Orth, M. W.; Goff, J. P.; Beede, D. K. Periparturient Responses of Multiparous Holstein Cows Fed Different Dietary Phosphorus Concentrations Prepartum. Journal of Dairy Science, 2005, vol. 88, No. 10, pp. 3582-3594. American Dairy Science Association, United States.

Robinson, D. L.; Hemkes, O. J.; Kemp, A. "Relationships Among Forage Aluminum Levels, Soil Contamination on Forages, and Availability of Elements to Dairy Cows." Netherlands Journal of Agricultural Science, 1984, vol. 32, pp. 73-80. Centre for Agrobiological Research, Wageningen, Netherlands.

(56) References Cited

OTHER PUBLICATIONS

Rossaint, Jan; Oehmichen, Jessica; Van Aken, Hugo; Reuter, Stefan; Pavenstädt, Hermann J.; Meersch, Melanie; Unruh, Mark; Zarbock, Alexander. "FGF23 Signaling Impairs Neutrophil Recruitment and Host Defense During CKD." The Journal of Clinical Investigation, 2016, vol. 126, No. 3, pp. 962-974. Published by the American Society for Clinical Investigation, USA.

Rossi, A. F.; Miles, R. D.; Harms, R. H. "Influence of Aluminum on Phosphorus Availability in Laying Hen Diets." Poultry Science, 1990, vol. 69, pp. 2237-2240. Poultry Science Association, Champaign, Illinois, USA.

Santos, J. E. P.; Lean, I. J.; Golder, H.; Block, E. "Meta-analysis of the Effects of Prepartum Dietary Cation-Anion Difference on Performance and Health of Dairy Cows." Journal of Dairy Science, 2019, vol. 102, No. 3, pp. 2134-2154. American Dairy Science Association, Champaign, Illinois, USA.

Satter, Larry. "What Goes In Must Come Out—Phosphorus Balance on Dairy Farms." The AABP Proceedings, vol. 35, Sep. 2002, pp. 125-129. American Association of Bovine Practitioners, Madison, Wisconsin, USA.

Serrenho, R. C.; Devries, T. J.; Duffield, T. F.; and Leblanc, S. J. "Graduate Student Literature Review: What Do We Know About the Effects of Clinical and Subclinical Hypocalcemia on Health and Performance of Dairy Cows?" Journal of Dairy Science, vol. 104, No. 5, 2021, pp. 6304-6326. Published by Elsevier Inc. and Fass Inc. on behalf of the American Dairy Science Association, United States.

Sheikh, M. S.; Maguire, J. A.; Emmett, M.; Santa Ana, C. A.; Nicar, M. J.; Schiller, L. R.; Fordtran, J. S. "Reduction of Dietary Phosphorus Absorption by Phosphorus Binders. A Theoretical, In Vitro, and In Vivo Study." The Journal of Clinical Investigation, vol. 83, No. 1, Jan. 1989, pp. 66-73. The American Society for Clinical Investigation, United States.

Singh, Saurav; Grabner, Alexander; Yanucil, Christopher; Schramm, Karla; Czaya, Brian; Krick, Stefanie; Czaja, Mark J.; Bartz, Rene; Abraham, Reimar; Di Marco, Giovana S.; Brand, Marcus; Wolf, Myles; and Faul, Christian. "Fibroblast Growth Factor 23 Directly Targets Hepatocytes to Promote Inflammation in Chronic Kidney Disease." Kidney International, vol. 90, No. 5, 2016, pp. 985-996. Published by Elsevier Inc. for the International Society of Nephrology, USA.

Street, Harold R. "The Influence of Aluminum Sulfate and Aluminum Hydroxide upon the Absorption of Dietary Phosphorus by the Rat." Journal of Nutrition, vol. 24, No. 2, 1942, pp. 111-119. Published by the American Institute of Nutrition, United States.

Thein, O. S.; Ali, N. A.; Mahida, R. Y.; Dancer, R. C. A.; Ostermann, M.; Amrein, K.; Martucci, G.; Scott, A.; Thickett, D. R.; Parekh, D. "Raised FGF23 Correlates to Increased Mortality in Critical Illness, Independent of Vitamin D." Biology (journal), 2023, vol. 12, Issue 2, Article 309, pp. 1-12. Published by MDPI, Basel, Switzerland.

Thilsing-Hansen, T.; Jørgensen, R. J.; Enemark, J. M. D.; Larsen, T. "The Effect of Zeolite A Supplementation in the Dry Period on Periparturient Calcium, Phosphorus, and Magnesium Homeostasis." Journal of Dairy Science, 2002, vol. 85, pp. 1855-1862. Published by the American Dairy Science Association, Champaign, Illinois, USA.

USDA-NAHMS. 2014. Trends in Dairy Cattle Health and Management Practices in the United States, 1991-2014. Nov. 2022.

Valdivia, R.; Ammerman, C. B.; Henry, P. R.; Feaster, J. P.; Wilcox, C. J. "Effect of Dietary Aluminum and Phosphorus on Performance, Phosphorus Utilization and Tissue Mineral Composition in Sheep." Journal of Animal Science, 1982, vol. 55, No. 2, pp. 402-409. American Society of Animal Science, Champaign, Illinois, USA.

Valdivia, R.; Ammerman, C. B.; Wilcox, C. J.; Henry, P. R. "Effect of Dietary Aluminum on Animal Performance and Tissue Mineral Levels in Growing Steers." Journal of Animal Science, 1978, vol. 47, No. 6, pp. 1351-1356. American Society of Animal Science, Champaign, Illinois, USA.

Wächter, S., Cohrs, I., Golbeck, L., Wilkens, M. R., & Grünberg, W. "Effects of Restricted Dietary Phosphorus Supply to Dry Cows on Periparturient Calcium Status." Journal of Dairy Science, 2022, vol. 105, pp. 748-760. Published by Elsevier Inc. and Fass Inc. on behalf of the American Dairy Science Association, United States.

Wächter, S.; Cohrs, I.; Golbeck, L.; Scheu, T.; Eder, K.; Grünberg, W. "Effects of restricted dietary phosphorus supply during the dry period on productivity and metabolism in dairy cows." Journal of Dairy Science, 2022, vol. 105, pp. 4370-4392. Published by Elsevier Inc. and Fass Inc. on behalf of the American Dairy Science Association, United States.

Serum phosphorus concentrations vs dietary phosphorus in parous closeup dry cows on commercial dairies as a linear regression. Samples collected on herds regardless of diet ingredients or commercial products used in diet; n = 2,785.

Serum calcium concentrations vs dietary phosphorus in parous closeup dry cows on commercial dairies as a linear regression. Samples collected on herds regardless of diet ingredients or commercial products used in diet; n = 2,785.

ANI vs Al – DCAD Trial

Far off cows, closeup diet

- 18 multiparous Holstein cows
- Days in gestation = 208-227
- Animals housed in tie stall barn 3 Treatments

- 7 day covariate period
- 14 day treatment period

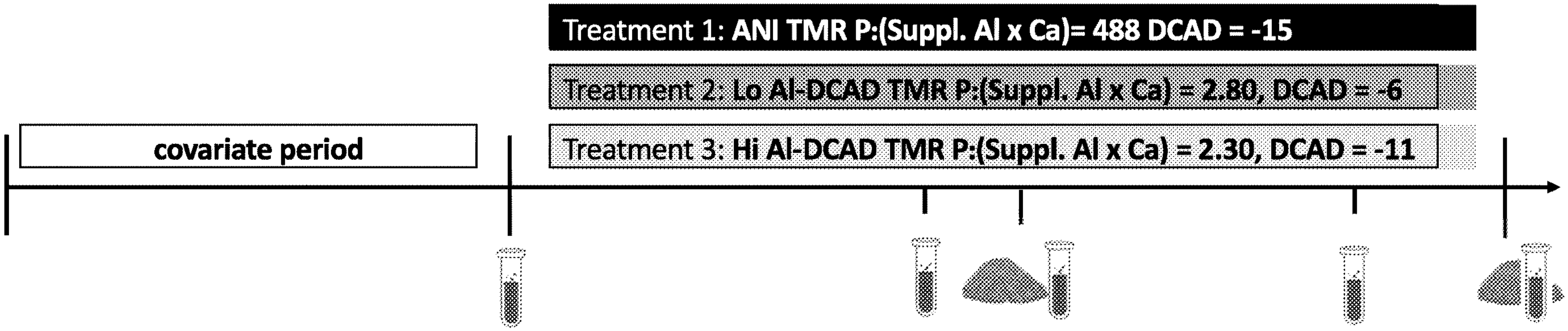

Parous dry cows enrolled on 1 of 3 diets top-dressed with 1) ANI: commercial dry anionic product to reach a diet DCAD = -15 mEq/100 g DM and P:(Suppl. Al x Ca) = 488; 2) Lo Al-DCAD: Al-DCAD to reach a diet DCAD = -6 mEq/100 g DM and P:(Suppl. Al x Ca) = 2.80; Hi Al-DCAD: to reach a diet DCAD = -11 mEq/100 g DM and P:(Suppl. Al x Ca) = 2.30.

FIG.10

Serum calcium sampled by day on treatments in parous dry cows enrolled on 1 of 3 diets top-dressed with 1) ANI: commercial dry anionic product to reach a diet DCAD = -15 mEq/100 g DM and P:(Suppl. Al x Ca) = 488; 2) Lo Al-DCAD: Al-DCAD to reach a diet DCAD = -6 mEq/100 g DM and P:(Suppl. Al x Ca) = 2.80; 3) Hi Al-DCAD: Al-DCAD to reach a diet DCAD = -11 mEq/100 g DM and P:(Suppl. Al x Ca) = 2.30.

Serum phosphorus sampled by day on treatments in parous dry cows enrolled on 1 of 3 diets top-dressed with 1) ANI: commercial dry anionic product to reach a diet DCAD = -15 mEq/100 g DM and P:(Suppl. Al x Ca) = 488; 2) Lo Al-DCAD: Al-DCAD to reach a diet DCAD = -6 mEq/100 g DM and P:(Suppl. Al x 3) Hi Al-DCAD: Al-DCAD to reach a diet DCAD = -11 mEq/100 g DM and P:(Suppl. Al x Ca) = 2.30.

Urine pH sampled by day on treatments in parous dry cows enrolled on 1 of 3 diets top-dressed with 1) ANI: commercial dry anionic product to reach a diet DCAD = -15 mEq/100 g DM and P:(Suppl. Al x Ca) = 488; 2) Lo Al-DCAD: Al-DCAD to reach a diet DCAD = -6 mEq/100 g DM and P:(Suppl. Al x Ca) = 2.80; 3) Hi Al-DCAD: Al-DCAD to reach a diet DCAD = -11 mEq/100 g DM and P:(Suppl. Al x Ca) = 2.30.

Urine pH averaged over study period in parous dry cows enrolled on 1 of 3 diets top-dressed 1) ANI: commercial dry anionic product to reach a diet DCAD = -15 mEq/100 g DM and P:(Suppl. Al x Ca) = 488; 2) Lo Al-DCAD: Al-DCAD to reach a diet DCAD = -6 mEq/100 g DM and P:(Suppl. Al x Ca) = 2.80; 3) Hi Al-DCAD: Al-DCAD to reach a diet DCAD = -11 mEq/100 g DM and P:(Suppl. Al x Ca) = 2.30.

Daily dry matter intake in parous dry cows enrolled on 1 of 3 diets top-dressed with 1) ANI: commercial dry anionic product to reach a diet DCAD = -15 mEq/100 g DM and P:(Suppl. Al x Ca) = 488; 2) Lo Al-DCAD: Al-DCAD to reach a diet DCAD = -6 mEq/100 g DM and P:(Suppl. Al x Ca) = 2.80; 3) Hi Al-DCAD: Al-DCAD to reach a diet DCAD = -11 mEq/100 g DM and P:(Suppl. Al x Ca) = 2.30.

Serum calcium levels averaged by days in milk class of parous closeup cows and multiparous fresh cows on commercial dairies. Fresh cows (1-4 DIM) and closeup cows (-1 DIM) were fed a closeup diet feed ingredient of None n = 354; Anionic n = 7,240; Dry Phos Binder n = 440; or Al-DCAD n = 1,200

Incidence rate of cows classified as hypocalcemic at 1 and 4 DIM. Multiparous cows from commercial dairies fed closeup ration with None, Anionic, Dry Phos Binder, and Al-DCAD were classified with 1 DIM serum Ca < 7.10 mg/dL, with 4 DIM serum Ca < 8.82 mg/dL (McArt and Neves, 2020)

Serum phosphorus levels averaged by days in milk class of parous closeup and multiparous fresh cows on commercial dairies. Fresh cows (1-4 DIM) and closeup cows (-1 DIM) were fed a closeup diet feed ingredient of None n = 354; Anionic n = 7,233; Dry Phos Binder n = 440; or Al-DCAD n = 1,200

Serum phosphorus in closeup cows vs diet phosphorus:supplemental aluminum for parous dry cows on commercial dairies plotted as a locally weighted linear regression. Samples from closeup diets fed Dry Phos Binder n = 142, or Al – DCAD n = 759.

Serum phosphorus in closeup cows vs diet phosphorus:(supplemental aluminum x calcium) for dry cows on commercial dairies plotted as a locally weighted linear regression. Samples from closeup diets fed Dry Phos Binder n = 142, or Al – DCAD n = 759

Strong ion difference (SID; [Na] + [K] – [Cl] mEq/L ) vs dietary phosphorus:supplemental aluminum in closeup parous dry cows on commercial dairies as a locally weighted linear regression. Samples from closeup diets fed Dry Phos Binder n = 142, and Al – DCAD n = 759

Serum phosphorus vs dietary DCAD in closeup parous dry cows on commercial dairies as a locally weighted linear regression. Samples from closeup diets fed Dry Phos Binder n = 142, Al – DCAD n = 759, Anionic n = 1,368

Serum phosphorus vs dietary calcium in closeup parous dry cows on commercial dairies as a locally weighted linear regression. Samples from closeup diets fed Dry Phos Binder n = 142, and Al – DCAD n = 759

Serum phosphorus vs dietary calcium:phosphorus ratio in closeup parous dry cows on commercial dairies as a locally weighted linear regression. Samples from closeup diets fed Dry Phos Binder n = 142, and Al – DCAD n = 759

Serum calcium 1-2 days in milk of multiparous cows vs dietary phosphorus:supplemental aluminum in closeup ration on commercial dairies as a locally weighted linear regression. Samples from closeup diets fed Dry Phos Binder n = 90, and Al – DCAD n = 186

Serum calcium 1-4 days in milk of multiparous cows vs dietary phosphorus:supplemental aluminum in closeup ration on commercial dairies as a locally weighted linear regression. Samples from closeup diets fed Dry Phos Binder n = 189, and Al – DCAD n = 372

Serum Calcium 1-2 DIM for multiparous cows vs diet phosphorus:(supplemental aluminum x calcium) in closuep ration on commercial dairies plotted as a locally weighted linear regression. Samples from closeup diets fed Dry Phos Binder n = 90, or Al – DCAD n = 186

Serum Calcium 1-4 DIM for multiparous cows vs diet phosphorus:(supplemental aluminum x calcium ) in closeup ration on commercial dairies plotted as a locally weighted linear regression. Samples from closeup diets fed Dry Phos Binder n = 189, or Al – DCAD n = 372

Serum calcium 1-2 days in milk of multiparous cows vs dietary cation anion difference of closeup ration on commercial dairies as a locally weighted linear regression. Samples from closeup diets fed Dry Phos Binder n = 90, Al – DCAD n = 186, Anionic n = 1,482

Serum calcium 1-4 days in milk of multiparous cows vs dietary cation anion difference of closeup ration on commercial dairies as a locally weighted linear regression. Samples from closeup diets fed Dry Phos Binder n = 189, Al – DCAD n = 372, Anionic n = 2,938

Milk fever incidence by month for multiparous cows across 3 dairies (A, B, C). Dairies were feeding Anionic and switched to Al-DCAD. Plotted by month relative to start of Al-DCAD feeding.
A)
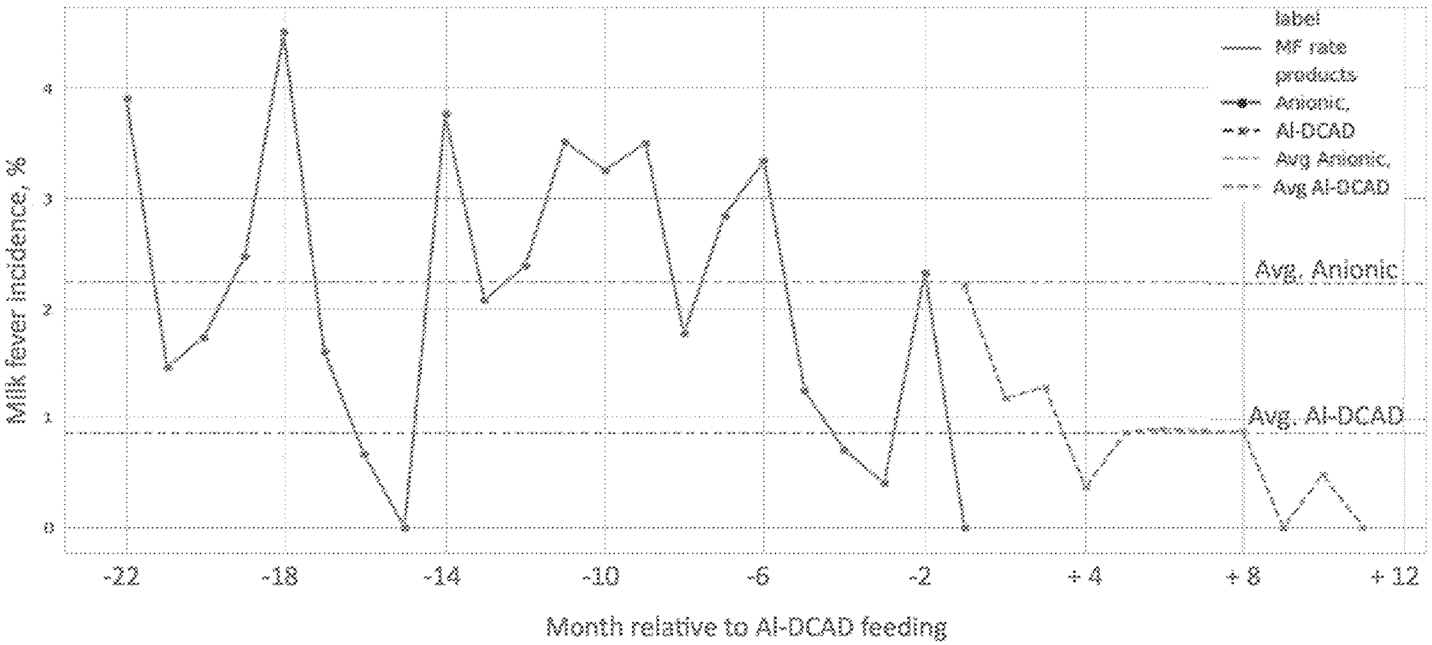
FIG.31.A B)
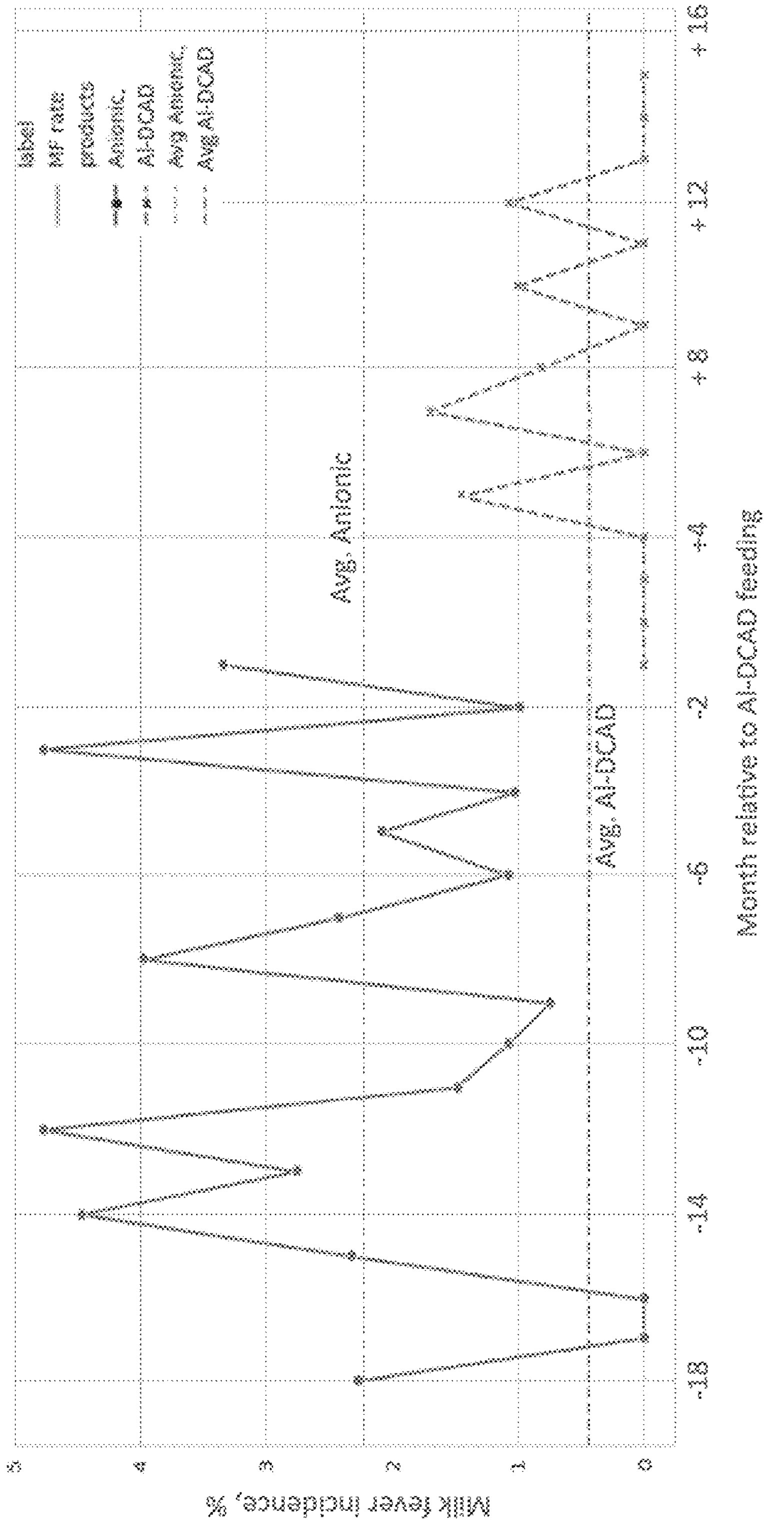
FIG.31.B C)
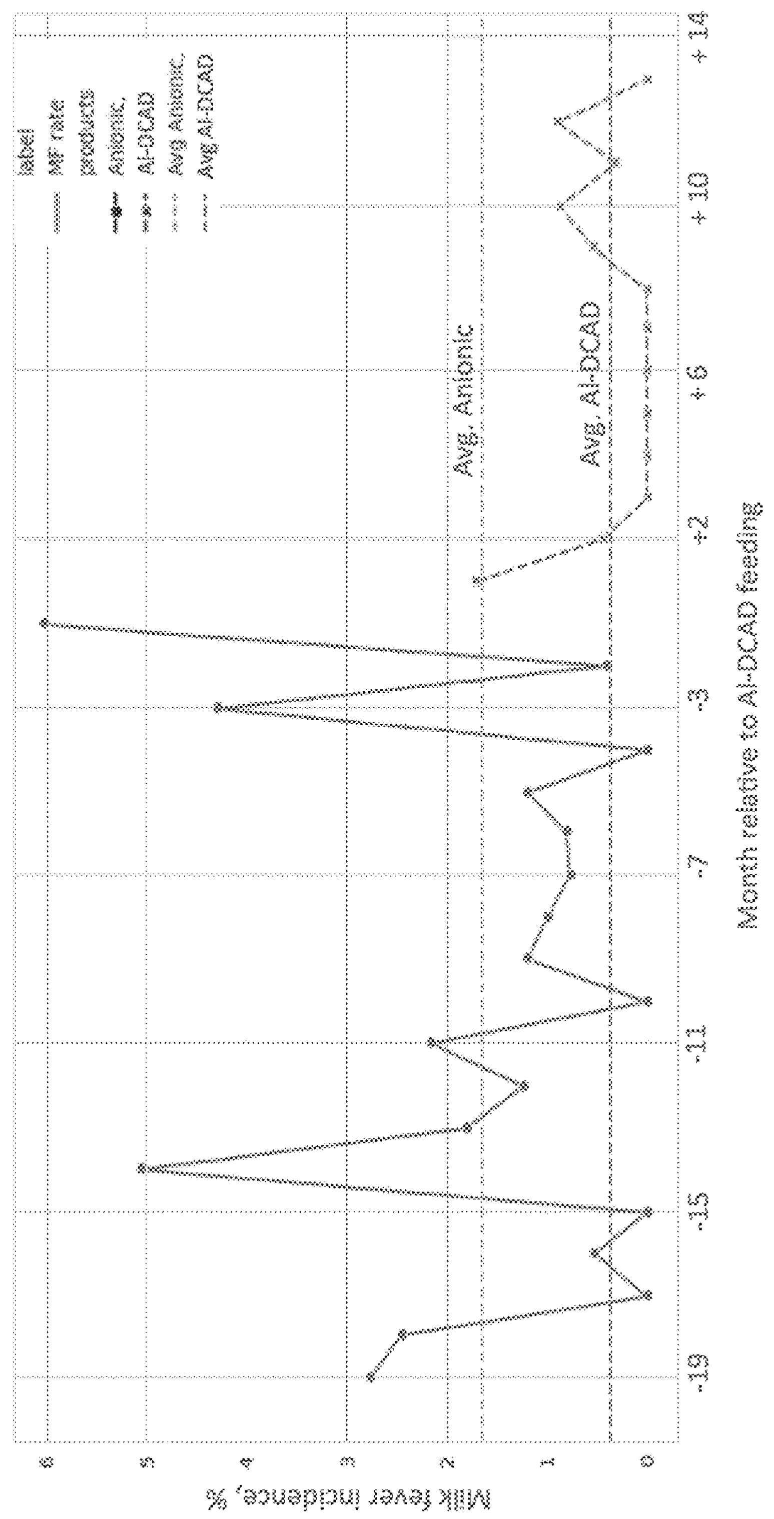
FIG.31.C Mastitis incidence rate for multiparous cows < 60 days in milk for dairy farms that have fed both Anionic and Al-DCAD farm n = 30.

Mastitis incidence rate for multiparous cows < 60 days in milk for dairy farms that have fed Dry Phos Binder and moved to Al-DCAD, farm n = 7.

Died & sold incidence rate for multiparous cows < 60 days in milk for dairy farms that have fed Anionic and moved to AI-DCAD farm n = 32.

Died & sold incidence rate for multiparous cows < 60 days in milk for dairy farms that have fed Dry Phos Binder and moved to Al-DCAD farm n = 7.

Milk fever incidence rate for multiparous cows for dairy farms that have fed Anionic and moved to Al-DCAD, farm n = 20.

Milk fever incidence rate for multiparous cows for dairy farms that have fed Dry Phos Binder and moved to Al-DCAD, farm n = 6.

Daily milk yield reported by cow/day from 6 commercial dairy herds reported across the first 28 DIM/first 4 weeks of lactation. Averages reported for the previous year on Dry Phos Binder, the averages after switching to Al-DCAD, and the difference between the averages reported with the arrows.

DIETARY COMPOSITION FOR DAIRY COWS WITH ALUMINUM SUPPLEMENTATION AND CONTROLLED DCAD

CROSS-REFERENCE TO RELATED APPLICATIONS

This application claims the priority of each of these prior application(s) having the same title and named inventors as this application: U.S. provisional application No. 63/872,300 filed Aug. 28, 2025; and U.S. provisional application No. 63/894,602 filed Oct. 6, 2025.

TECHNICAL FIELD

This disclosure is in the field of animal nutrition and feed compositions. More particularly, this disclosure relates to dietary formulations for dairy cows to manage mineral balance and metabolic health during the prepartum period, aiming to reduce conditions such as hypocalcemia and milk fever postpartum.

SUMMARY

In an aspect, the disclosure provides a total dietary composition (TDC) for dairy cows, the TDC comprising:

(A) a basal diet; and (B) a supplemental source of one or more phosphorus-binding elements comprising one or more chemical sources of aluminum(III);

wherein the TDC has:

(i) a phosphorus-to-aluminum weight ratio of 1.5:1 to 2.5:1 based on total dietary phosphorus and aluminum from the chemical sources of aluminum(III), measured on a dry matter basis; and (ii) a Dietary Cation-Anion Difference (DCAD) of −15 to +10 mEq/100 g dry matter calculated as ([Na]+[K])—[Cl]+[S]).

In another aspect, the disclosure provides a total dietary composition (TDC) for dairy cows, the TDC comprising:

(A) a basal diet; and (B) a supplemental source of one or more phosphorus-binding elements comprising one or more chemical sources of aluminum(III);

wherein the TDC has:

(i) a phosphorus-to-(aluminum times calcium) weight ratio of 1.8:1 to 4.0:1 based on total dietary phosphorus, aluminum from the one or more chemical sources of aluminum(III), and total dietary calcium, measured on a dry matter basis; and (ii) a Dietary Cation-Anion Difference (DCAD) of −15 to +10 mEq/100 g dry matter calculated as ([Na]+[K])—[Cl]+[S]).

In yet another aspect, the disclosure provides A total dietary composition (TDC) for dairy cows, the TDC comprising:

(A) a basal diet; and (B) a supplemental source of one or more phosphorus-binding elements selected from the group consisting of:

(i) one or more chemical sources of aluminum(III), (ii) one or more chemical sources of iron (II), iron(III), and any combination thereof, and (iii) any combination thereof;

wherein the TDC has:

(a) a phosphorus-to-binding-elements stoichiometric ratio of 1.3:1 to 2.2:1 based on total dietary phosphorus and the molar binding capacity of the phosphorus-binding elements from the supplemental source; and (b) a Dietary Cation-Anion Difference (DCAD) of −15 to +10 mEq/100 g dry matter calculated as ([Na]+[K])—[Cl]+[S]).

In addition, various dietary supplement compositions for dairy cows are provided, wherein the supplement is formulated to contribute to a total dietary composition having the above characteristics.

These and other aspects, embodiments, and advantages of the disclosure will be apparent to one skilled in the art upon reading the following detailed description. Those skilled in the art will appreciate that after reading the following detailed description of the disclosure, the parameters of the disclosure can be defined in other units and terminology without departing from the scope and spirit of the disclosure. Specific embodiments will be described in detail and shown by way of example. However, specific portions or functional details disclosed herein are merely representative for the purposes of describing example embodiments. The detailed description is not intended to limit the disclosure to only the particular forms disclosed.

BRIEF DESCRIPTION OF THE DRAWING

The accompanying figures of the drawing are incorporated into the specification to help illustrate examples according to various embodiments of the disclosure. Like references are used for like elements or features throughout the figures of the drawing. The figures of the drawing are not necessarily to scale.

These figures together with the description explain the general principles of the disclosure. The figures are only for the purpose of illustrating preferred and alternative examples of how the various aspects of the claimed inventions can be made and used and are not to be construed as limiting the claimed inventions to only the illustrated and described examples. Various advantages and features of the various aspects of the present inventions will be apparent from a consideration of the drawing.

Figure 1:
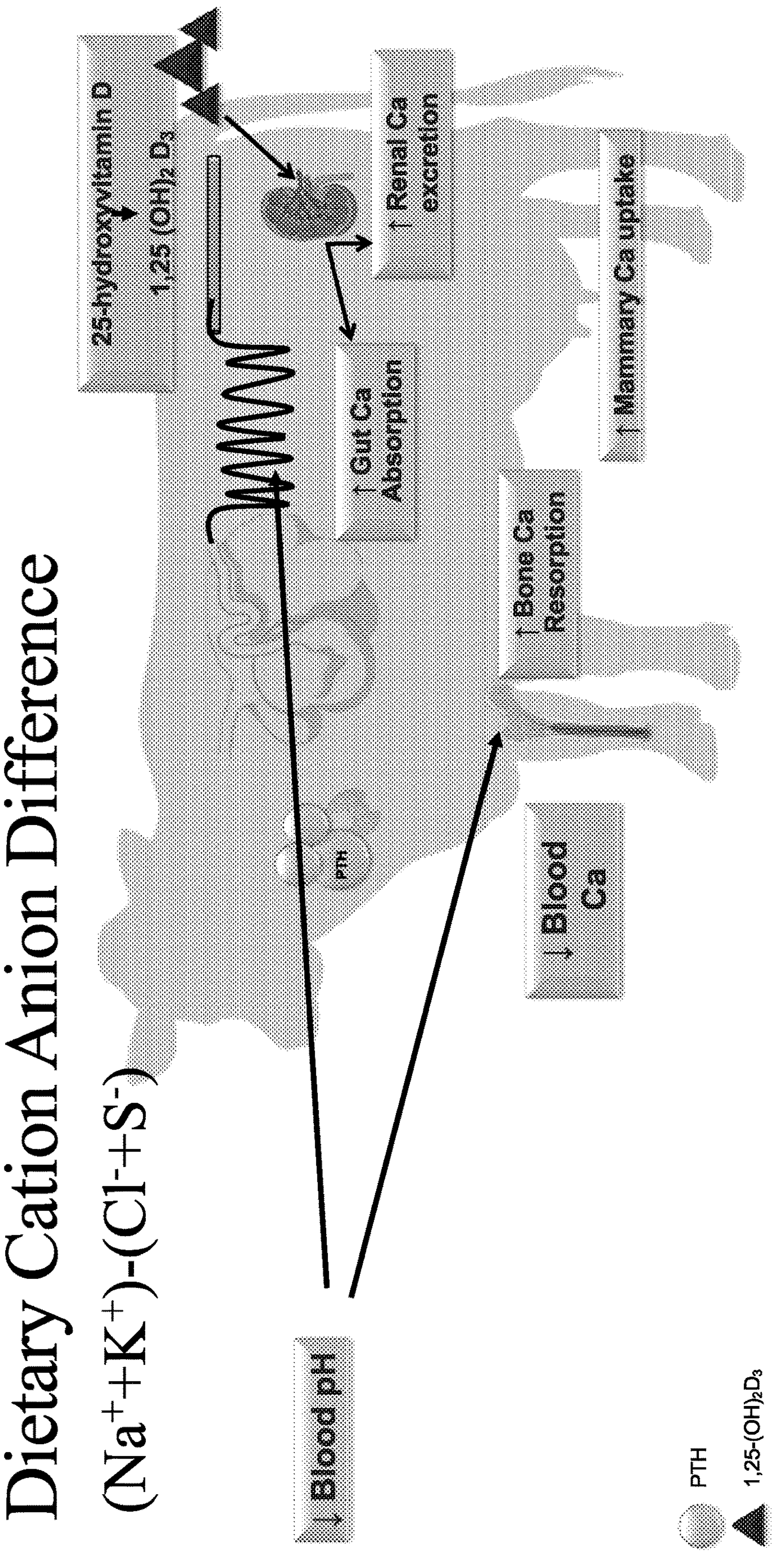

In some alternative embodiments, the functions or acts can occur out of the order noted in the figures. For example, two figures of the drawing shown in succession can in fact be executed substantially concurrently or can sometimes be executed in the reverse or order, depending upon the functionality or acts involved.

FIG. 1 is a schematic diagram illustrating calcium metabolism and regulation in a cow, showing interactions involving blood pH, PTH (parathyroid hormone), vitamin D derivatives, gut absorption, renal excretion, bone resorption, and mammary uptake.

Figure 2:
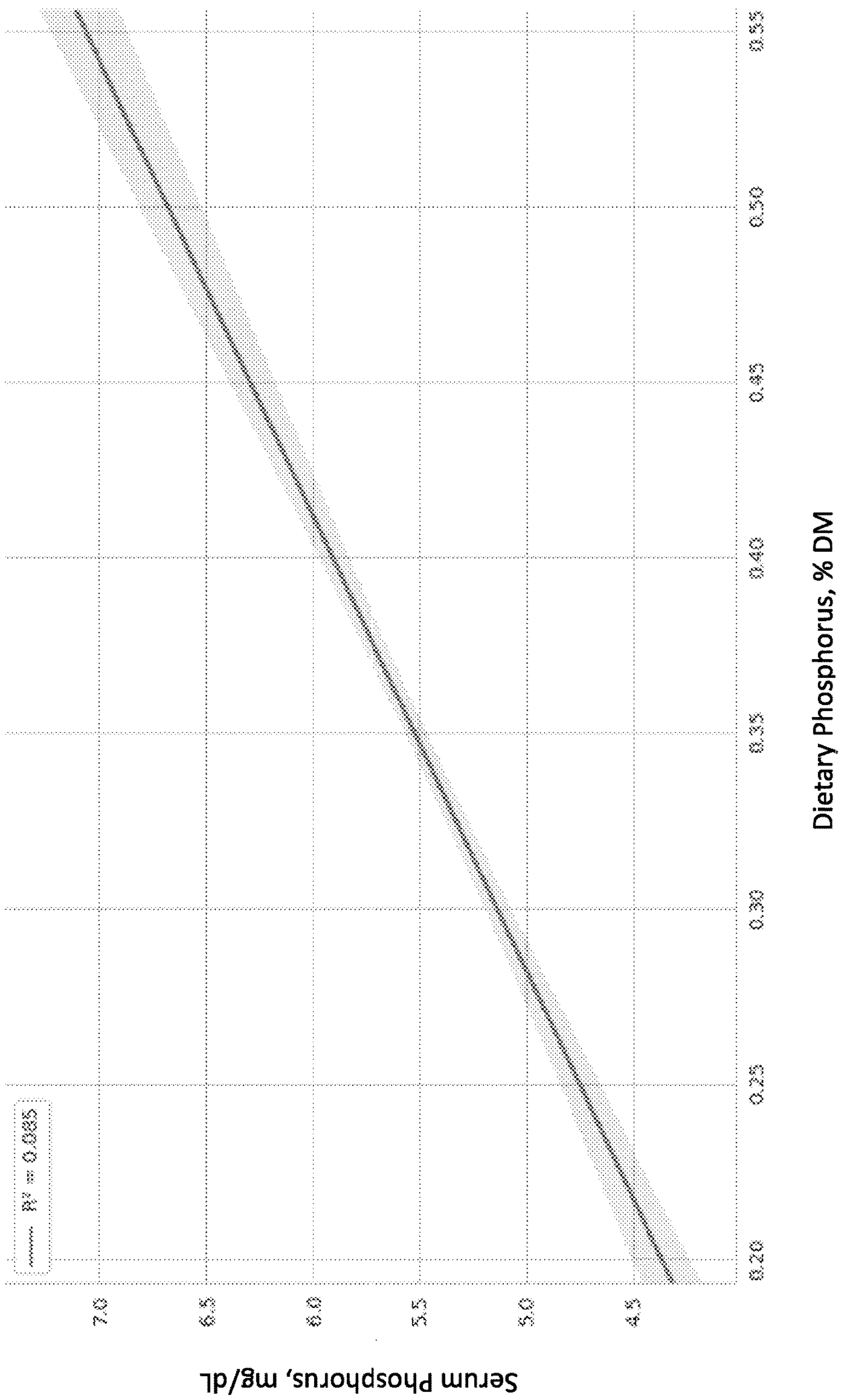

FIG. 2 is a graph showing a direct positive association between dietary phosphorus percentage and serum phosphorus levels in closeup prepartum cows based on field data.

Figure 3:
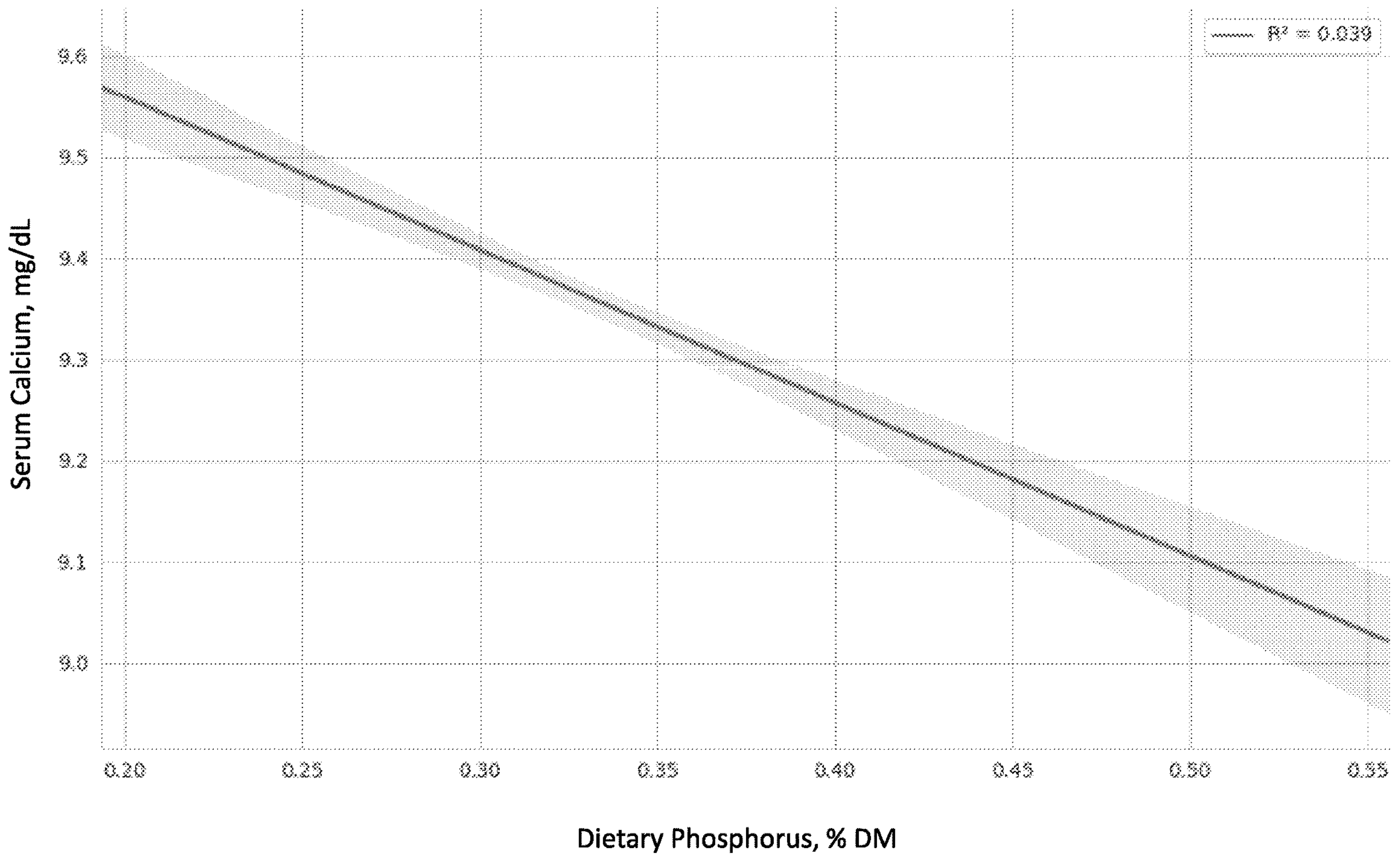

FIG. 3 is a graph showing an inverse association between dietary phosphorus percentage and serum calcium levels in closeup prepartum cows based on field data.

Figure 4:
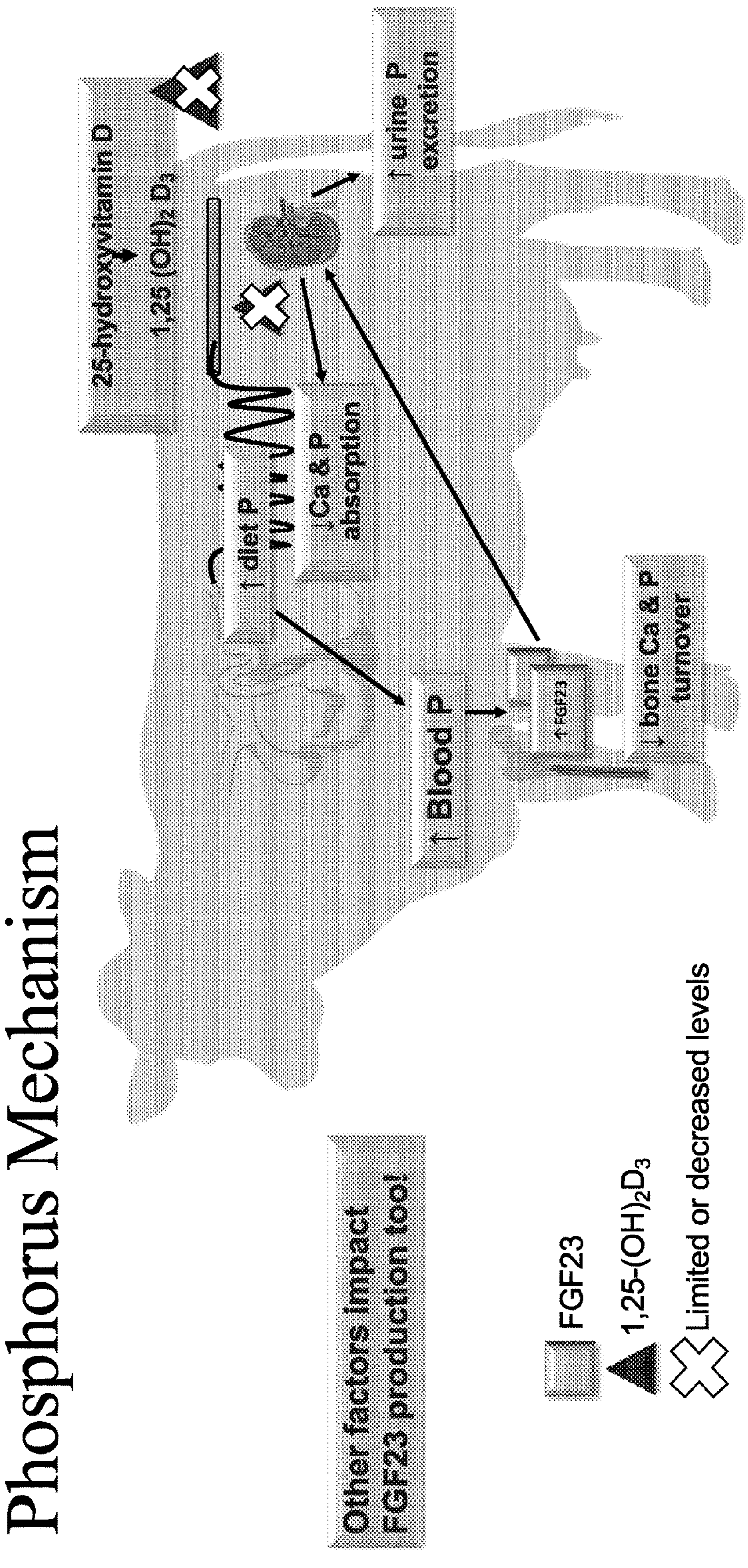

FIG. 4 is a schematic diagram illustrating phosphorus metabolism and regulation in a cow, showing interactions involving blood (serum) phosphorus, PTH (parathyroid hormone), fibroblast growth factor 23 (FGF23), vitamin D derivatives, bone turnover, gut absorption, and urine excretion.

Figure 5:
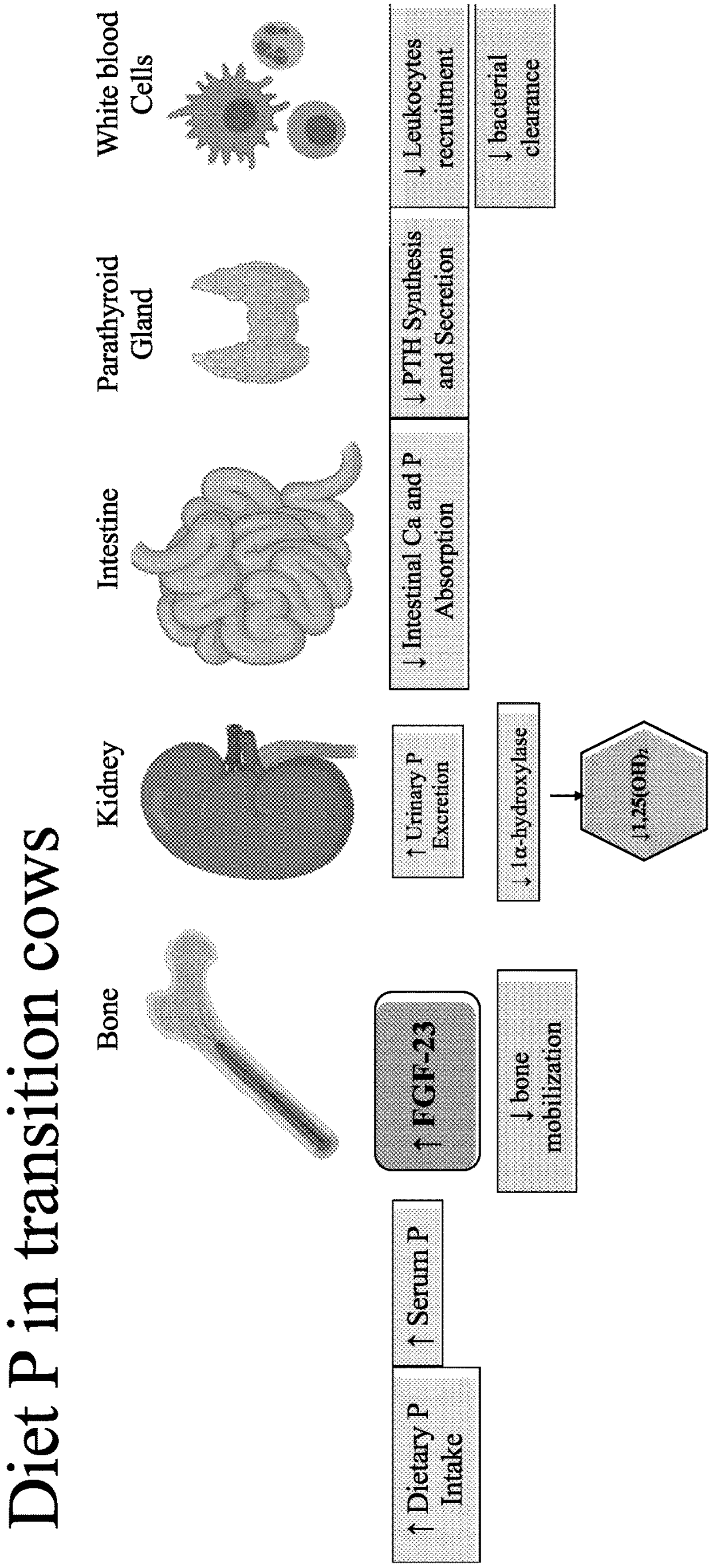

FIG. 5 is a schematic diagram showing dietary phosphorus transition in cows, including increased fibroblast growth factor 23 (FGF23) mRNA expression in bone tissue.

Figure 6:
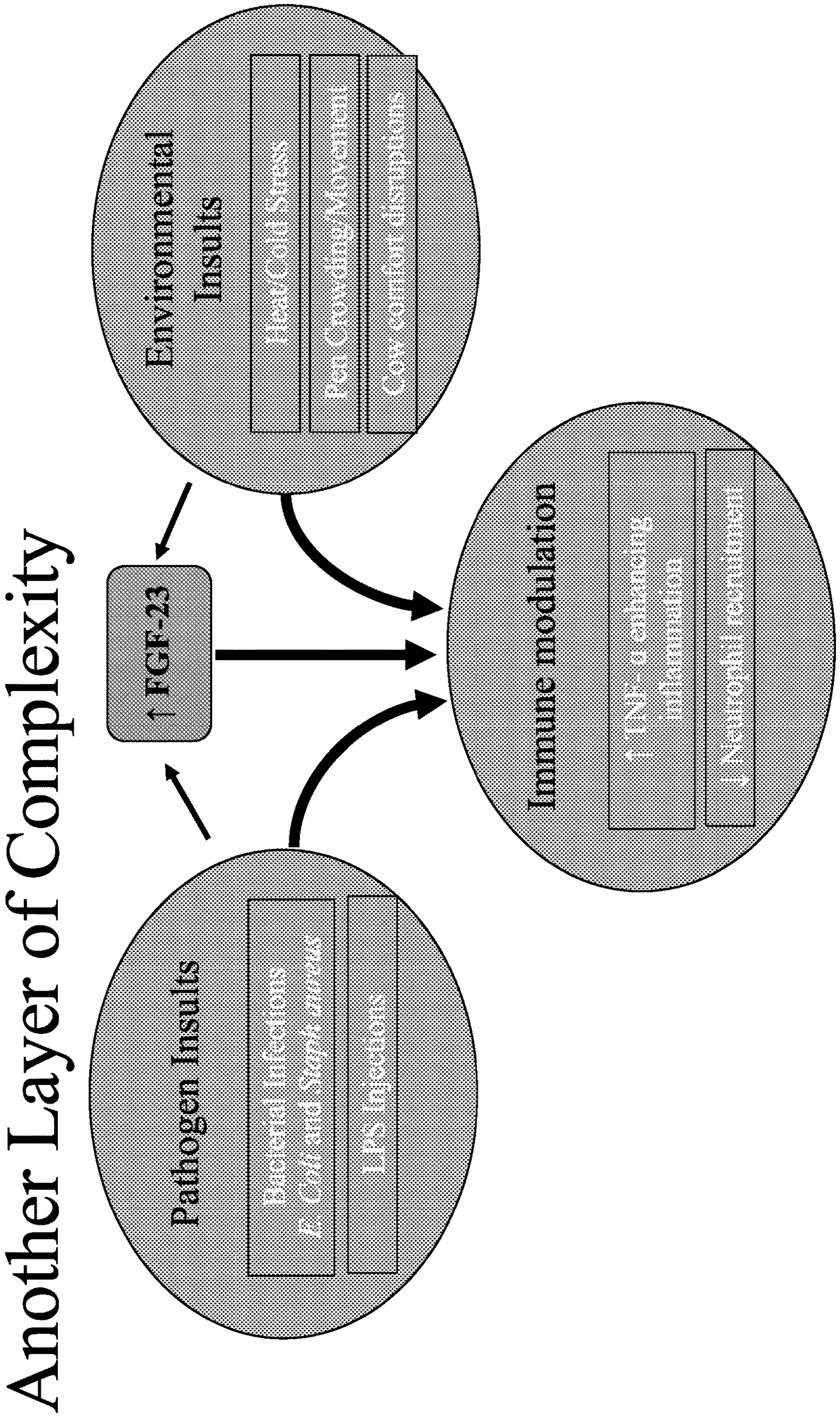

FIG. 6 is a schematic diagram of complexities in transition cows, including relationships between pathogen insults such as bacterial infections and LPS (lipopolysaccharide) injections, fibroblast growth factor 23 (FGF23), immune modulation, such as TNF-α (tumor necrosis factor-alpha) enhancing inflammation and alterations to neutrophil recruitment, and environmental insults, such as heat/cold stress, pen crowding/movement, and cow comfort disruptions.

Figure 7:
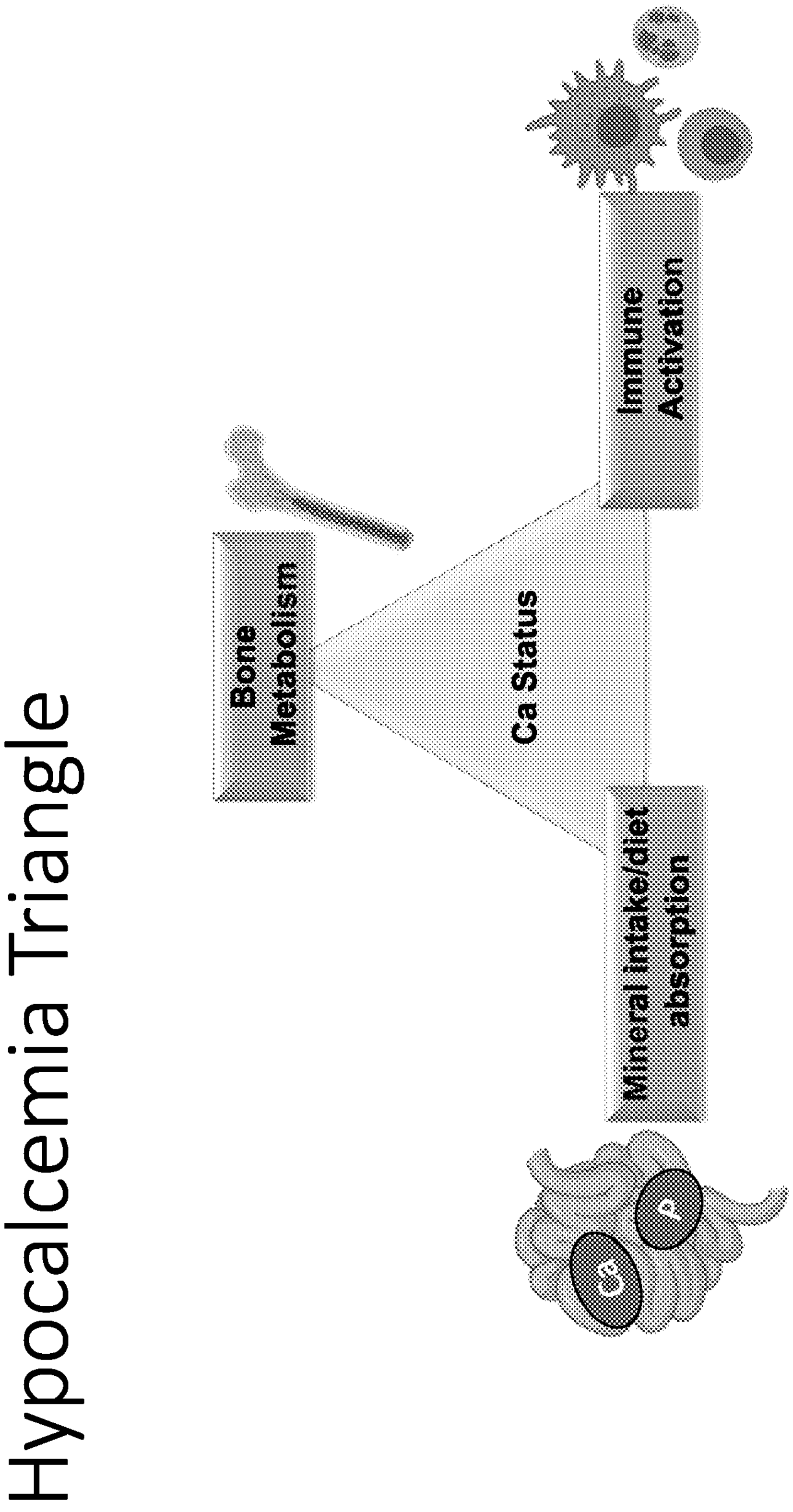

FIG. 7 is a triangular diagram depicting the hypocalcemia triangle in dairy cows, interrelating calcium status with bone metabolism, mineral intake absorption, and immune activation.

Figure 8:
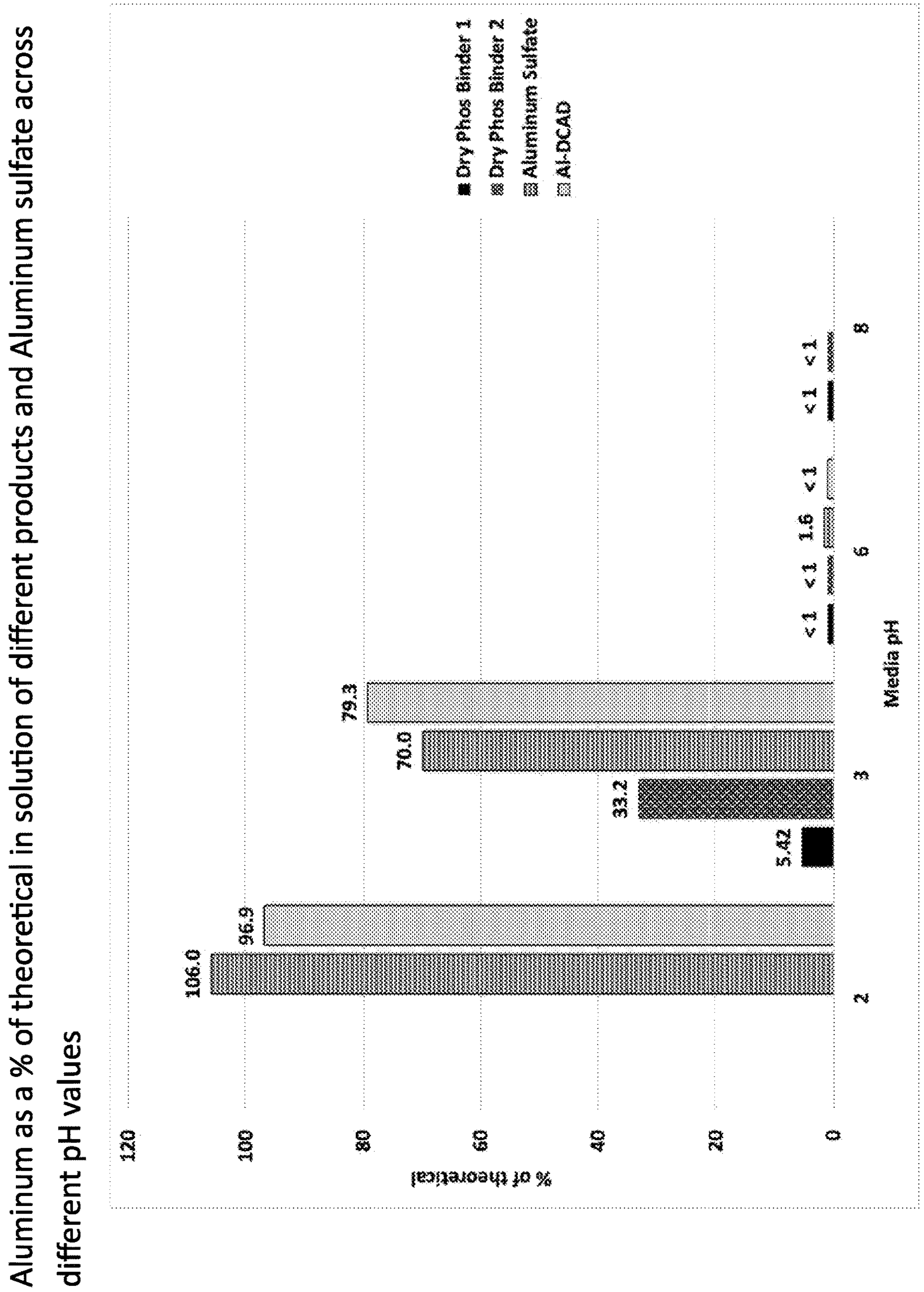

FIG. 8 is a graph showing aluminum solubility of several aluminum containing products at varying media pH levels.

Figure 9:
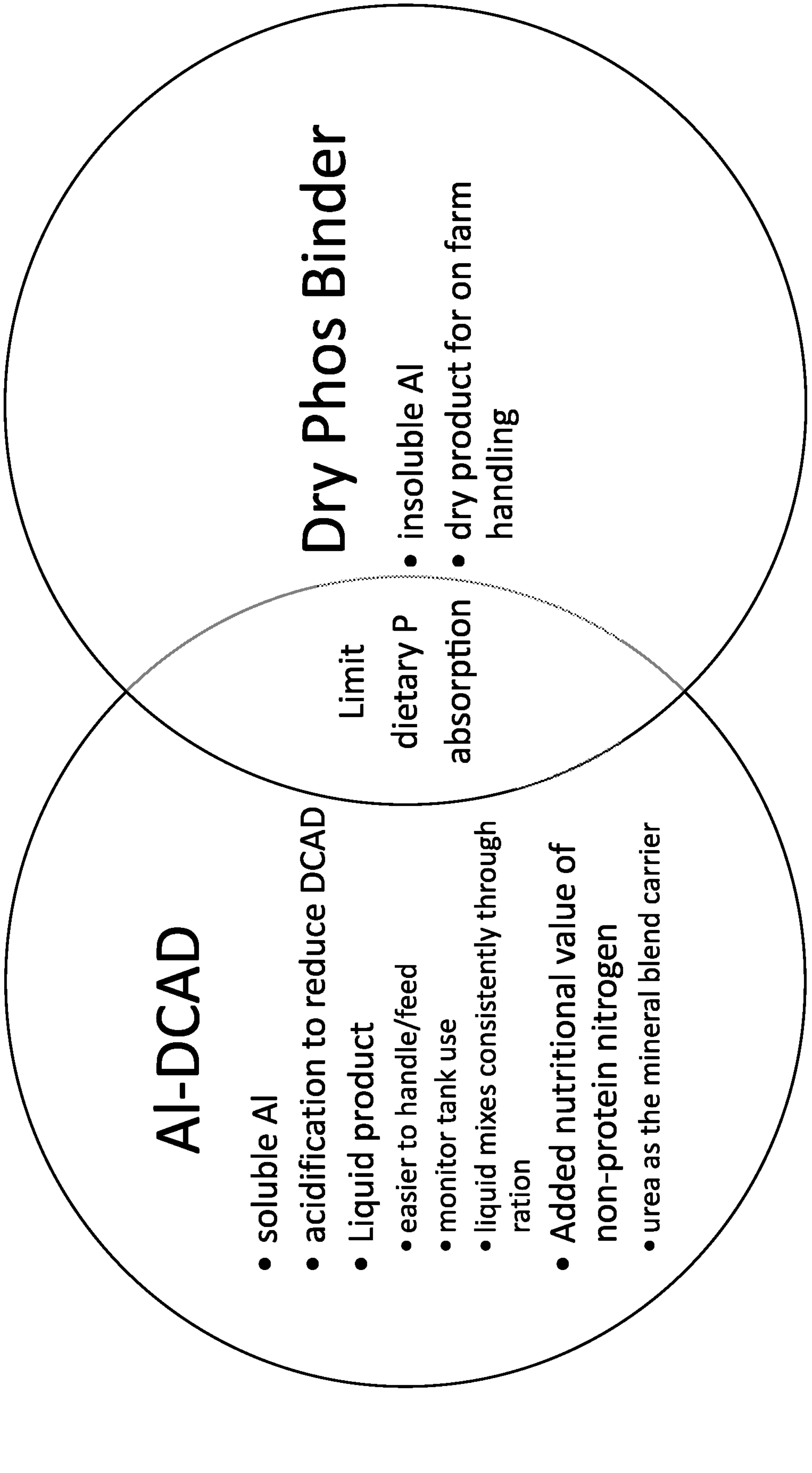

FIG. 9 is a Venn diagram comparing features of Al-DCAD and a dry phosphorus binder, including solubility of aluminum, product form, handling characteristics, and additional nutritional values.

FIG. 10 is a schematic timeline of the trial structure for ANI and Al-DCAD products, including pre-treatment covariate and treatment periods with indicated blood and urine sampling days for anionic (ANI), low Al-DCAD, and high Al-DCAD treatments.

Figure 11:
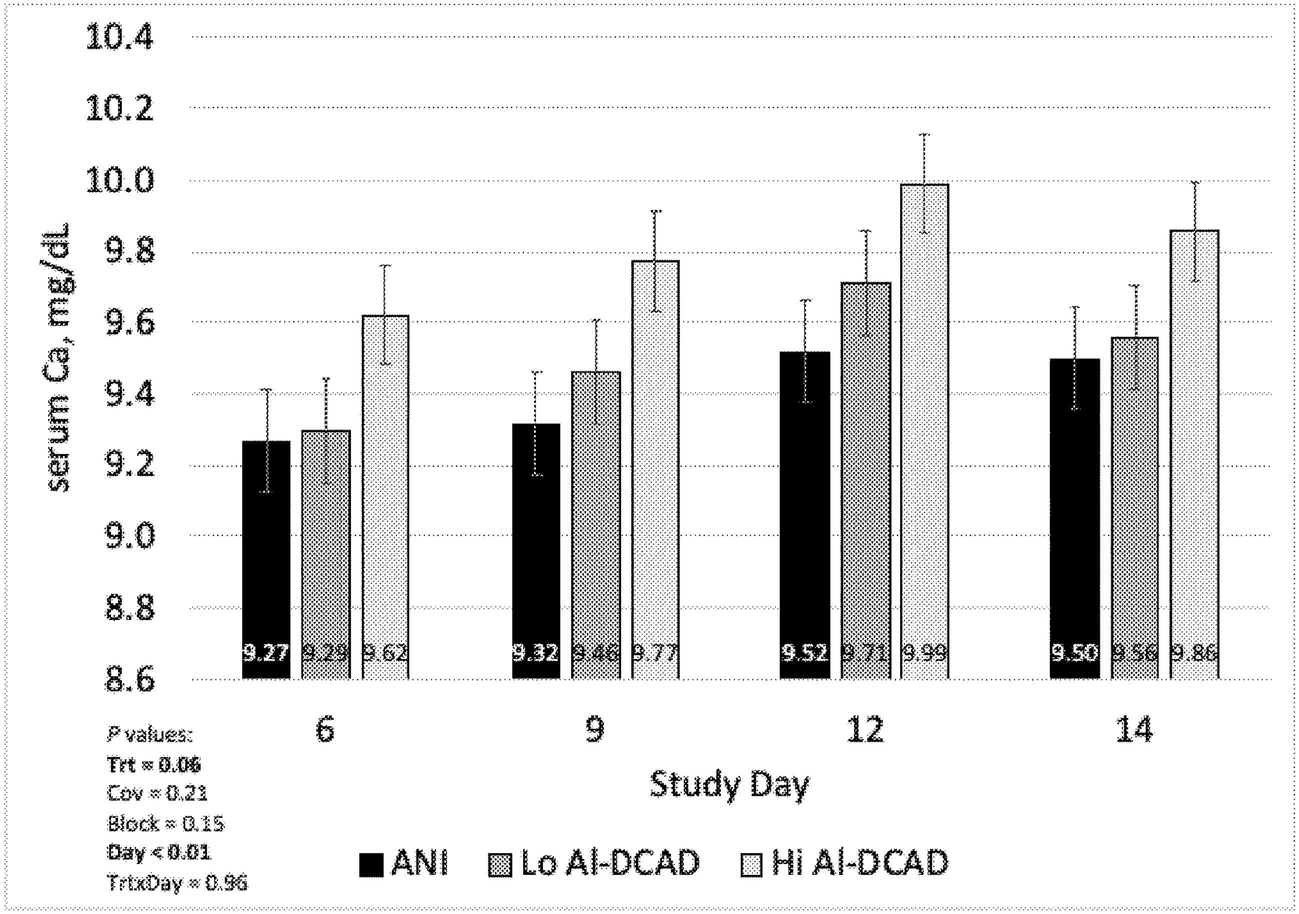

FIG. 11 is a bar chart comparing serum calcium concentrations over treatment days for anionic (ANI), low Al-DCAD, and high Al-DCAD treatments in parous cows.

Figure 12:
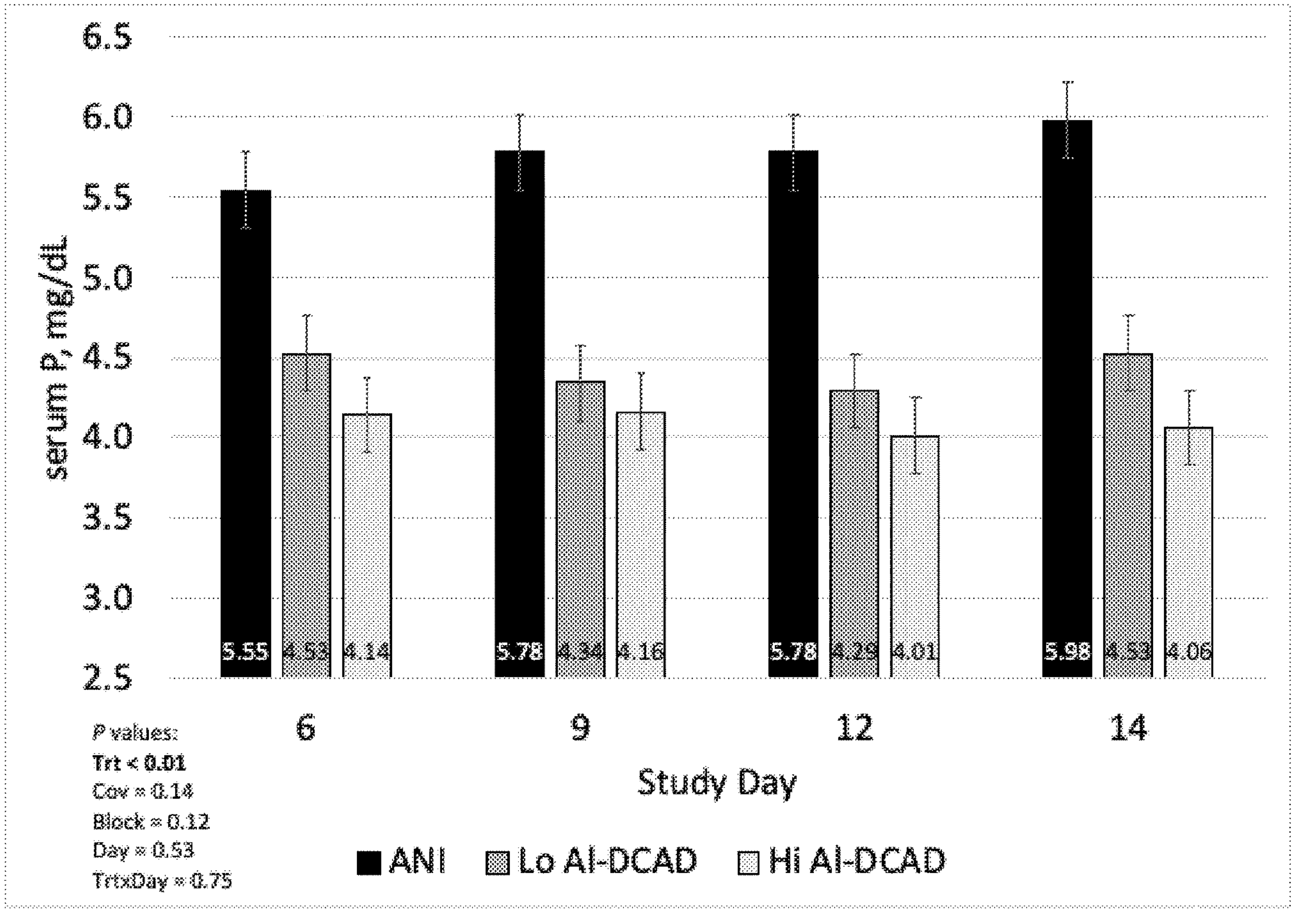

FIG. 12 is a bar chart comparing serum phosphorus concentrations over treatment days for anionic (ANI), low Al-DCAD, and high Al-DCAD treatments in parous cows.

Figure 13:
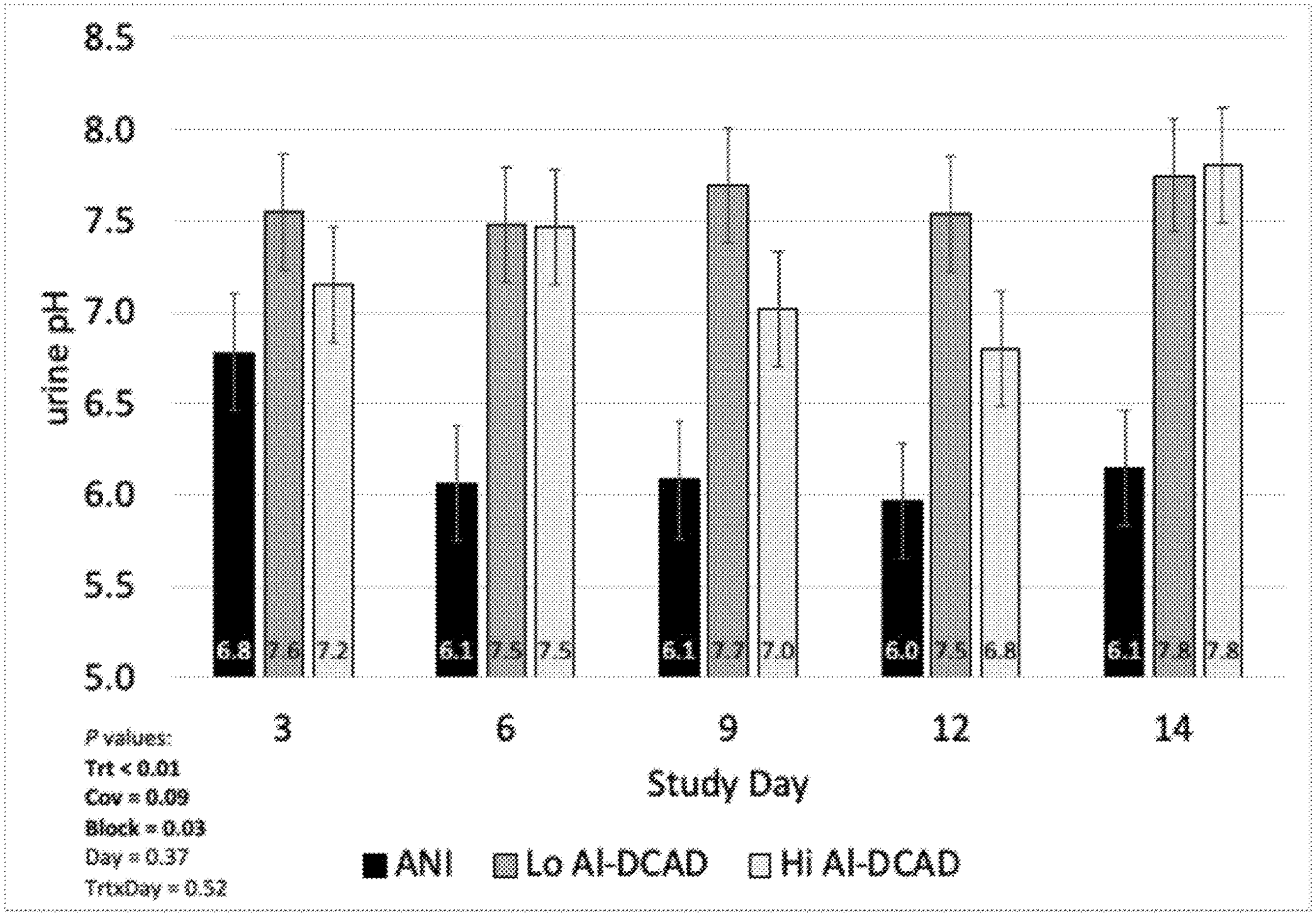

FIG. 13 is a bar chart comparing average cow urine pH over treatment days for anionic (ANI), low Al-DCAD, and high Al-DCAD treatments in parous cows.

Figure 14:
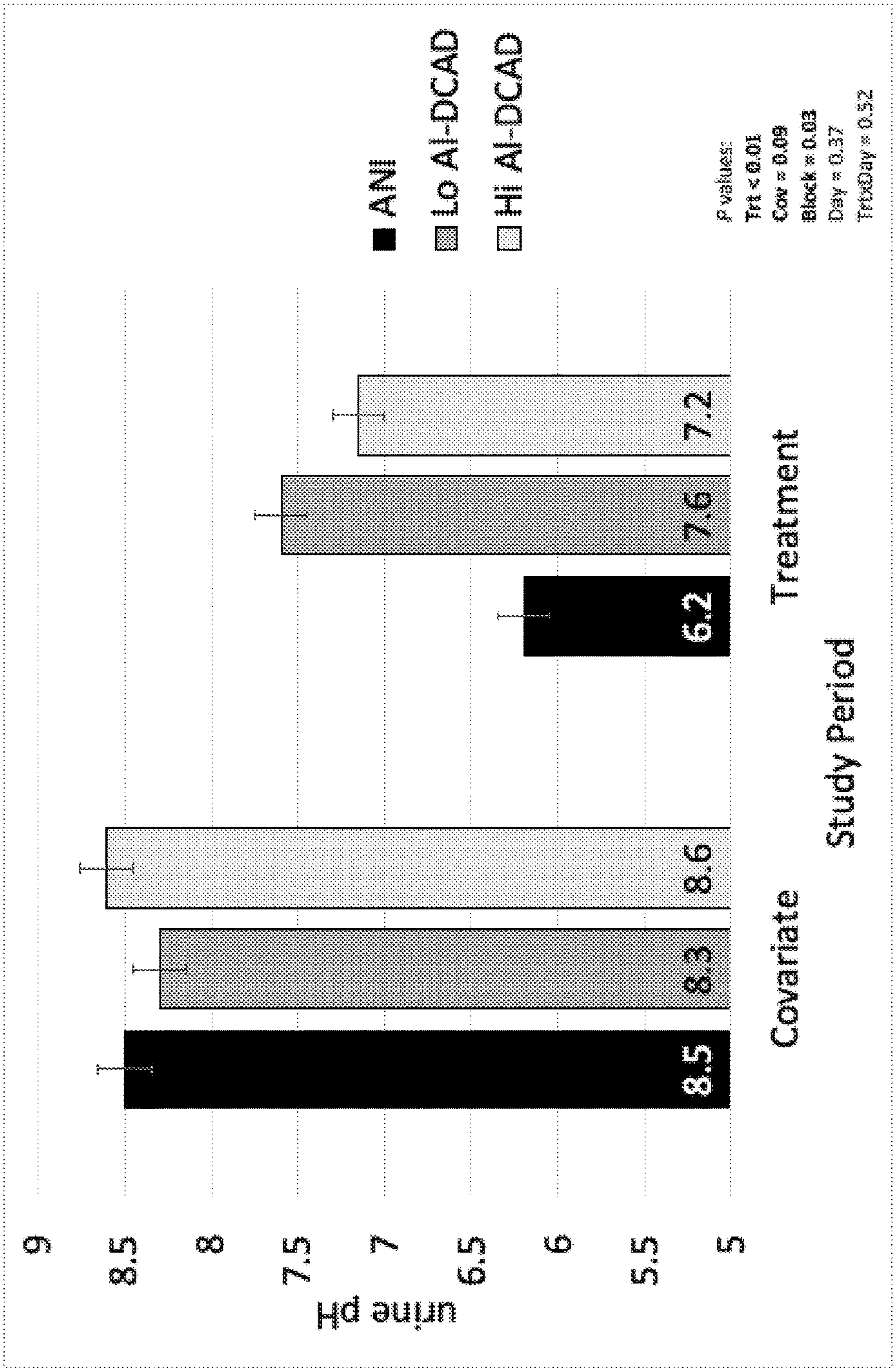

FIG. 14 is a bar chart comparing average cow urine pH over the entire study periods for anionic (ANI), low Al-DCAD, and high Al-DCAD treatments in parous cows.

Figure 15:
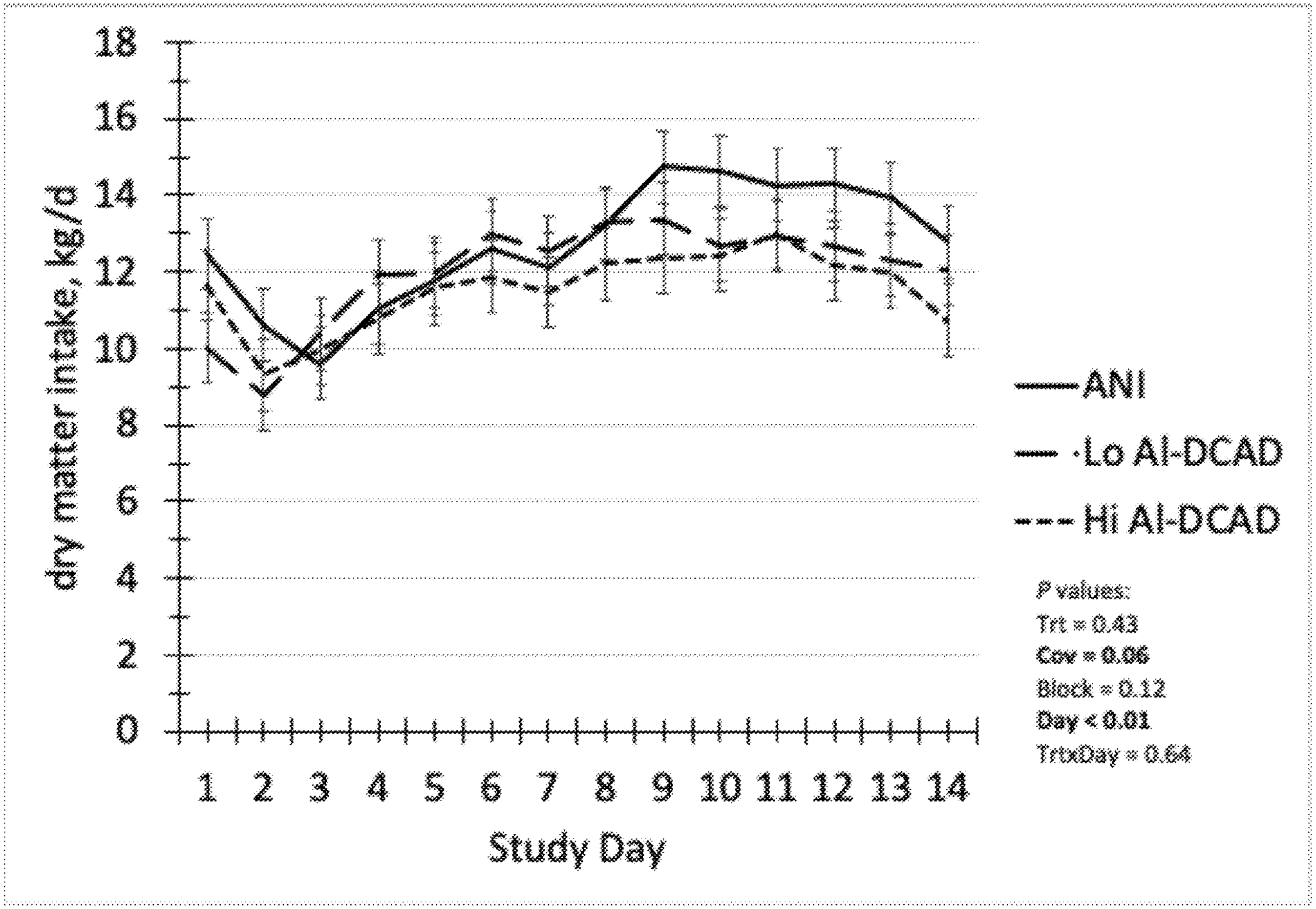

FIG. 15 is a graph comparing average dry matter intake over treatment days for anionic (ANI), low Al-DCAD, and high Al-DCAD treatments in parous cows.

Figure 16:
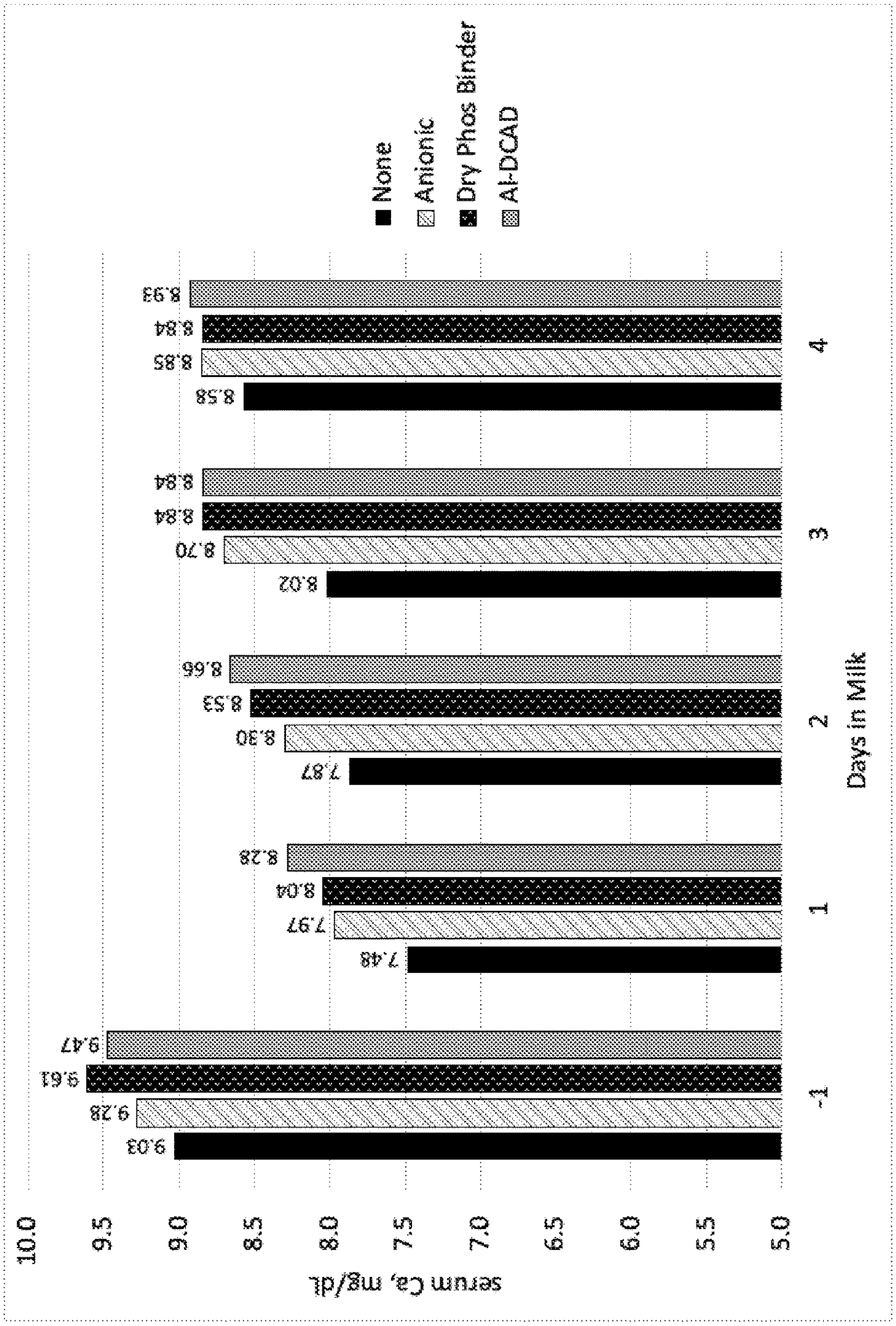

FIG. 16 is a bar chart comparing serum calcium levels of cows on commercial dairies among None (as a control), Anionic (aka ANI), a Dry Phos Binder, and Al-DCAD treatments across days in milk (DIM).

Figure 17:
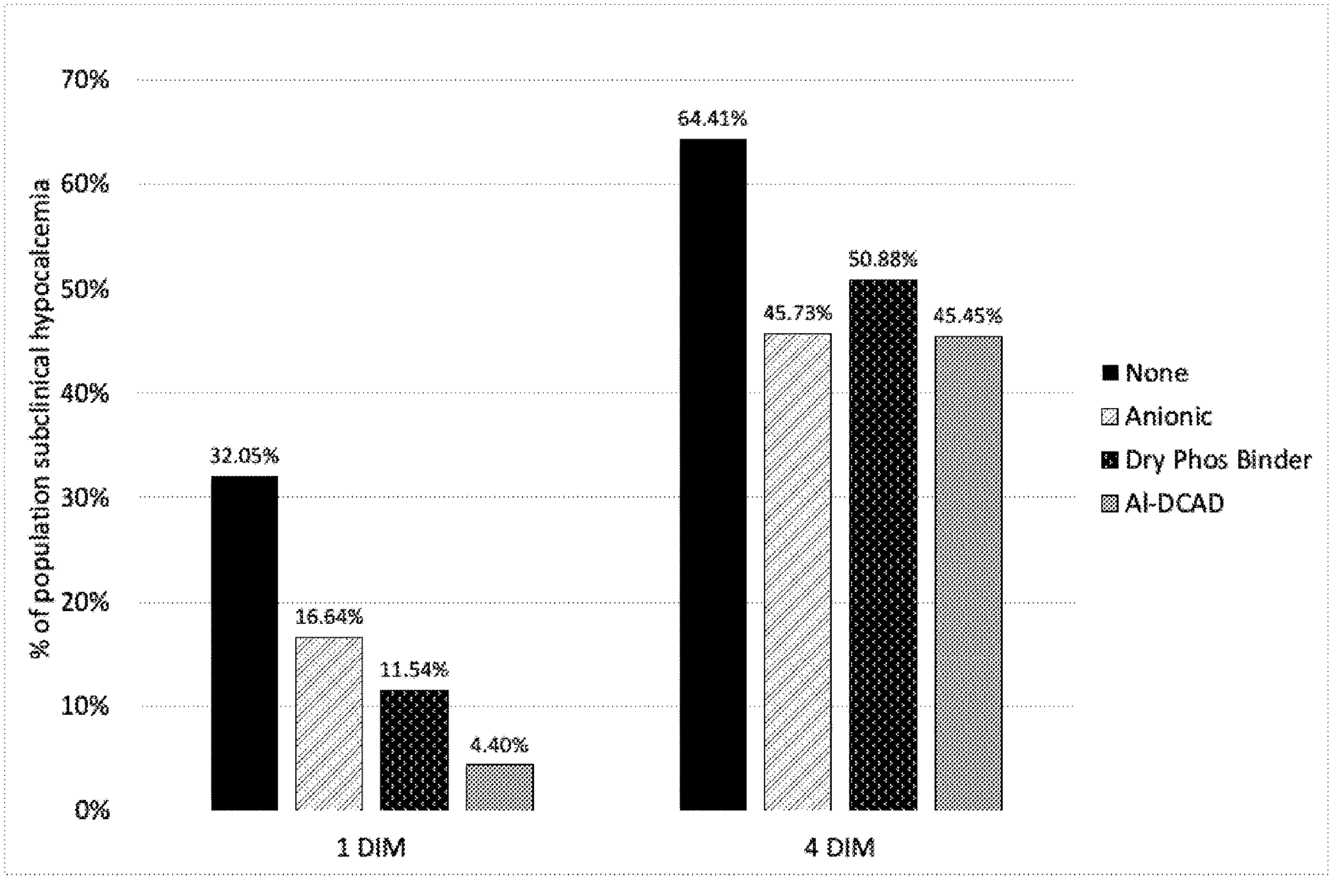

FIG. 17 is a bar chart comparing the percentage of the cow population on commercial dairies showing subclinical hypocalcemia among None (as control), Anionic (aka ANI), Dry Phos Binder, and Al-DCAD treatments for 1 and 4 days in milk (DIM).

Figure 18:
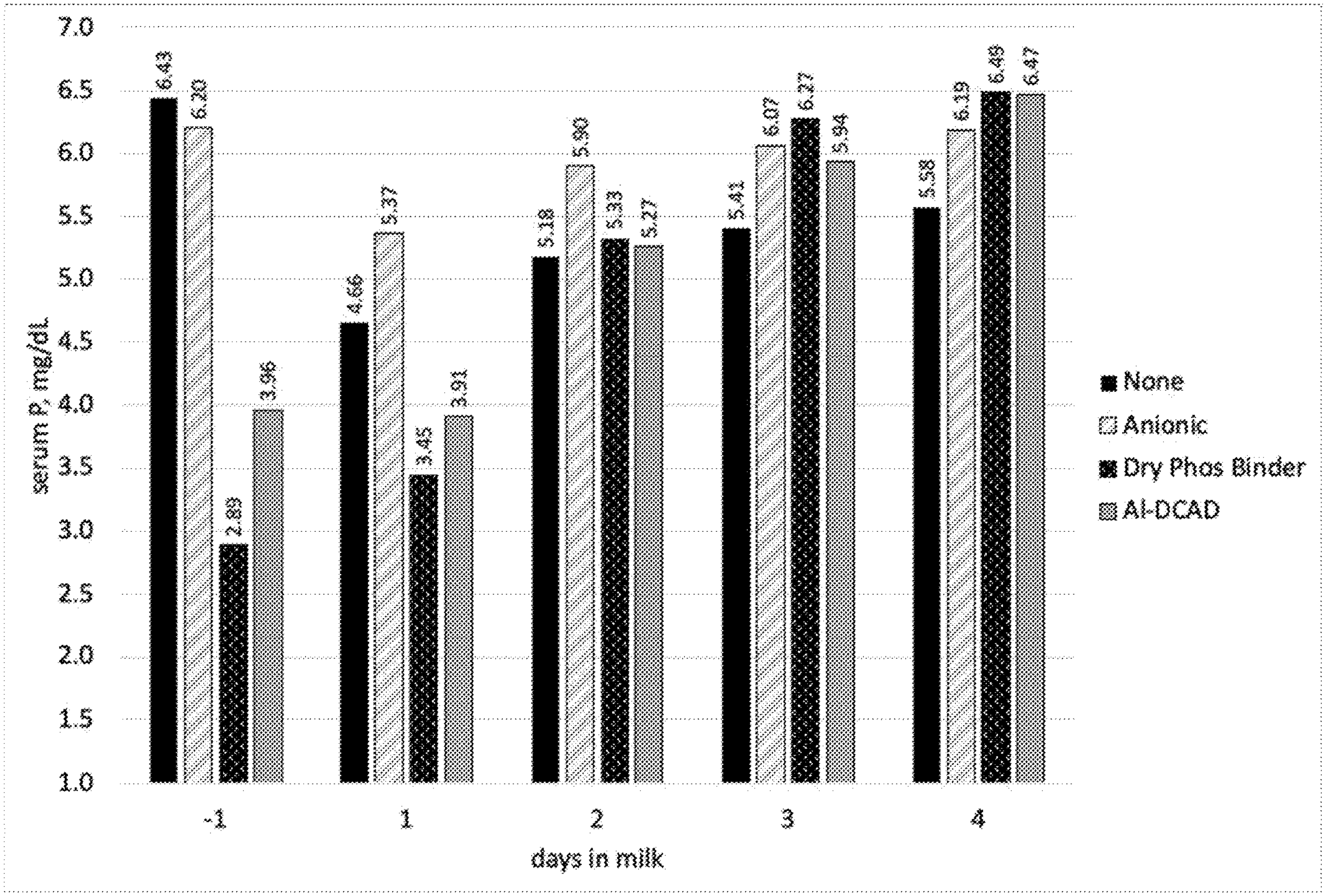

FIG. 18 is a bar chart comparing serum phosphorus levels of cows on commercial dairies among None (as a control), Anionic (aka ANI), a Dry Phos Binder, and Al-DCAD treatments across days in milk (DIM).

Figure 19:
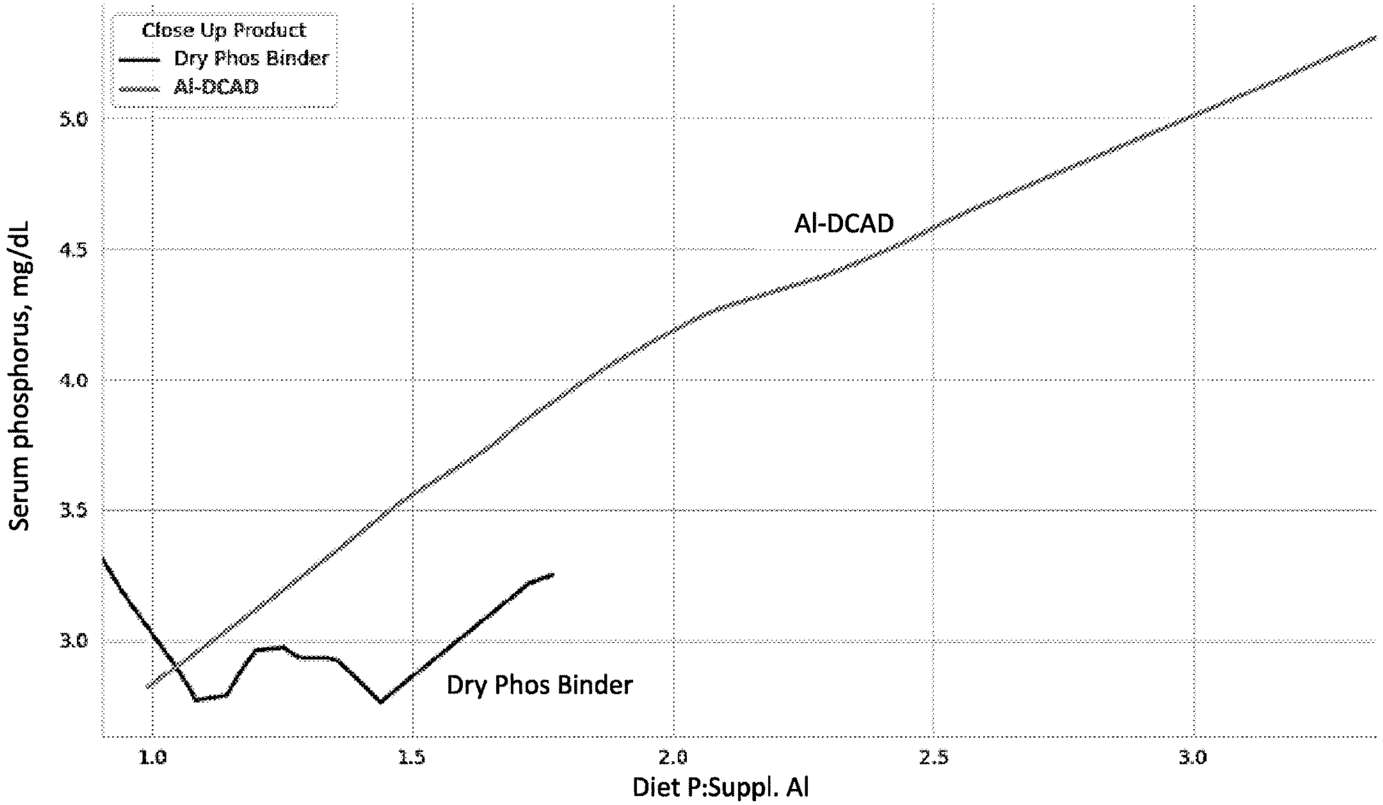

FIG. 19 is a graph comparing serum phosphorus levels versus diet phosphorus-to-aluminum ratio for Al-DCAD and Dry Phos Binder treatments in closeup parous dry cows.

Figure 20:
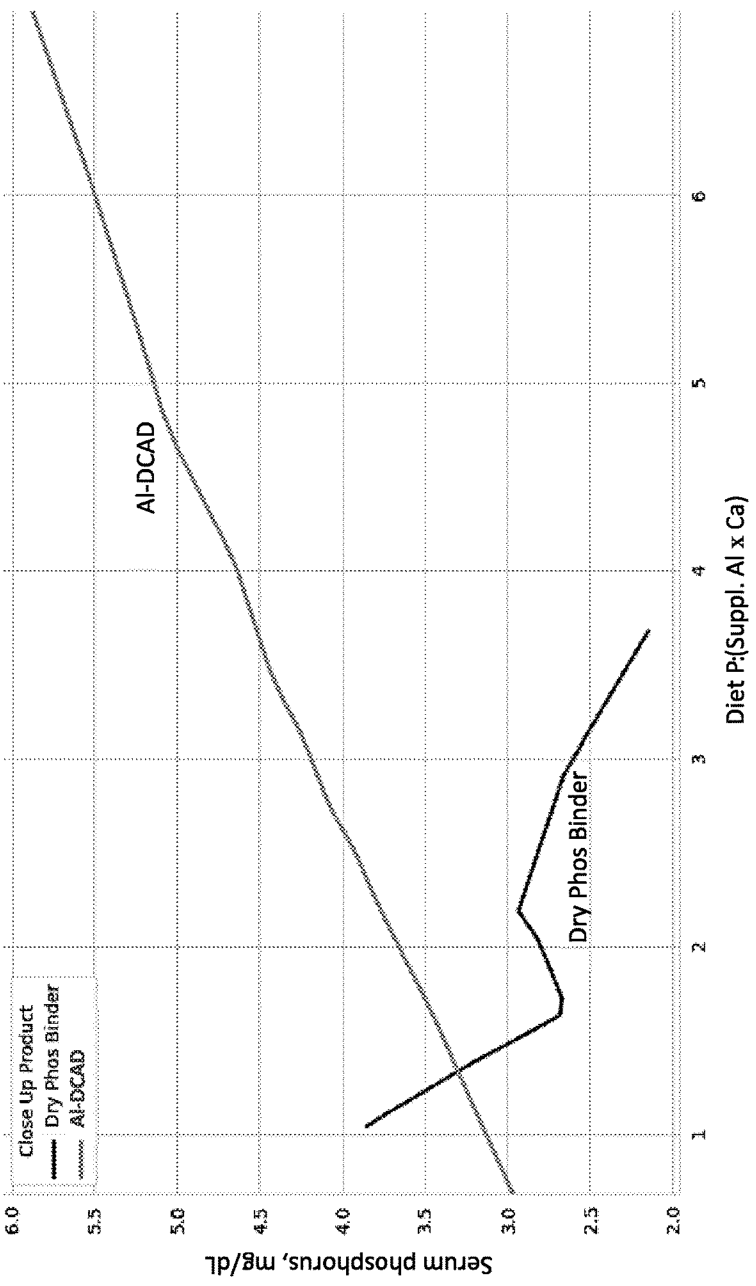

FIG. 20 is a graph comparing closeup serum phosphorus levels versus diet phosphorus-to-(aluminum multiplied by calcium) ratio for Al-DCAD and Dry Phos Binder treatments in closeup parous dry cows.

Figure 21:
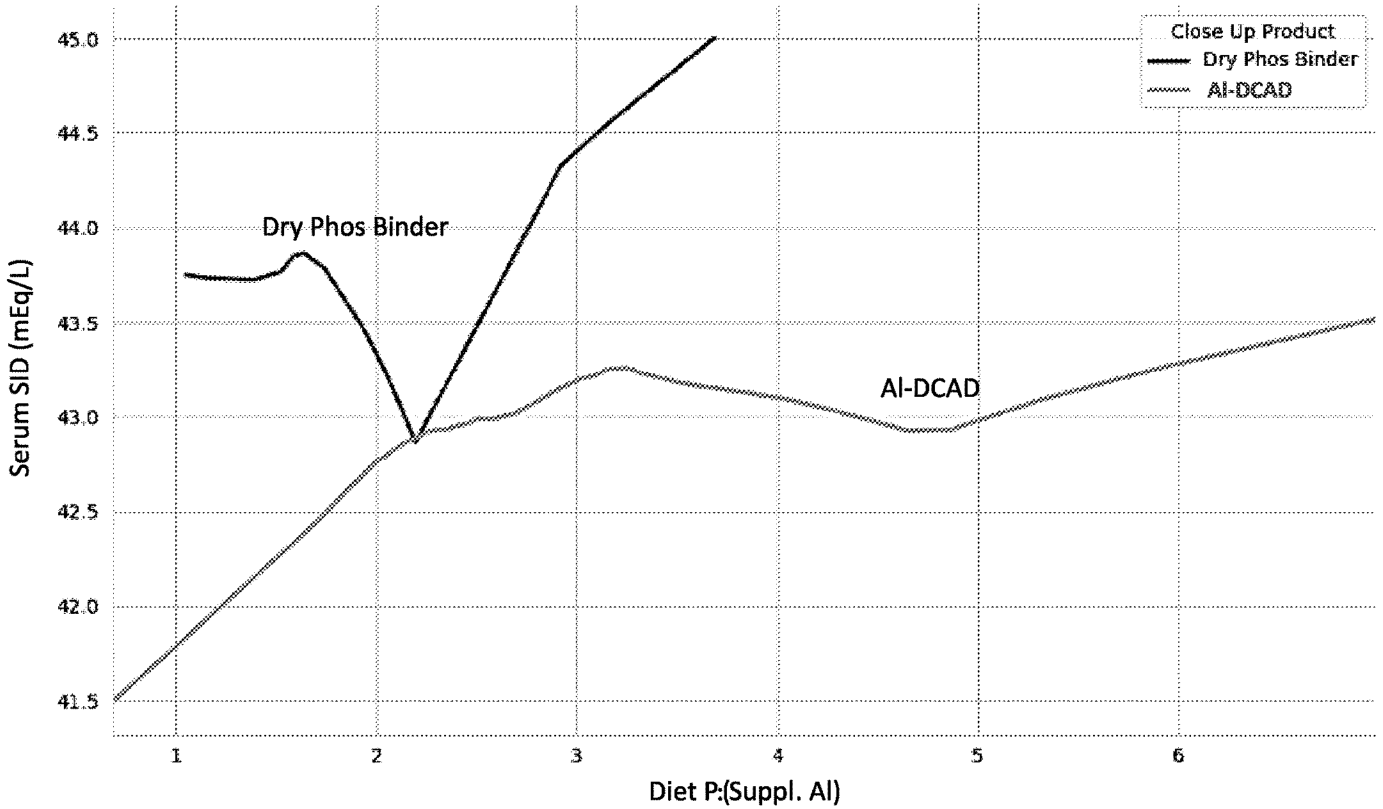

FIG. 21 is a graph comparing serum strong ion difference (SID) levels versus dietary phosphorus-to-aluminum ratio for Al-DCAD and Dry Phos Binder treatments in closeup parous dry cows.

Figure 22:
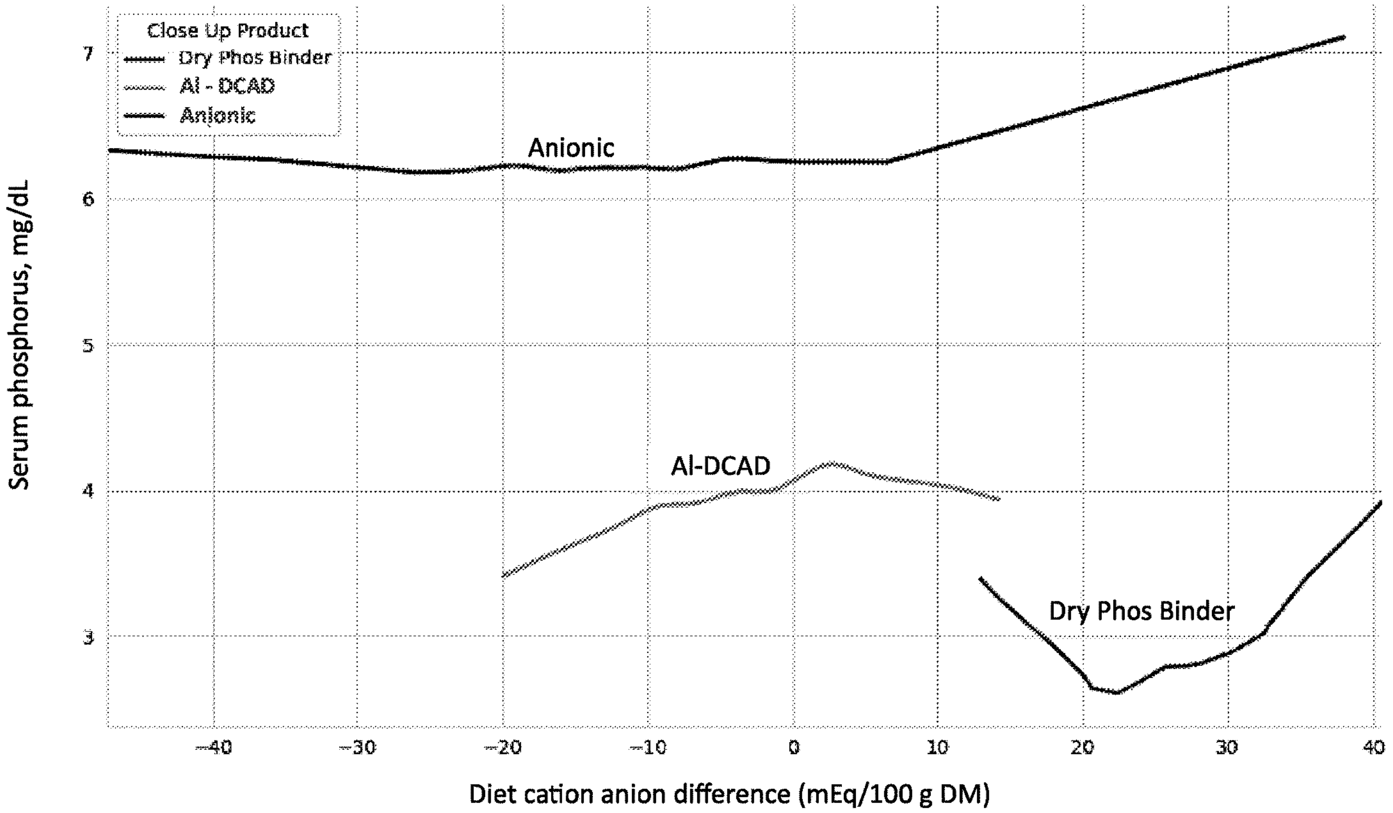

FIG. 22 is a graph comparing serum phosphorus levels versus DCAD (dietary cation-anion difference) for Anionic (aka ANI), Dry Phos Binder, and Al-DCAD treatments in closeup parous dry cows.

Figure 23:
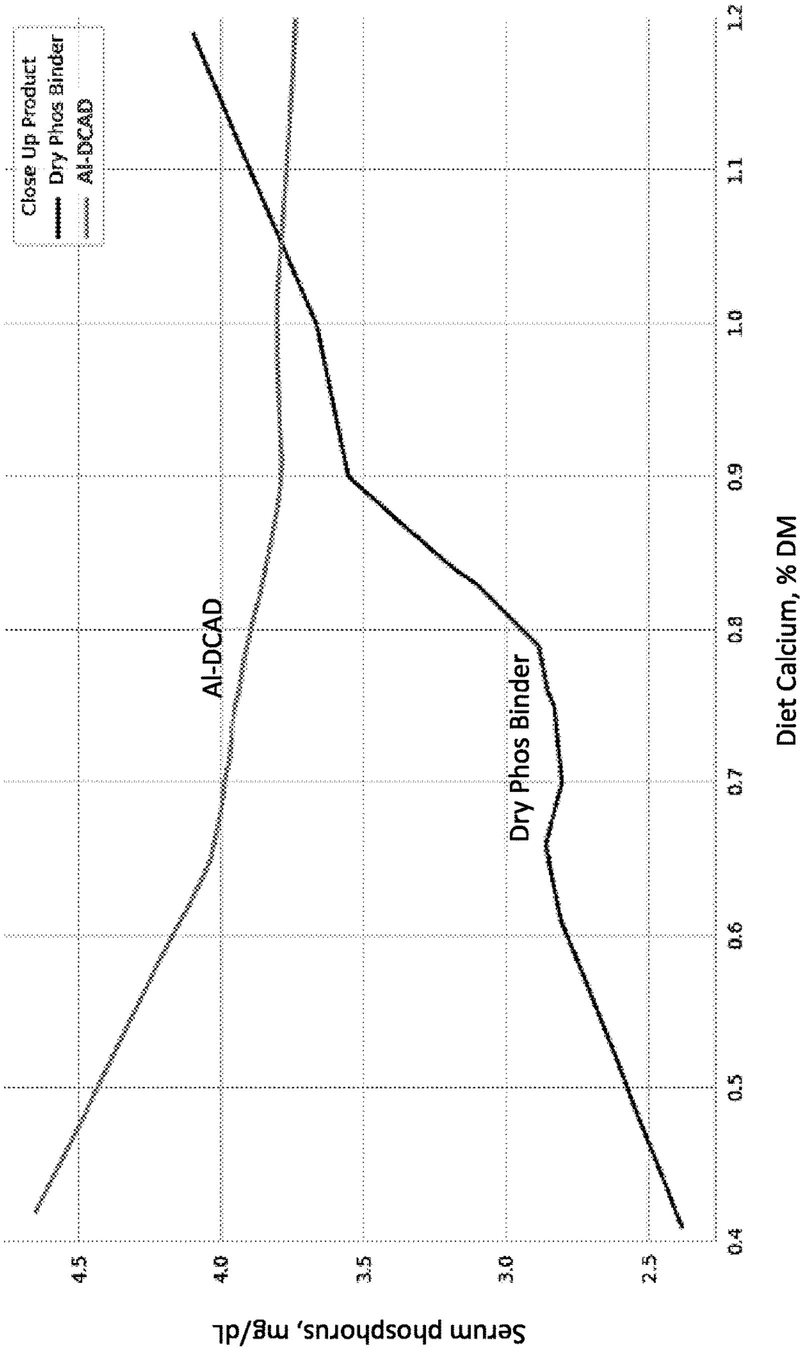

FIG. 23 is a graph comparing serum phosphorus levels versus dietary calcium percentage for Al-DCAD and Dry Phos Binder treatments in closeup parous dry cows.

Figure 24:
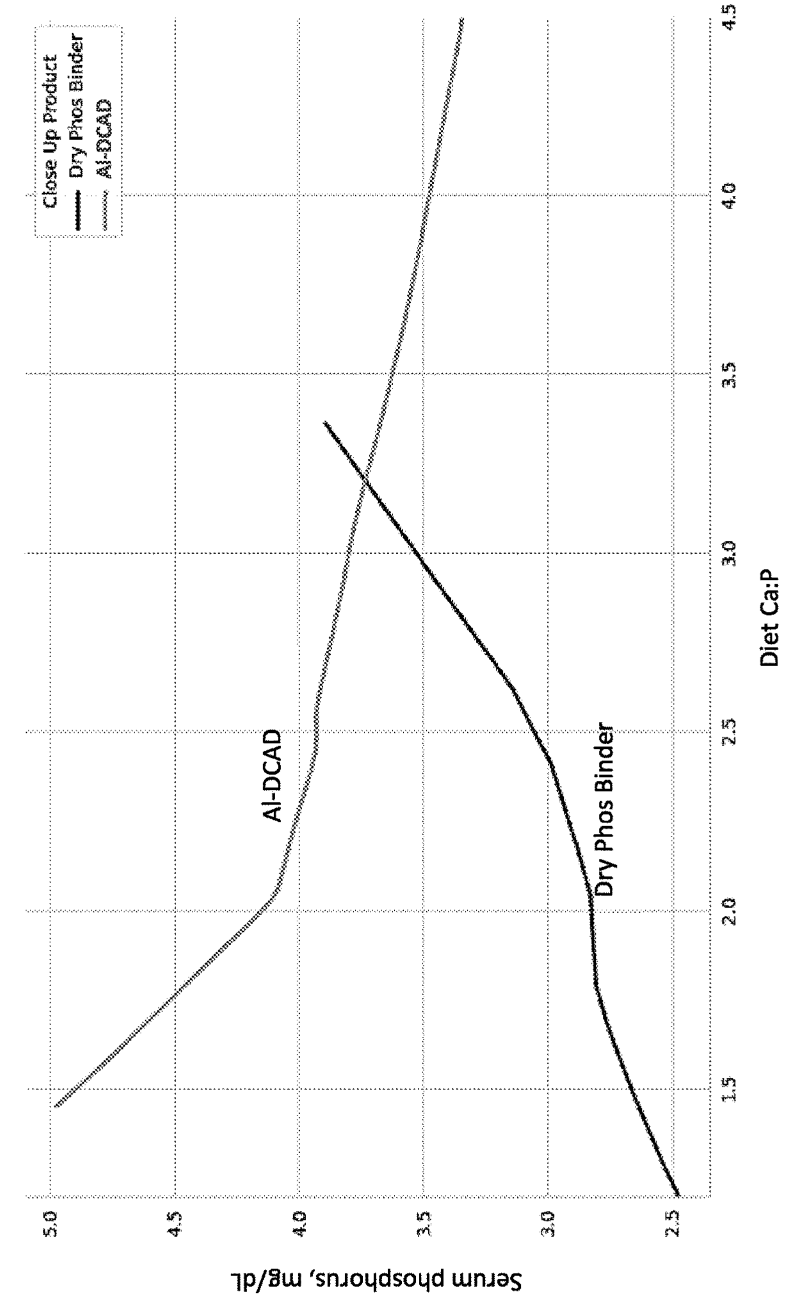

FIG. 24 is a graph comparing serum phosphorus levels versus dietary calcium-to-phosphorus ratio for Al-DCAD and Dry Phos Binder treatments in closeup parous dry cows.

Figure 25:
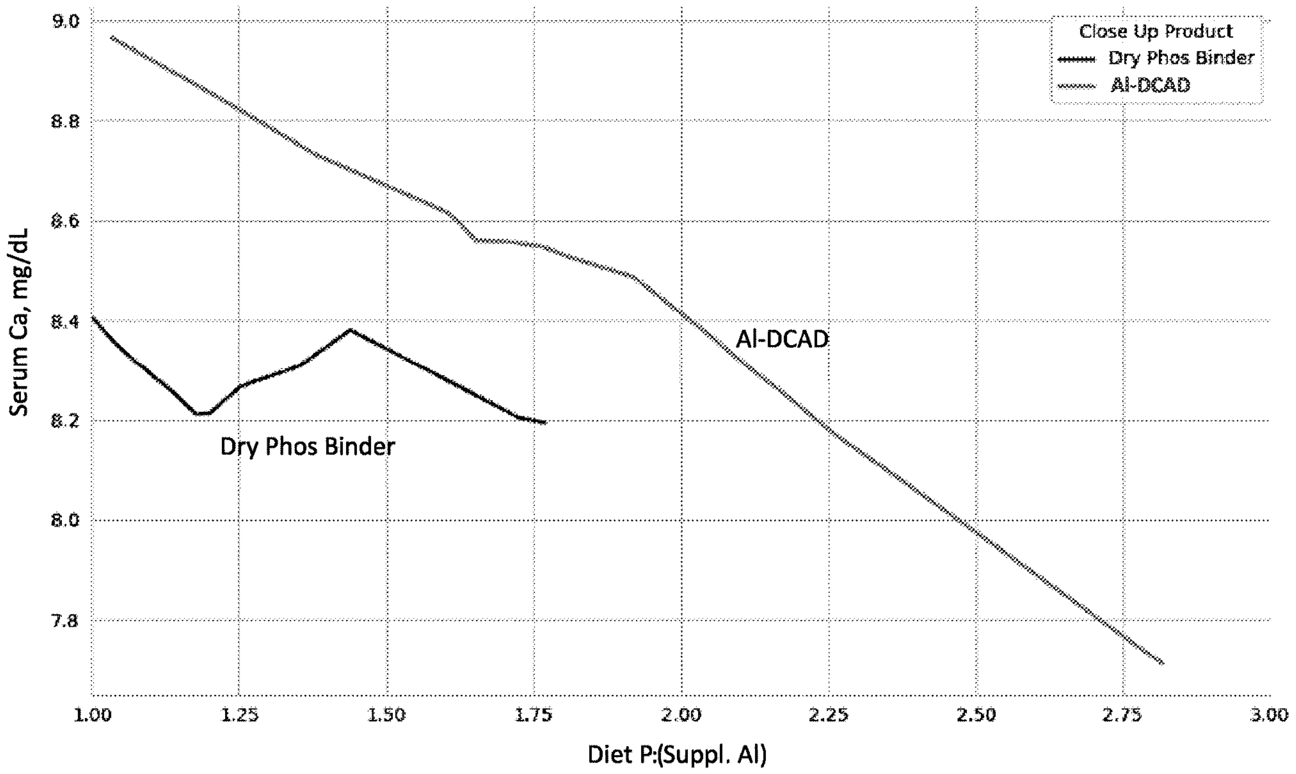

FIG. 25 is a graph comparing serum calcium levels at 1-2 days in milk (DIM) versus dietary phosphorus-to-aluminum ratio for Al-DCAD and Dry Phos Binder treatments in multiparous cows.

Figure 26:
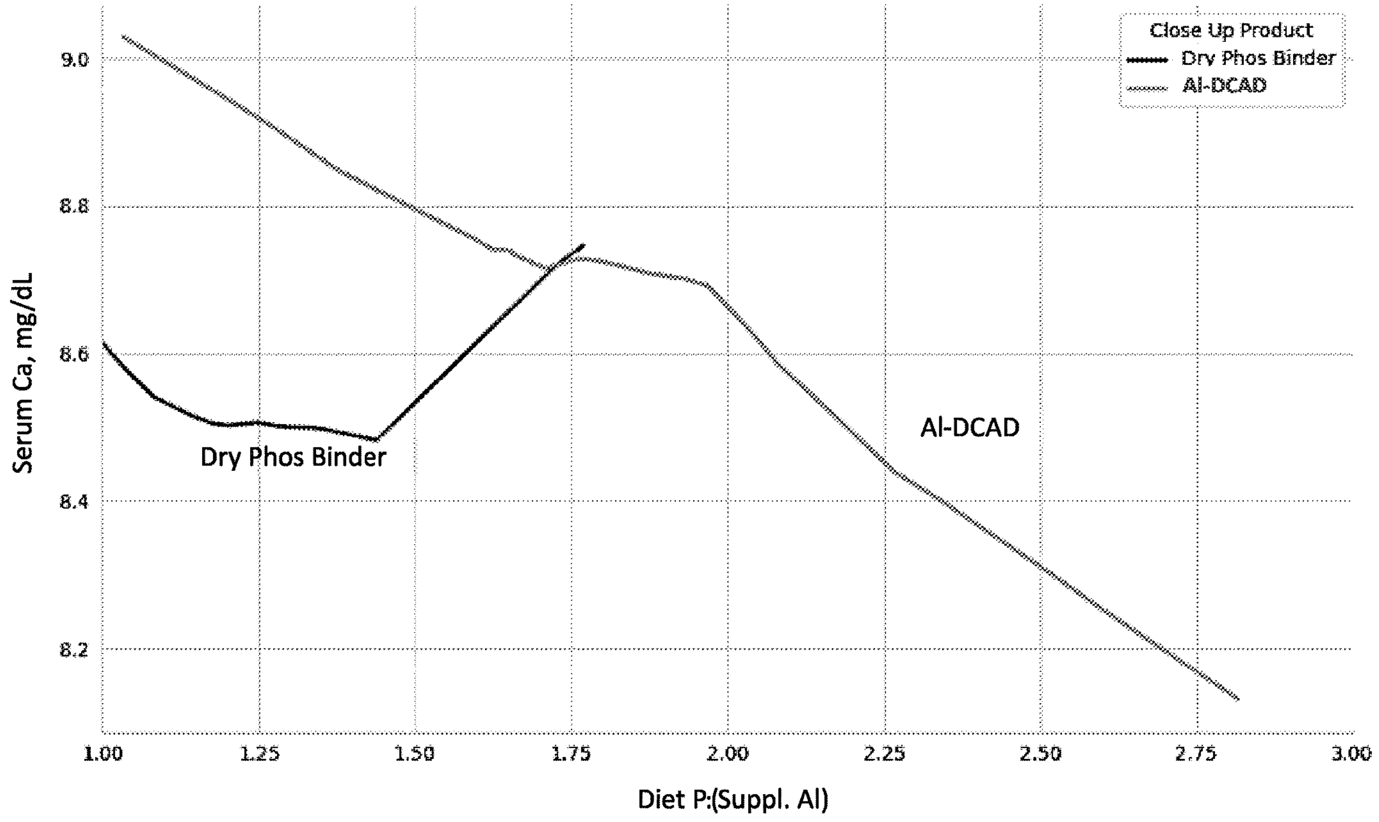

FIG. 26 is a graph comparing serum calcium levels at 1-4 days in milk (DIM) versus dietary phosphorus-to-aluminum ratio for Al-DCAD and Dry Phos Binder treatments in multiparous cows.

Figure 27:
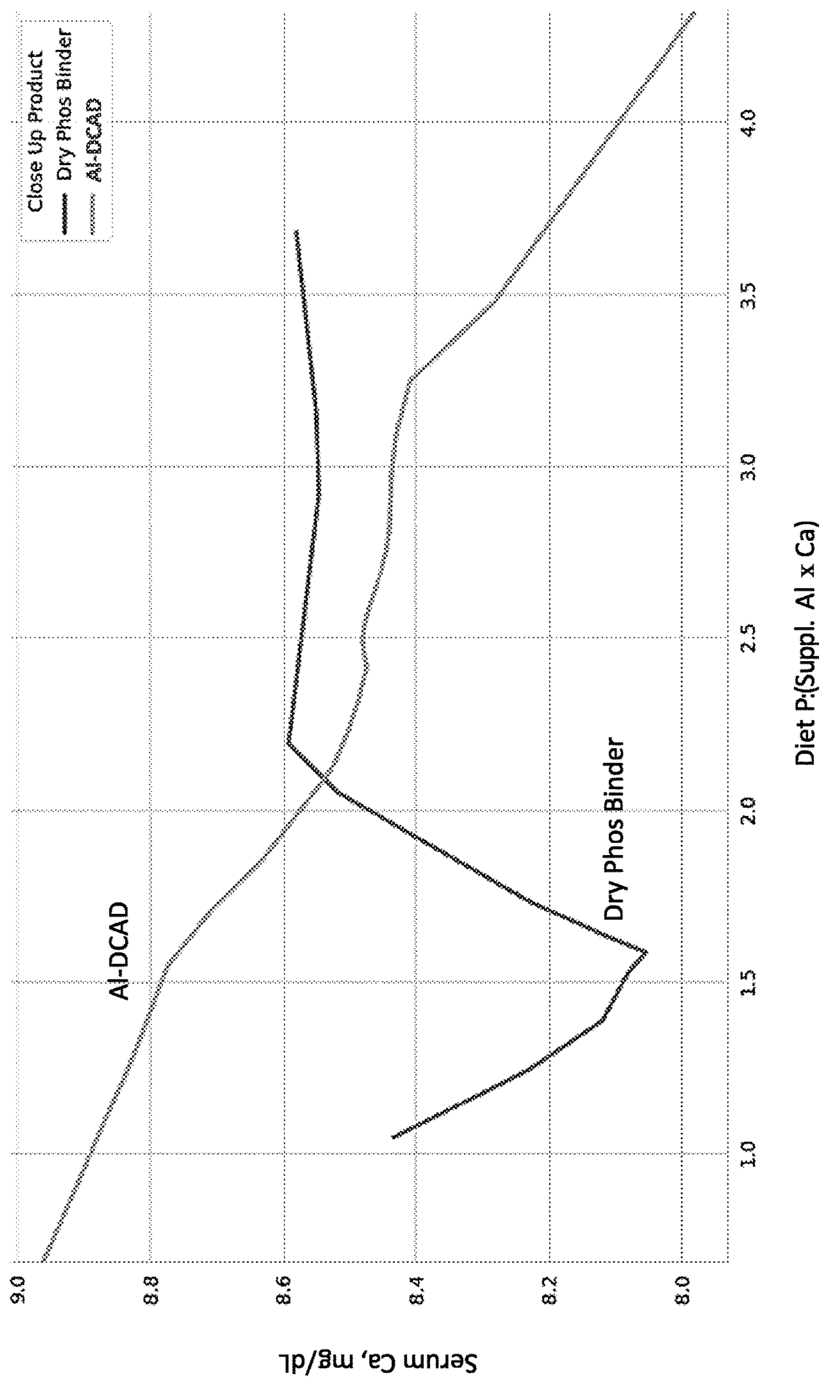

FIG. 27 is a graph comparing serum calcium levels at 1-2 days in milk (DIM) versus dietary phosphorus-to-(aluminum multiplied by calcium) ratio for Al-DCAD and Dry Phos Binder treatments in multiparous cows.

Figure 28:
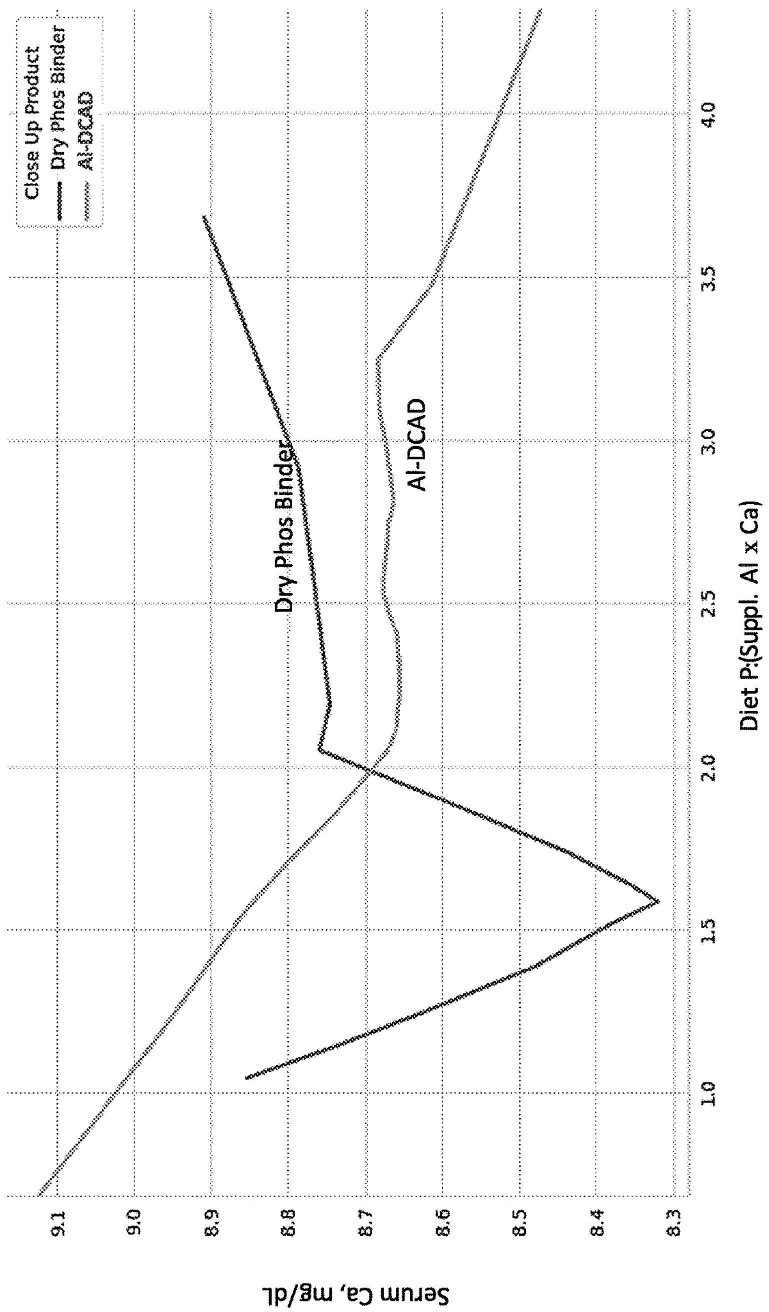

FIG. 28 is a graph comparing serum calcium levels at 1-4 days in milk (DIM) versus dietary phosphorus-to-(aluminum multiplied by calcium) ratio for Al-DCAD and Dry Phos Binder treatments in multiparous dry cows.

Figure 29:
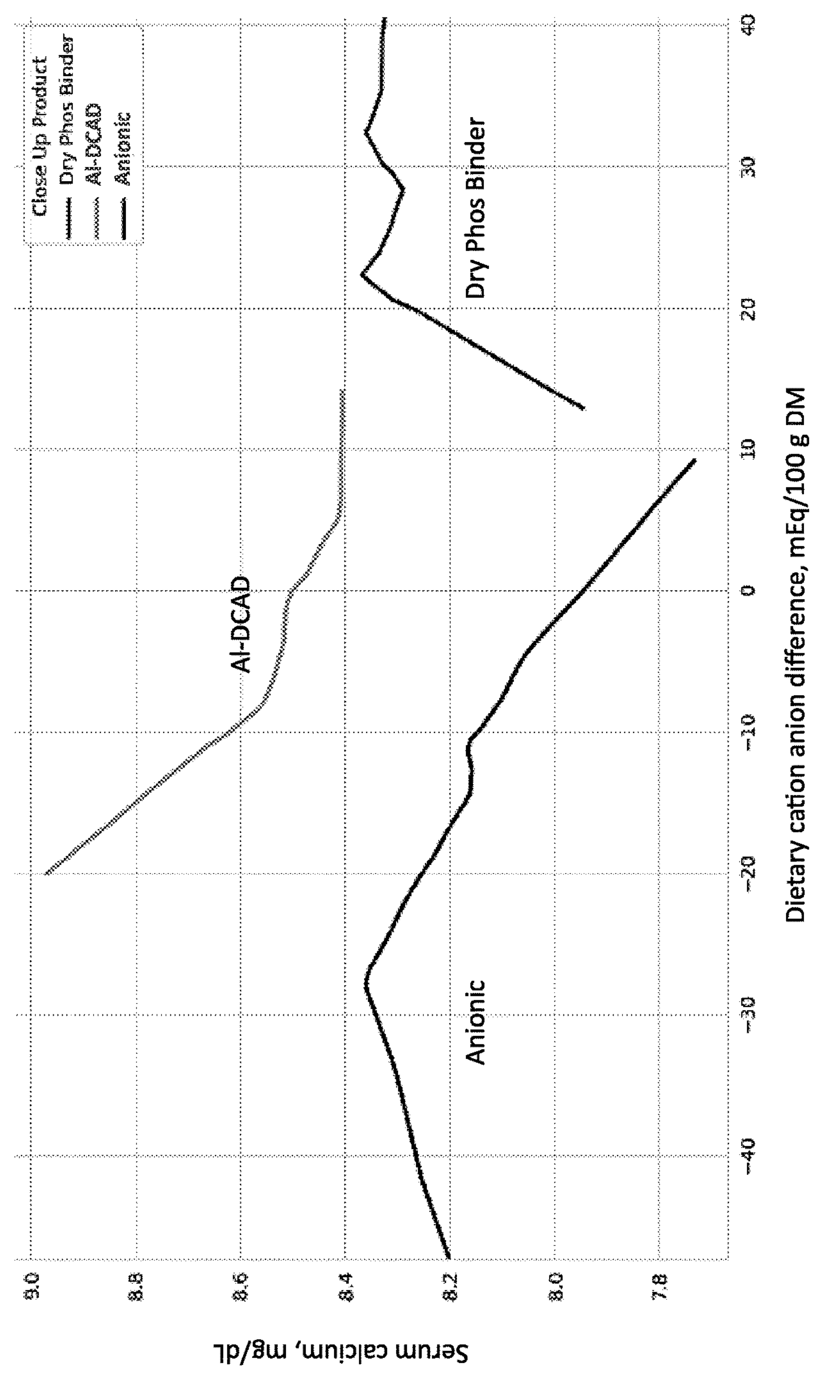

FIG. 29 is a graph comparing the effect of dietary cation-anion difference (DCAD) on serum calcium at 1-2 days in milk (DIM) for Anionic (aka ANI), Dry Phos Binder, and Al-DCAD treatments in multiparous cows.

Figure 30:
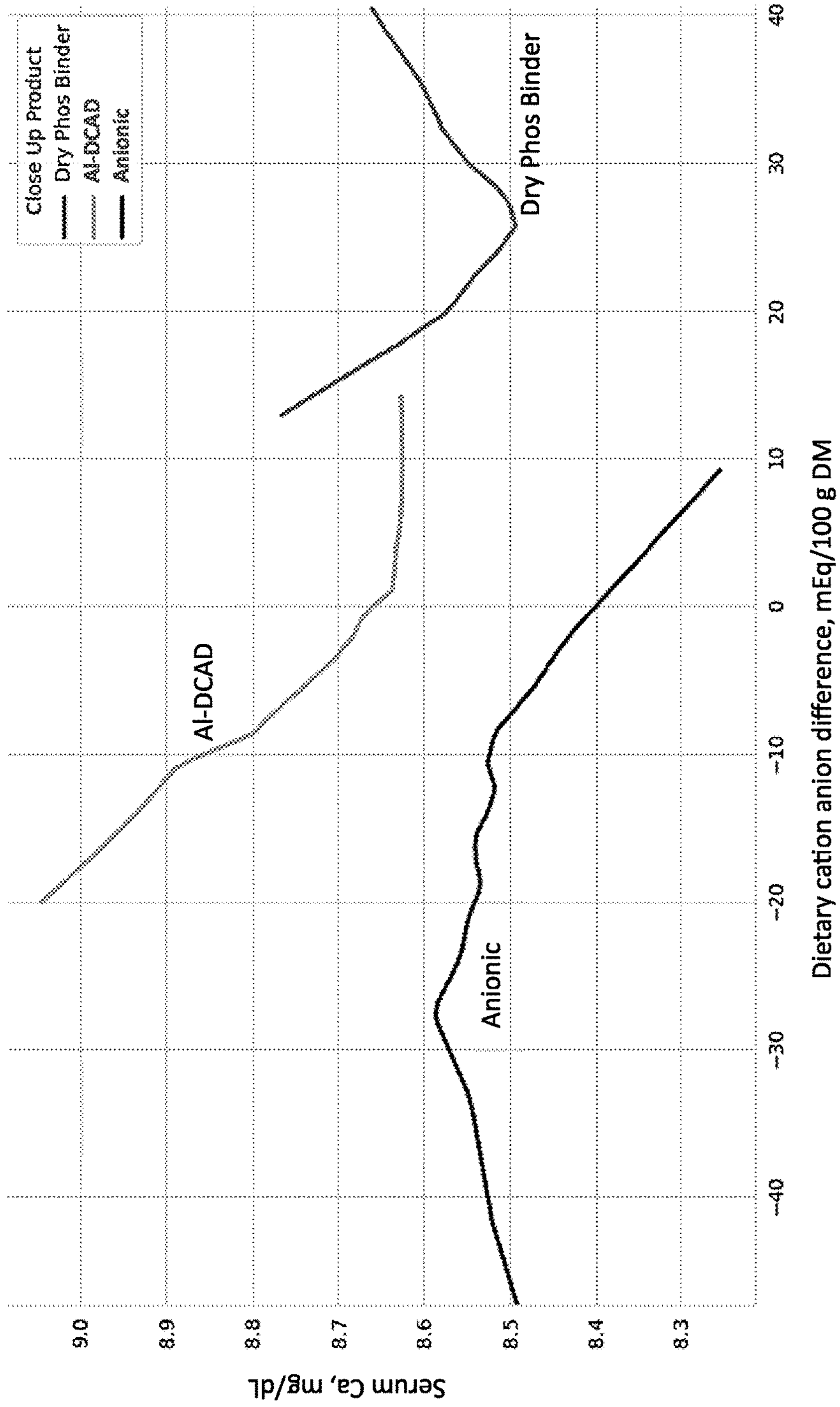

FIG. 30 is a graph comparing the effect of dietary cation-anion difference (DCAD) on serum calcium at 1-4 days in milk (DIM) for Anionic (aka ANI), Dry Phos Binder, and Al-DCAD treatments in multiparous cows.

FIG. 31 A-C are graphs showing milk fever incidence by month for multiparous cows across 3 different dairies (A, B, and C).

Figure 32:
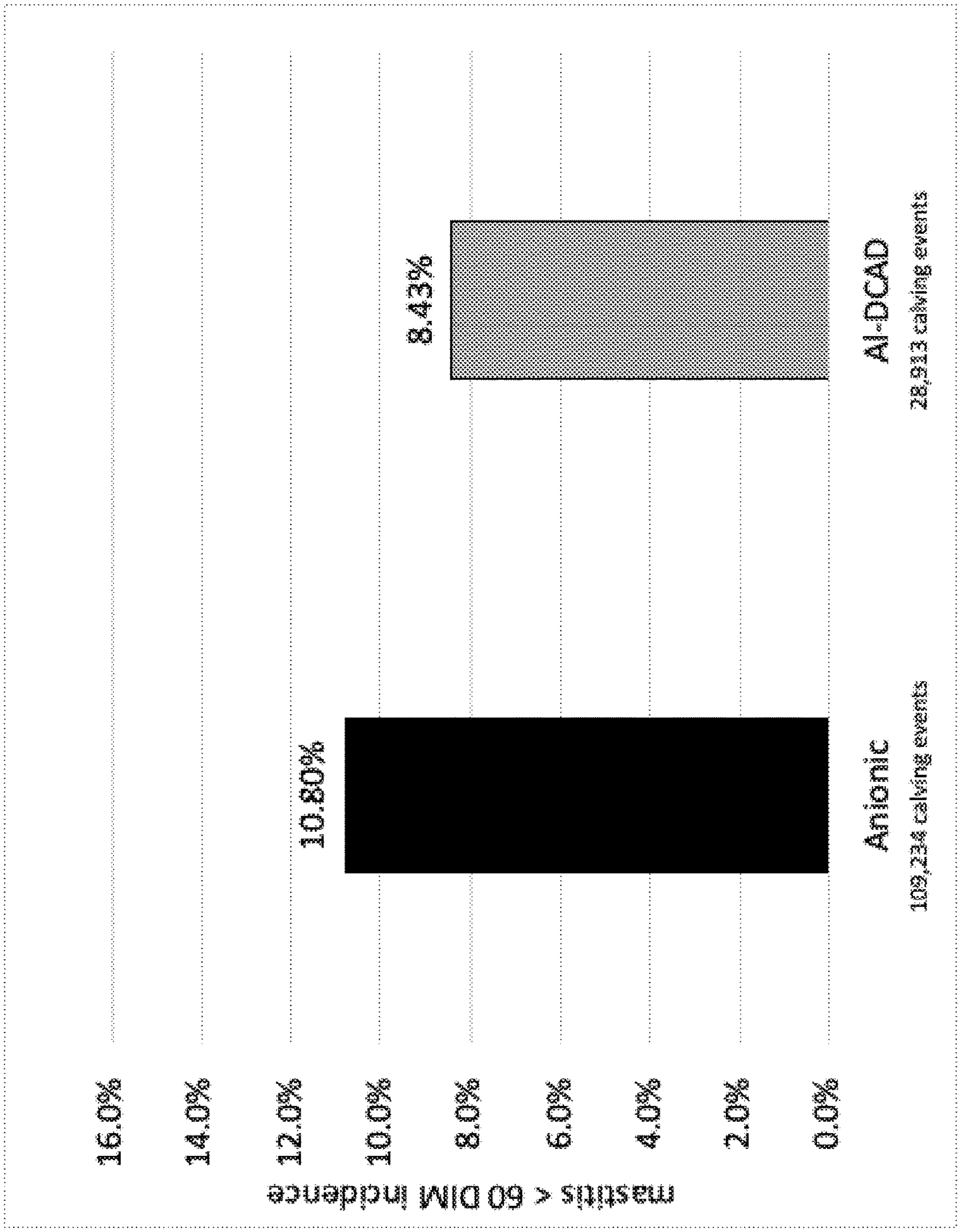

FIG. 32 is a bar chart comparing mastitis incidence in multiparous cows less than 60 days in milk (DIM) after switching from Anionic (aka ANI) to Al-DCAD treatments.

Figure 33:
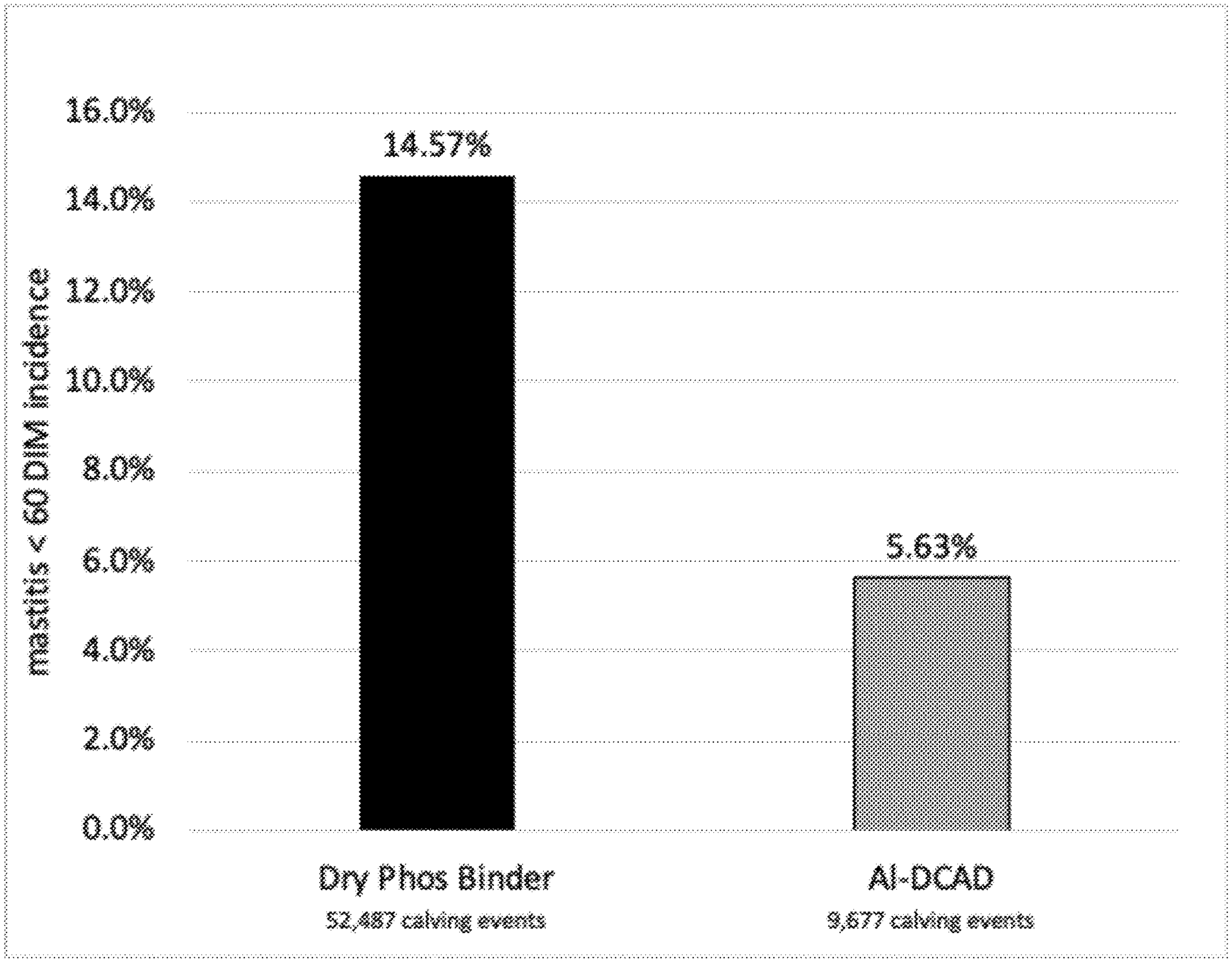

FIG. 33 is a bar chart showing mastitis incidence in multiparous cows less than 60 days in milk (DIM) after switching from Dry Phos Binder to Al-DCAD treatments.

Figure 34:
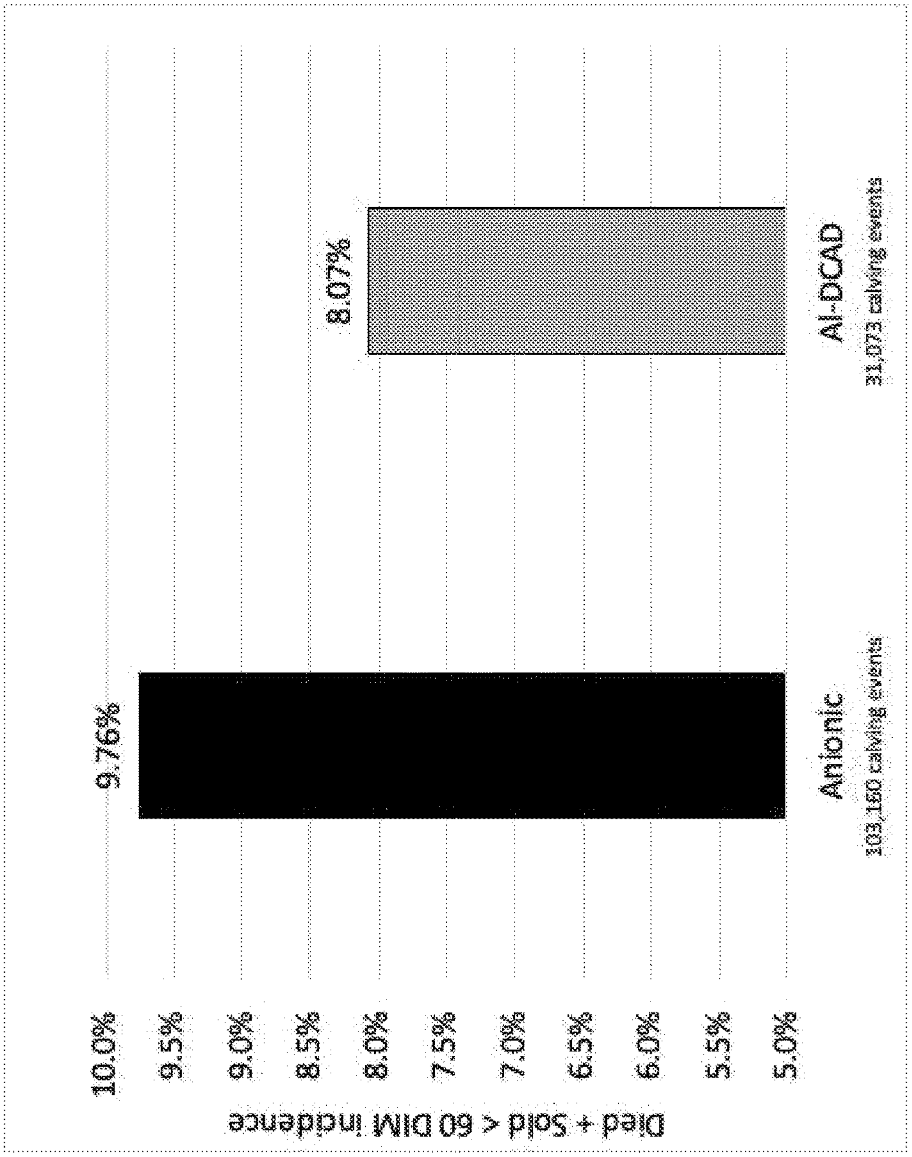

FIG. 34 is a bar chart comparing died and sold rates for multiparous cows less than 60 days in milk (DIM) after switching from Anionic to Al-DCAD treatments.

Figure 35:
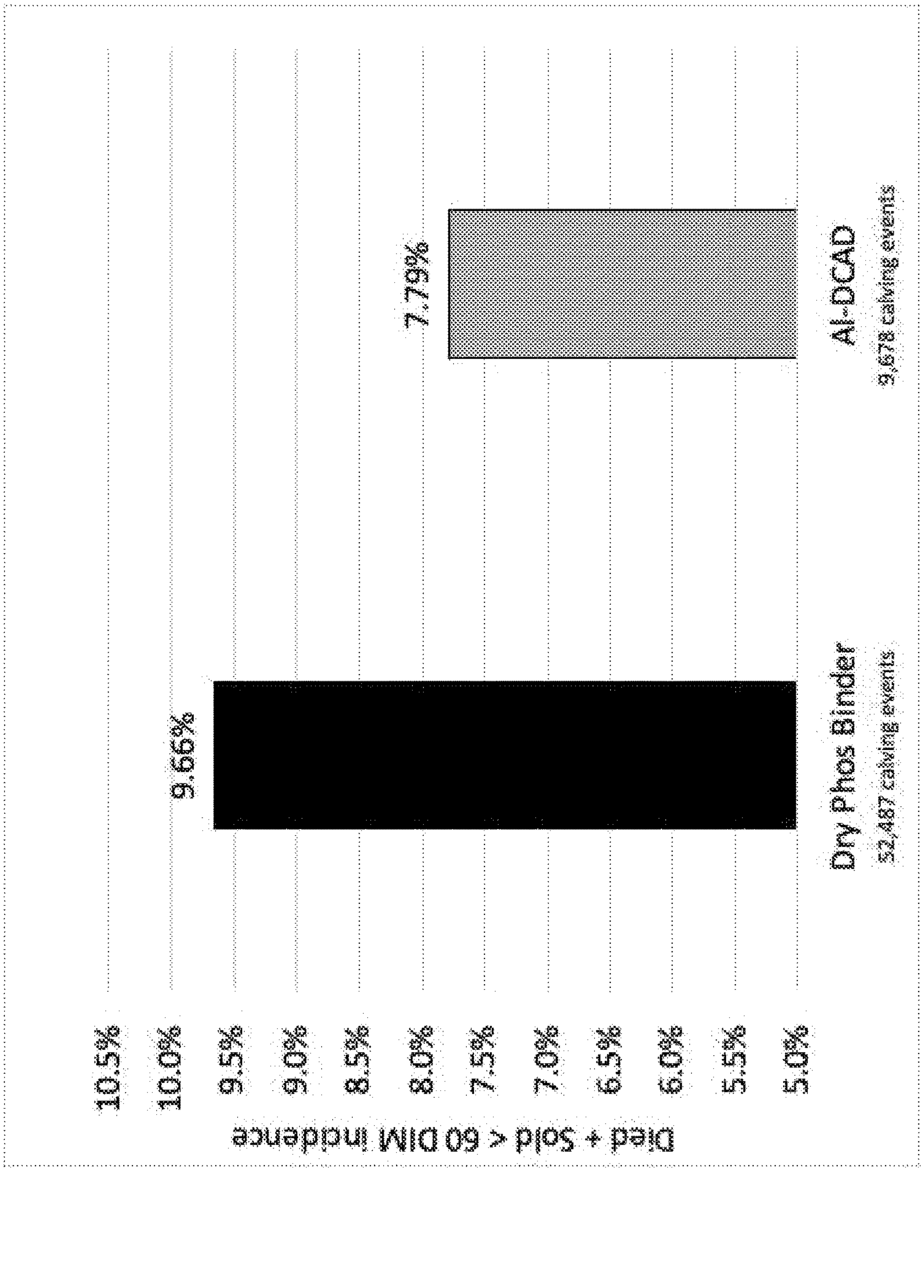

FIG. 35 is a bar chart comparing died and sold rates for multiparous cows less than 60 days in milk after switching from Dry Phos Binder to Al-DCAD treatments.

Figure 36:
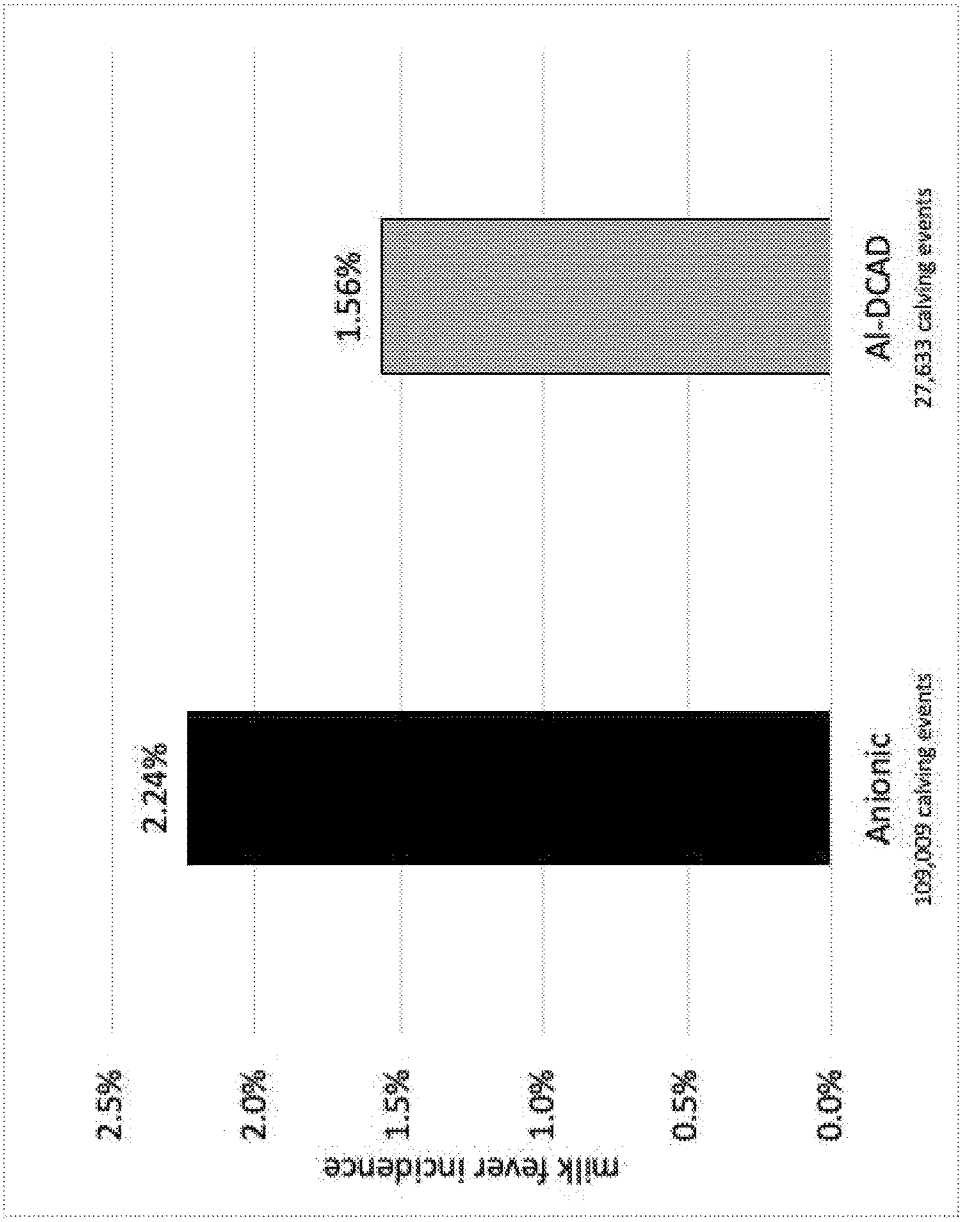

FIG. 36 is a bar chart comparing milk fever incidence rates for multiparous cows after switching from Anionic (aka ANI) to Al-DCAD treatments.

Figure 37:
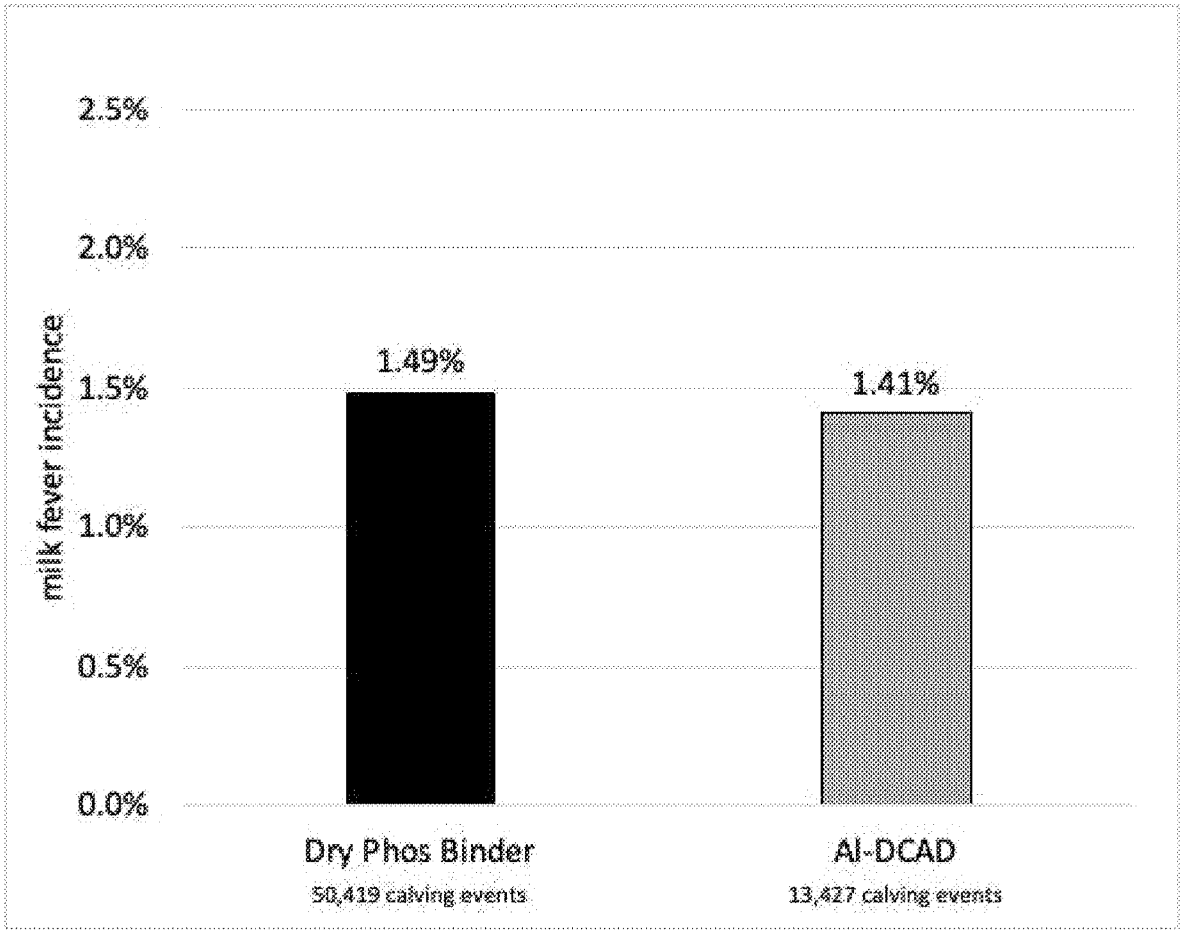

FIG. 37 is a bar chart comparing milk fever incidence rates for multiparous cows after switching from Dry Phos Binder to Al-DCAD treatments.

Figure 38:
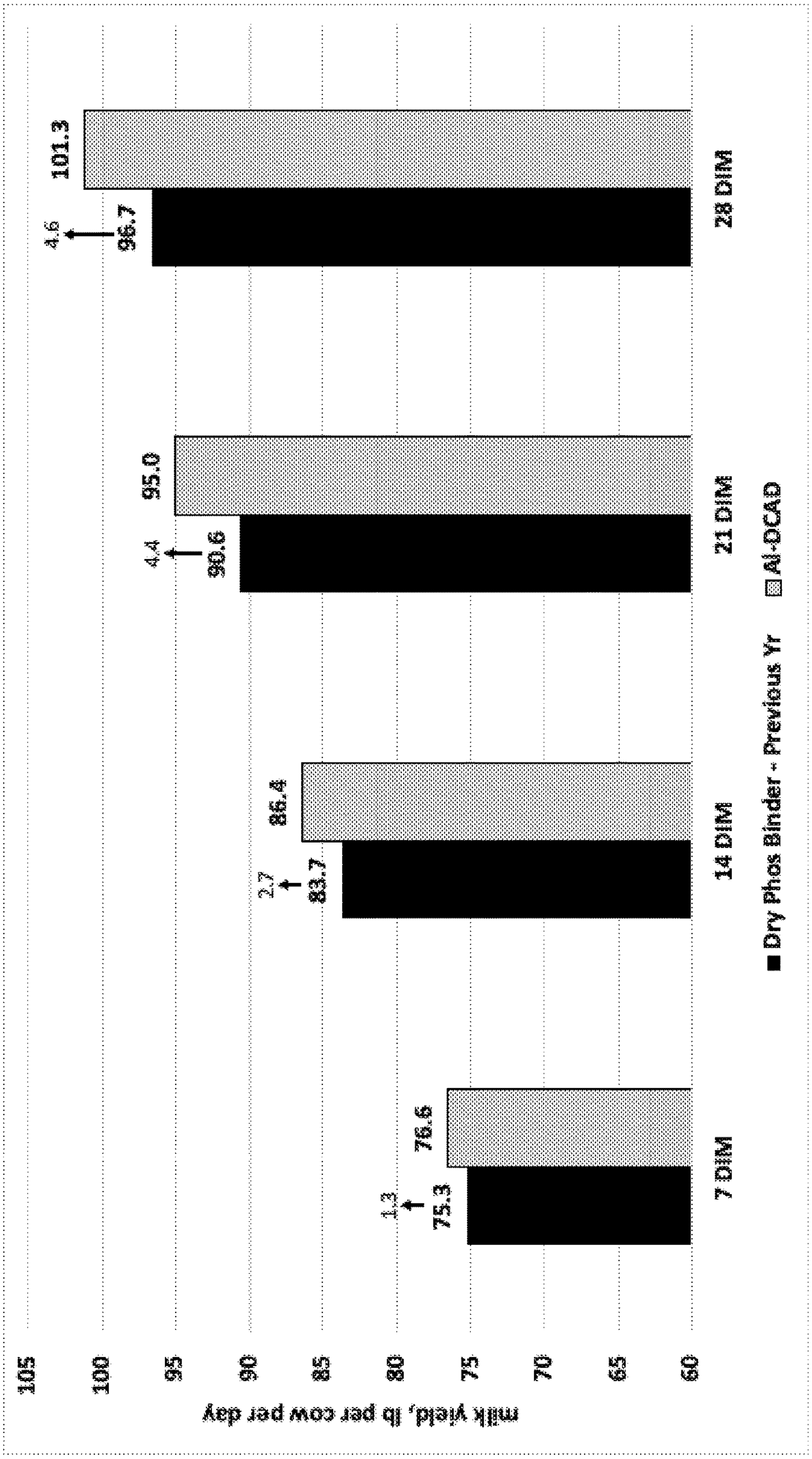

FIG. 38 is a bar chart comparing daily milk yield by day in multiparous cows after switching from Dry Phos Binder to Al-DCAD treatments.

Figure 39:
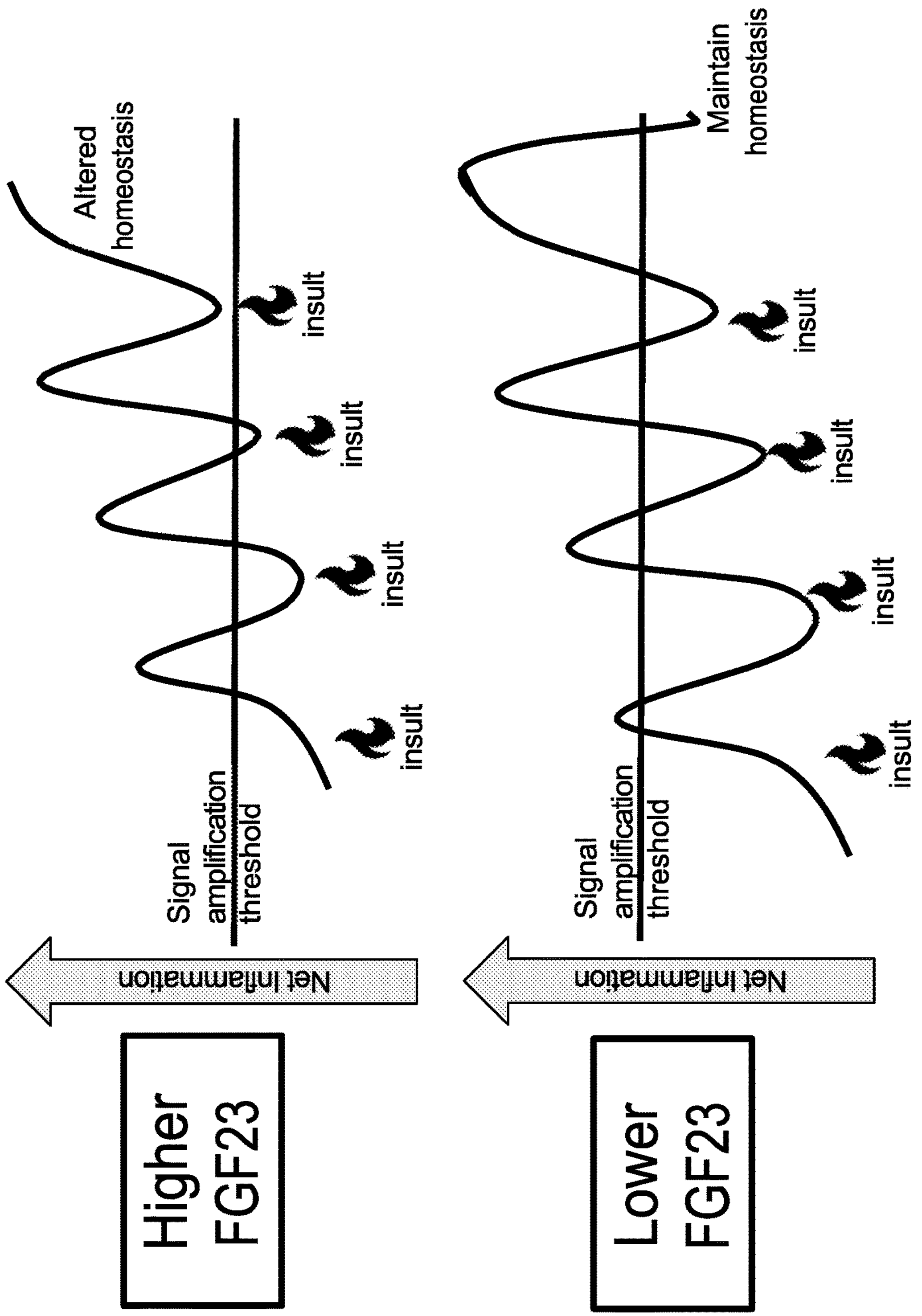

FIG. 39 is an illustration graphing the effects of lower or higher fibroblast growth factor 23 (FGF23) on inflammation and homeostasis in dairy cows.

Figure 40:
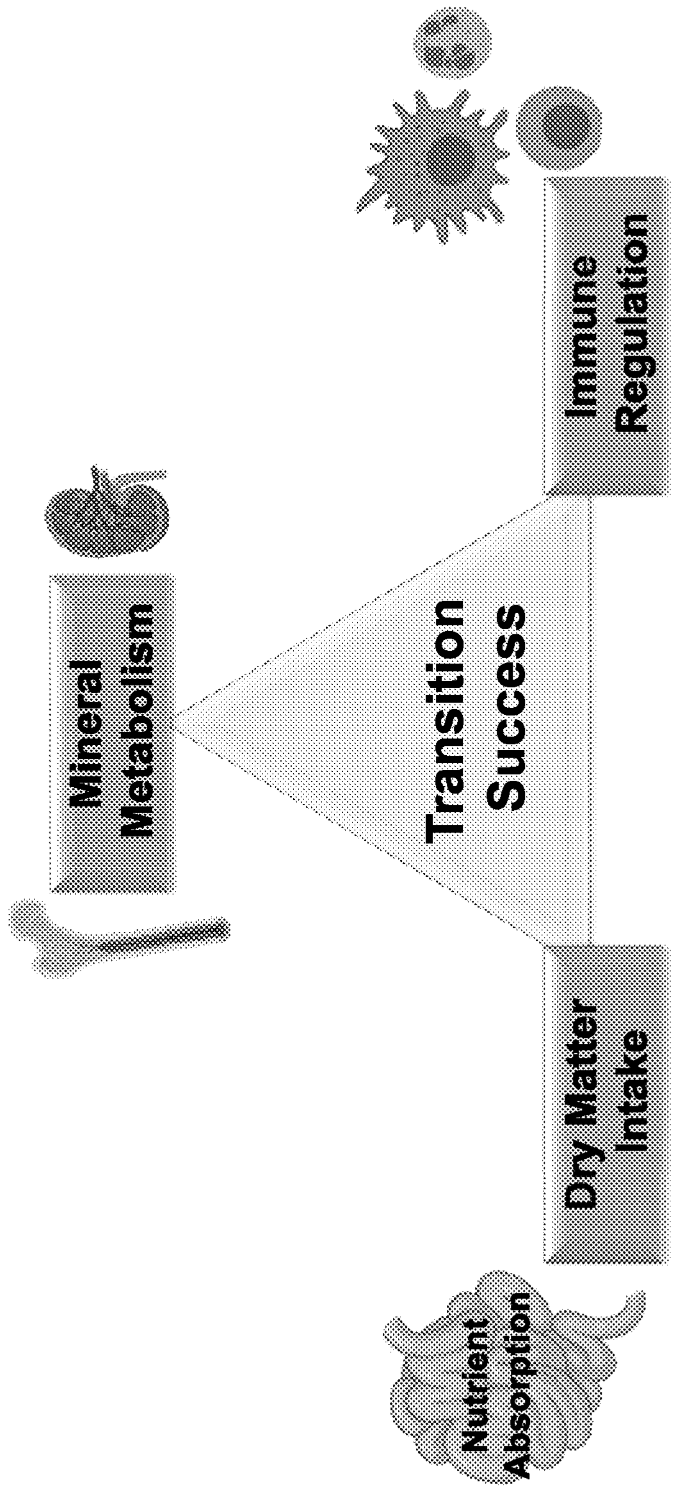

FIG. 40 is a diagram linking dry matter intake and nutrient absorption, mineral metabolism, and immune regulation to transition success in dairy cows.

DETAILED DESCRIPTION AND EXAMPLES

Introduction

The disclosure will be described by referring to the general conditions for the process and to examples of how it can be made and used.

Hypocalcemia and milk fever are costly challenges in dairy cows after parturition. Milk Fever tends to only affect multiparous cows.

There has been a long-felt need for improved total dietary compositions for prepartum dairy cows that effectively manage both phosphorus binding and Dietary Cation-Anion Difference (DCAD) to reduce hypocalcemia and support metabolic health without toxicity or nutritional compromises.

Effects of High Dietary Phosphorus on Serum Phosphorus and Calcium

To address these challenges, it is helpful to first understand the underlying metabolic pathways, beginning with the role of calcium homeostasis and the impact of dietary factors such as phosphorus on serum levels in prepartum cows.

FIG. 1 is a schematic diagram illustrating calcium metabolism and regulation in a cow, showing interactions involving blood pH, PTH (parathyroid hormone), vitamin D derivatives, gut absorption, renal excretion, bone resorption, and mammary uptake.

A serum Ca drop stimulates Parathyroid Hormone (PTH) secretion. PTH then acts on bone cells to stimulate bone Ca mobilization. PTH also acts on the kidney, stimulating the conversion of 25-hydroxyvitamin D to the active form of vitamin D, also known as 1.25 $(OH)_2$ $D_3$. The active form of vitamin D increases Ca absorption from the intestine and increases Ca mobilization from the animal's bone. Reducing blood (serum) pH by feeding a low or negative DCAD diet before calving increases the sensitivity of the receptors for PTH and improves Ca status around parturition.

FIG. 2 is a graph showing a direct positive association between dietary phosphorus percentage and serum phosphorus levels in closeup prepartum cows based on field data.

As dietary phosphorus increases in prepartum cows, serum P concentration increases as well. Normal serum phosphorus for cows is in the range of 4.0 to 8.0 mg/dL. Satter, L. 2002. What Goes In Must Come Out: Phosphorus Balance on Dairy Farms. American Association of Bovine Practitioners Conference Proceedings 125-130.

While lower serum phosphorus is desirable, it is also desirable to not push the serum phosphorus unnecessarily low below 3.6 mg/dL.

FIG. 3 is a graph showing an inverse association between dietary phosphorus percentage and serum calcium levels in closeup prepartum cows based on field data.

As dietary phosphorus increases in prepartum cows, serum Ca concentration decreases. This indicates that the amount of P absorbed by the cow impacts Ca metabolism. Peterson et al (2005) found that incidence of subclinical hypocalcemia was 50, 69 and 75% for cows fed 0.21, 0.31 and 0.44% dietary P prepartum, respectively. Peterson, A. B., M. W. Orth, J. P. Goff, and D. K. Beede. 2005. Periparturient Responses of Multiparous Holstein Cows Fed Different Dietary Phosphorus Concentrations Prepartum. Journal of Dairy Science 88:3582-3594.

Reducing the dietary phosphorus in prepartum cows to 0.16% of the diet on a dry matter basis reduces the serum P before calving and increases plasma total Ca before and after parturition. This suggest that managing dietary P prepartum can be used as a tool to improve Ca status in dairy cows See Wächter, S., I. Cohrs, L. Golbeck, T. Scheu, K. Eder, and W. Grünberg. 2022a. Effects of restricted dietary phosphorus supply during the dry period on productivity and metabolism in dairy cows. Journal of Dairy Science 105:4370-4392.

However, phosphorus in the basal diet for dairy cows is typically in the range of about 0.25% to about 0.60% on a dry matter basis. It is difficult to reduce the amount of phosphorus in the basal diet, which is typically only done for experimental purposes.

Manipulation of dietary Ca with prepartum DCAD has been studied extensively. Conclusions among studies varied but it is common to find DCAD diets in the field with levels of dietary Ca ranging from 0.5% to 1.8%. Industry recommendations when feeding a Dry Phos Binder suggest being below 0.6%.

The typical range for dietary Ca is 0.5% to 1.8% for DCAD diets, 0.7-0.95% for Al-DCAD, and <0.65% Dry Phos binders.

Hypothesis Linking FGF23 Hormone to Inflammation and Mineral Metabolism

While manipulating dietary calcium and phosphorus levels offers some control over mineral balance, emerging research points to the hormone FGF23 as an important regulator linking these elements to inflammation and immune function, providing a hypothesis for contributing metabolic disruptions in transition cows and cows during the early postpartum period.

FIG. 4 is a schematic diagram illustrating phosphorus metabolism and regulation in a cow, showing interactions involving blood (serum) phosphorus, PTH (parathyroid hormone), fibroblast growth factor 23 (FGF23), vitamin D derivatives, bone turnover, gut absorption, and urine excretion.

High dietary phosphorus increases blood (serum) P. Higher blood phosphorus increases production of FGF23, a regulatory hormone, which reduces bone turnover, increases excretion of P at the kidney level, reduces conversion of active form of vitamin D at the kidney level, which reduces the active absorption of P and Ca from the gastrointestinal tract. Limiting bone turnover limits resorption of Ca and P from bone into bloodstream/circulation. FGF23 also reduces PTH production affecting Ca metabolism as well.

FIG. 5 is a schematic diagram showing dietary phosphorus transition in cows, including increased fibroblast growth factor 23 (FGF23) mRNA expression in bone tissue in response to inflammatory mediators.

FIG. 5 is like the description regarding FIG. 4, but in a different format and adding that high FGF23 reduces effectiveness of the immune system by reducing leukocytes recruitment and bacterial clearance in infectious challenges.

Without being limited to any theoretical explanations or hypotheses, it is hypothesized that FGF23 may be a link between inflammation and mineral status. Several animal studies support this hypothesis.

Researchers injected mice intraperitoneally with LPS or inflammatory mediators TNF-$\alpha$ and IL-$\beta$. All 3 compounds increased FGF23 production in bone, bone marrow and thymus gland. Onal, M., A. H. Carlson, J. D. Thostenson, N. A. Benkusky, M. B. Meyer, S. M. Lee, and J. W. Pike. 2018. A Novel Distal Enhancer Mediates Inflammation-, PTH-, and Early Onset Murine Kidney Disease-Induced Expression of the Mouse Fgf23 Gene. JBMR Plus 2:31-46.

In a study on neutrophil recruitment and host defense during pneumonia in mice with chronic kidney failure, it was found that recruitment of neutrophils into the bronchoalveolar lavage was reduced as levels of FGF23 were increased. They concluded that FGF23 acts directly on PMNs and dampens host defense by direct interference with chemokine signaling and integrin activation. Rossaint, J., J. Oehmichen, H. Van Aken, S. Reuter, H. J. Pavenstädt, M. Meersch, M. Unruh, and A. Zarbock. 2016. FGF23 signaling impairs neutrophil recruitment and host defense during CKD. Journal of Clinical Investigation 126:962-974.

Injection of mice with FGF23 increased levels of CRP and IL-6 in liver cells and serum CRP. Singh, S., A. Grabner, C. Yanucil, K. Schramm, B. Czaya, S. Krick, M. J. Czaja, R. Bartz, R. Abraham, G. S. Di Marco, M. Brand, M. Wolf, and C. Faul. 2016. Fibroblast growth factor 23 directly targets hepatocytes to promote inflammation in chronic kidney disease. Kidney International 90:985-996.

When osteoblast-like cells were exposed to lactic acid, it acted in a dose dependent manner inducing FGF23 gene expression and up-regulated FGF23 synthesis. Alber, J., and M. Föller. 2022. Lactic acid induces fibroblast growth factor 23 (FGF23) production in UMR106 osteoblast-like cells. Mol Cell Biochem 477:363-370.

These four studies discussed above demonstrate that FGF23 has some impact on the immune system and that it appears to modulate some of the inflammatory signaling and response in a mammal.

FGF23 is a potential marker for human patient outcomes during critical illness. Mortality rates for individuals entering intensive care units increased from 26% to 56% for patients with low or high FGF23 levels in blood at day 0, respectively. FGF23 has been associated not only with P and Ca metabolism but with inflammatory immune responses. At least in humans, higher FGF23 levels have been associated with susceptibility to infections, sepsis and mortality, especially in clinical kidney disease patients that have high serum phosphorus. It appears that by reducing/managing the concentration of FGF23 in blood by controlling the amount of phosphorus that can be absorbed from the diet may influence the potential success and health outcomes of cows around calving time. Thein, O. S., N. A. Ali, R. Y. Mahida, R. C. A. Dancer, M. Ostermann, K. Amrein, G. Martucci, A. Scott, D. R. Thickett, and D. Parekh. 2023. Raised FGF23 Correlates to Increased Mortality in Critical Illness, Independent of vitamin D. Biology 12:309.

FIG. 6 is a schematic diagram of complexities in transition cows, including relationships between pathogen insults such as bacterial infections and LPS (lipopolysaccharide) injections, fibroblast growth factor 23 (FGF23), immune modulation, such as TNF-α (tumor necrosis factor-alpha) enhancing inflammation and alterations to neutrophil recruitment, and environmental insults, such as heat/cold stress, pen crowding/movement, and cow comfort disruptions.

Masuda et al. studied FGF23 responses in mice inoculated intraperitoneally with *E. coli* or *S. aureus* or injected with LPS. They found that all three treatments increased FGF23 levels in mice serum. This study demonstrates there is a role of FGF23 in the immune system besides the role in P and Ca metabolism. In addition, they found recombinant FGF23 protein increased the number of macrophages and induced TNF-α expression of macrophages. These data suggest that FGF23 may be involved in the inflammatory process, in addition to the systemic mineral metabolisms. Masuda, Y., H. Ohta, Y. Morita, Y. Nakayama, A. Miyake, N. Itoh, and M. Konishi. 2015. Expression of Fgf23 in Activated Dendritic Cells and Macrophages in Response to Immunological Stimuli in Mice. Biological & Pharmaceutical Bulletin 38:687-693.

It is well established in the literature that factors creating stress (like heat and cold, over-crowding of pens, pens movements, lack of feed and cow comfort in general) increase immune signaling and permeability of endothelial tissues (gastrointestinal tract, mammary, uterus) allowing for increased levels of LPS in a cow's circulatory system. Therefore, good dairy management practices should help manage the levels of immune activation, LPS and FGF23 in postpartum cows which are at particular risk of pathogen infection and stress after giving birth. LPS injections can be used as a way of simulating stress in research settings.

Reducing FGF23 levels through management and nutrition should help modulate the inflammatory process (for example limiting IL-6, CRP) and improve the immune system responses around birth and postpartum.

The Hypocalcemia Triangle in Dairy Cows

FIG. 7 is a triangular diagram depicting the hypocalcemia triangle in dairy cows, interrelating calcium status with bone metabolism, mineral intake, mineral absorption, and immune activation.

Hypocalcemia or "milk fever" is a condition that impacts 2.8% of cows each lactation in the U.S. (USDA-NAHMS, 2014) and is estimated to cost a dairy farmer $194-299/case due to veterinary costs, reduced milk revenue, and increased risk of culling or death (Liang et al., 2017). Risk of a cow developing clinical hypocalcemia increases with age and milk production (Couto Serrenho et al., 2021). Subclinical hypocalcemia is determined when serum or blood Ca levels decrease below a certain threshold which is associated with negative outcomes such as increased risk of culling, increased risk of other diseases, and reduced milk yield. Subclinical hypocalcemia exists without clinical symptoms of clinical hypocalcemia which include recumbency and compromised neuromuscular and circulatory functions. McArt and Neves (2020) defined subclinical hypocalcemia thresholds in multiparous cows as a measured serum Ca below 7.1 mg/dL on DIM=1 and 8.82 mg/dL on DIM=4.

USDA-NAHMS. 2014. Trends in Dairy Cattle Health and Management Practices in the United States, 1991-2014. November 2022.

Liang, D., L. M. Arnold, C. J. Stowe, R. J. Harmon, and J. M. Bewley. 2017. Estimating US dairy clinical disease costs with a stochastic simulation model. Journal of Dairy Science 100:1472-1486.

Couto Serrenho, R., T. J. DeVries, T. F. Duffield, and Stephen J. LeBlanc. 2021. Graduate Student Literature Review: What do we know about the effects of clinical and subclinical hypocalcemia on health and performance of dairy cows? Journal of Dairy Science 104:6304-6326.

McArt, J. a. A., and R. C. Neves. 2020. Association of transient, persistent, or delayed subclinical hypocalcemia with early lactation disease, removal, and milk yield in Holstein cows. Journal of Dairy Science 103:690-701.

Calcium status in dairy cows is influenced by three main factors, bone metabolism, mineral intake and absorption, and more recently described immune activation (Horst et al., 2021). These three pillars get exacerbated as cow parity increases, increasing the risk of milk fever as cows get older. Retrospective study on the cumulative incidence of milk fever in parturient cows: a case study in the United Arab Emirates, Shaikha Ahmed Alshehhi, Temesgen Mohammed, Aboma Zewude, Berecha Bayissa, Asha Antony, Berhanu Adnew Degafa & Gobena Ameni volume 20, Article number: 587 (2024).

We have managed dairy cow bone metabolism and mineral intake with DCAD program for many years.

Horst, E. A., S. K. Kvidera, and L. H. Baumgard. 2021. Invited review: The influence of immune activation on transition cow health and performance—A critical evaluation of traditional dogmas. Journal of Dairy Science 104: 8380-8410.

However, when cows became immune activated, we were not able to manage the immune activation leg of the hypocalcemia triangle. Now, with our new AI-DCAD strategy we can improve bone metabolism by managing both the acid-base balance of the cows and manage the amount of phosphorus absorbed. Without being limited by any theory or hypothesis, we believe this also reduces the FGF23 levels in cow's blood (serum) by reducing the level of phosphorus entering the blood stream, which creates a synergistic approach to feed cows before parturition.

A large difference in upper limits for healthy FGF23 levels would be expected between humans and cows. In humans, the upper limit for intact FGF23 in serum is typically ≤59 pg/mL for adults (using common assays like chemiluminescence-based immunoassays). In contrast, available data from other mammals suggest higher ranges: for example, healthy cats have a reference interval of 85.8-387.0 pg/mL, and normal rodents (e.g., mice or rats) often show baseline levels around 150-200 pg/mL, with upper limits in healthy states exceeding human values. Although specific reference intervals for intact FGF23 in healthy dairy cows are not well-established in the literature (likely due to limited routine measurement and lack of standardized bovine assays), the physiological differences—such as ruminant phosphate metabolism relying more on salivary recycling and bone turnover compared to humans—suggest cows would align more with other animals, implying higher upper limits (potentially in the hundreds of pg/mL) rather than similar to human levels. This expectation is supported by the role of FGF23 in regulating phosphate in species with varying dietary and metabolic demands.

Anionic Supplements for Controlling Dietary DCAD

Building on this understanding of hypocalcemia's interconnected factors, traditional strategies like anionic supplements have been employed to modulate dietary cation-anion difference (DCAD) and enhance calcium mobilization during the prepartum period.

It is well documented in the literature that feeding anions to dairy cows prepartum reduces the incidence of milk fever (Santos et al., 2019). This study shows that reducing DCAD from +20 to −10 mEq/100 g DM by supplementing anionic supplements reduced urine pH, increased blood Ca at calving and reduced the incidence of milk fever. Low DCAD diets induce metabolic acidosis and increase the sensitivity of PTH (Goff, 2014). This allows Ca homeostasis to proceed more normally around calving and reduces subclinical hypocalcemia and milk fever. Creating a metabolic acidosis in the cow is not a normal process. There is a risk of over acidifying cows especially when feeding anions to a very low urine pH value. Low DCAD diets need to be constantly monitored to avoid feeding excess of anions and urine pH is the best tool to do that. Cows constantly compensate the metabolic acidosis, which makes it hard to consistently maintain it. Ametaj (2025) described the involvement of the immune system around parturition and its relationship to hypocalcemia. The DCAD strategy improves sensitivity of Ca metabolism but has minimal or no impact on the immune system of the cow. In 2014, 28.1% of dairy operations in the U.S. fed dry anionic product to multiparous cows to prevent milk fever (USDA-NAHMS, 2014). Offering an additional nutritional strategy that better fits more dairy operations in the U.S. can further help prevent hypocalcemia in the U.S. dairy population.

Ametaj, B. N. 2025. From Parts to Whole: A Systems Biology Approach to Decoding Milk Fever. Veterinary Sciences 12:347.

Goff, J. P., A. Liesegang, and R. L. Horst. 2014. Diet-induced pseudohypoparathyroidism: A hypocalcemia and milk fever risk factor. Journal of Dairy Science 97:1520-1528.

Santos, J. E. P., I. J. Lean, H. Golder, and E. Block. 2019. Meta-analysis of the effects of prepartum dietary cation-anion difference on performance and health of dairy cows. Journal of Dairy Science 102:2134-2154.

USDA-NAHMS. 2014. Trends in Dairy Cattle Health and Management Practices in the United States, 1991-2014. November 2022.

Dry Phos Binders for Reducing Dietary Phosphorus Absorption

While anionic approaches effectively manage acid-base balance and incidence of hypocalcemia, strategies focusing on phosphorus absorption—such as dry phosphorus binders—have been tried.

Reduction of absorption of dietary phosphorus with phosphate binders has been used in human patients with renal disease for several decades (Sheikh, 1989). Grabherr et al. (2009) in a dose dependent study fed Zeolite A at different levels and demonstrated that feeding Zeolite reduced serum P in dairy cows. They attribute the reduction of serum P to the binding of P in the gut to the aluminum present in the Zeolite A. More recently Kerwin et al., (2019) and Frizzarini et al., (2024) found lower levels of serum P prepartum (3 mg/dL or below), lower incidence of milk fever and higher levels of serum Ca in cow fed Zeolite A prepartum. Pronounced peripartum hypophosphatemia can affect granulocyte counts and phagocytic activity of granulocytes in peripartum cows and lower milk production (Eisenberg, 2018). Lowering serum P in an excessive manner increases the risk of cows developing hemoglobinuria, the appearance of red blood cells in urine. Therefore, managing the degree of hypophosphatemia around partition is important for the health and productivity of the dairy cow.

Sheikh, M. S., J. A. Maguire, M. Emmett, C. A. Santa Ana, M. J. Nicar, L. R. Schiller, and J. S. Fordtran. 1989. Reduction of dietary phosphorus absorption by phosphorus binders. A theoretical, in vitro, and in vivo study. J. Clin. Invest. 83:66-73.

Grabherr, H., M. Spolders, P. Lebzien, L. Huther, G. Flachowsky, M. Furll, and M. Grün. 2009. Effect of zeolite A on rumen fermentation and phosphorus metabolism in dairy cows. Archives of Animal Nutrition 63:321-336.

Kerwin, A. L., C. M. Ryan, B. M. Leno, M. Jakobsen, P. Theilgaard, D. M. Barbano, and T. R. Overton. 2019. Effects of feeding synthetic zeolite A during the prepartum period on serum mineral concentration, oxidant status, and performance of multiparous Holstein cows. Journal of Dairy Science 102:5191-5207.

Frizzarini, W. S., P. L. J. Monteiro, J. P. Campolina, A. L. Vang, O. Soudah, L. R. Lewandowski, M. K. Connelly, S. I. A. Apelo, and L. L. Hernandez. 2024. Mechanisms by Which Feeding Synthetic Zeolite A and Dietary Cation Anion Difference Diets Impacts Mineral Metabolism in Multiparous Holstein Cows: Part I, Journal of Dairy Science S0022030224005460.

Eisenberg, S. W. F., L. Ravesloot, A. P. Koets, and W. Granberg. 2019. Effect of dietary phosphorus deprivation on leukocyte function in transition cows. Journal of Dairy Science 102:1559-1570.

Normal serum phosphorus for cows is in the range of 4.0 to 8.0 mg/dL. While lower serum phosphorus is desirable, it is also desirable to not push the serum phosphorus below 3.6 mg/dL.

Conventional strategy of using a Dry Phos Binder to achieve the desired effects on reducing milk fever incidence requires lowering serum P in prepartum cows below 3.0 mg/dL, which could be detrimental to the cow's immune system.

Al-DCAD: a Hybrid Strategy for Phosphorus Binding and DCAD Control

This disclosure is generally directed to a hybrid strategy for managing early lactation challenges in dairy cows, including obtaining improved ranges of serum phosphorus in the cows. Al-DCAD is a hybrid strategy that uses the combination of a mild acid-base status (urine pH 6.3-7.8) and mild reduction and management of serum phosphorus (3.6 to 4.6 mg/dL).

Al-DCAD includes one or more minerals that bind dietary phosphorus in addition to anionic properties. The minerals are sources of phosphorus-binding elements, which can be selected from the group consisting of aluminum(III), iron (II), iron(III), and any combination thereof.

Aluminum ($Al^{3+}$) has a high affinity for negatively charged phosphate groups ($PO_4^{3-}$) due to its strong Lewis acidity and positive charge. This makes phosphate-bearing biomolecules, such as ATP, phosphorylated proteins, or inorganic phosphates, likely targets for aluminum binding in biological systems. The binding of aluminum to phosphate groups can be described as a coordination or complexation reaction. The general form of such interaction can be represented as: $Al(3+)+PO_4^{3-} \leftrightharpoons AlPO_4$ (or related complexes) in solution, but this may be different for zeolites. Fe(3+) and Fe(2+) are similar. The complex formed is very insoluble and therefore rendered unavailable for absorption.

The stoichiometry of P:Al and of P:Fe(III) is theoretically 1:1, but the binding is probably not complete in biological processes. The stoichiometry of P:Fe(II) is theoretically 2:3, but the binding is probably not complete in biological processes nor is it desirable to bind all dietary phosphorus as it is essential for a host of metabolic reactions In various embodiments, the one or more sources of phosphorus-binding elements are soluble in weak acid. The abomasum of the cow is a weak acid pH in the range of 2 to 4. It is desirable for the Target concentration of the dilute HCl to this pH range.

In various embodiments, the Al-DCAD additionally has one or more other beneficial ingredients. For example, non-protein nitrogen (NPN), which is used to replace part of the dietary protein. Protein in the diet of the cows is usually one of the main sources of P in the diet. According to an embodiment, NPN is used to replace some of the crude protein in the cow's diet, thereby reducing the need for crude protein in the basal diet and reducing the dietary load of phosphorus in the basal diet.

Comparative Solubilities of Aluminum Sources in Acidic Conditions

The effectiveness of Al-DCAD's phosphorus-binding elements relies in part on their solubility in acidic conditions, as demonstrated by comparative analyses of aluminum sources across pH levels.

FIG. 8 is a graph showing aluminum solubility of several aluminum sources at varying media pH levels. Levels were chosen to represent pH levels found in various portions of the ruminant digestive system.

More particularly, FIG. 8 illustrates the solubility of aluminum, expressed as a percentage of the theoretical formulated content for several aluminum-containing products—including two dry phosphorus binders, aluminum sulfate, and Al-DCAD—across varying media pH levels ranging from about 2.4 to about 8. The graph evidences that Al-DCAD exhibits superior solubility at pH 3. This differential solubility profile underscores the advantages of soluble aluminum sources like Al-DCAD for effective phosphorus binding in the gastrointestinal tract of dairy cows, where pH variations influence mineral availability and metabolic interactions without compromising safety or efficacy.

Some sources of aluminum are not soluble at pH 6 to 8. Lowering pH to 3 increases solubility of the Dry Phos Binder 1, Dry Phos Binder 2, Aluminum Sulfate, and Al-DCAD to 5.4, 33.2, 70 and 79.3%, respectively. Nevertheless, Dry Phos Binders had lower solubility at pH 3. As stated previously, pH 2 to 4 is normal for the abomasum having solubility in this portion of the digestive system allows for the formation of the insoluble aluminum phosphate complex and renders the phosphorus unavailable for absorption in the remaining portions of the digestive system.

Comparative Features of Dry Phos Binders and Al-DCAD

These solubility differences highlight broader distinctions between Al-DCAD and dry phosphorus binders, including product form, handling, and nutritional enhancements, as illustrated in the following comparison.

FIG. 9 is a Venn diagram comparing features of Al-DCAD and a dry phosphorus binder, including solubility of aluminum, product form, handling characteristics, and additional nutritional values.

More particularly, FIG. 9 is a Venn diagram that compares the features of Al-DCAD and a dry phosphorus binder (Dry Phos Binder), highlighting their shared objective and distinct characteristics in the context of limiting dietary phosphorus absorption in dairy cows. The overlapping section evidences the common goal of both products to restrict phosphorus uptake from the diet, serving as a core mechanism for managing metabolic health. In contrast, the unique attributes of Al-DCAD—such as soluble aluminum, acidification to reduce DCAD, liquid product form for easier handling and feeding, the ability to monitor tank use, consistent mixing throughout the ration, added nutritional value from non-protein nitrogen, and urea as the mineral blend carrier—demonstrate its advantages in solubility, nutritional enhancement, and practical application on farms. Meanwhile, the Dry Phos Binder is characterized by insoluble aluminum and a dry product form suited for on-farm handling, underscoring a more traditional approach with potential limitations in solubility and additional benefits. This comparative visualization evidences how Al-DCAD integrates phosphorus-binding efficacy with improved usability and supplementary nutritional support, potentially offering a more versatile solution for prepartum dairy cow nutrition without toxicity concerns. Al-DCAD is a soluble source of minerals with DCAD capabilities and N contribution to the diet.

To validate these comparative advantages, controlled trials were conducted to assess the impacts of Al-DCAD feeding during the prepartum period versus other strategies on serum minerals, intake, and health outcomes in prepartum dairy cows.

Field Data and Discussion

The following sections show and discuss field data including blood (serum) database, herd data, and health data.

Trial Structure

FIG. 10 is a schematic timeline of the trial structure for ANI vs Al-DCAD products, including pre-treatment covariate and treatment periods with indicated blood and urine sampling days for a commercial dry anionic product (ANI), low Al-DCAD, and high Al-DCAD treatments.

Trial evaluating a classic DCAD diet using a dry anionic product for dry cows compared to two feeding rates of Al-DCAD. Treatments were assigned in a randomized complete block design, with lactation, days in gestation, previous lactation milk yield used as blocking factors. The objective was to evaluate the impact of dietary treatment on serum mineral loads, dry matter intake, and acid base status in multiparous cows. Cows were enrolled with a 7-day covariate (Cov) period to collect data and observe cows before any treatments were delivered, allowing for baseline measurements for individual cows to be used in statistical analysis. A 14-day treatment period followed where cows received specific treatments added on top of and mixed throughout their individual basal diet. These treatments consisted of:

1) ANI: commercial dry anionic product to reach a diet DCAD=−15 mEq/100 g DM and P:(Suppl. Al×Ca) =488
2) Lo Al-DCAD: Liquid Al-DCAD to reach a diet DCAD=−6 mEq/100 g DM and P:(Suppl. Al×Ca) =2.80, and
3) Hi Al-DCAD: Liquid Al-DCAD to reach a diet DCAD=−11 mEq/100 g DM and P:(Suppl. Al×Ca) =2.30.

A mixed statistical model was used to evaluate random effect of cow within block by treatment, and fixed effects (P—value significance) by treatment (Trt), block (Block), time (Day), and treatment by time interaction (Trt×DAY).

FIG. 11 is a bar chart comparing serum calcium concentrations over treatment days for anionic (ANI), low Al-DCAD, and high Al-DCAD treatments in parous cows.

More particularly, FIG. 11 is a bar chart comparing serum calcium concentrations over treatment days for anionic (ANI), low Al-DCAD, and high Al-DCAD treatments in parous cows. The bar chart, with error bars, displays data from study days 6, 9, 12, and 14, revealing a treatment effect (P=0.06) and day influence (P<0.01), while covariate, block, and treatment-by-day interactions show no significance (P=0.21, P=0.15 and P=0.96, respectively). The evidence indicates that high Al-DCAD treatments maintain or elevate serum calcium levels compared to ANI while the low Al-DCAD numerical elevates serum calcium levels compared to ANI. This trial demonstrated that the Al-DCAD group consistently showing the highest values, peaking at approximately 9.86 mg/dL on day 14 versus 9.56 mg/dL for low Al-DCAD and 9.50 mg/dL for ANI. This underscores the efficacy of Al-DCAD in supporting stable calcium metabolism during the prepartum period through its synergistic phosphorus-binding and DCAD-modulating properties, contributing to improved metabolic health in dairy cows without toxicity or adverse impacts.

FIG. 12 is a bar chart comparing serum phosphorus concentrations over treatment days for anionic (ANI), low Al-DCAD, and high Al-DCAD treatments in parous cows.

More particularly, FIG. 12 is a bar chart comparing serum phosphorus concentrations over treatment days for anionic (ANI), low Al-DCAD, and high Al-DCAD treatments in parous cows. The bar chart, with error bars, presents data from study days 6, 9, 12, and 14, demonstrating significant treatment (P<0.01), and no significant day, covariate, block or treatment-by-day interaction (P>0.12). The evidence shows that ANI maintains higher serum phosphorus levels, consistently around 5.6 to 6.0 mg/dL across the period, while both low and high Al-DCAD treatments result in markedly lower concentrations, starting near 4.5 to 4.1 mg/dL on day 6 with those values being maintained by day 14. The high Al-DCAD shows the most pronounced decreased in serum P relative to the low Al-DCAD in the dose dependent manner. This highlights the superior phosphorus-binding capacity of Al-DCAD, effectively lowering serum phosphorus within a desirable range to mitigate risks like hypocalcemia and support optimal metabolic health in prepartum dairy cows through combined aluminum supplementation and controlled DCAD, without inducing toxicity or nutritional imbalances.

FIG. 13 is a bar chart comparing average cow urine pH over treatment days for anionic (ANI), low Al-DCAD, and high Al-DCAD treatments in parous cows.

More particularly, FIG. 13 is a bar chart comparing urine pH over treatment days for anionic (ANI), low Al-DCAD, and high Al-DCAD treatments in parous cows. The bar chart, with error bars, displays data from study days 3, 6, 9, 12, and 14, revealing significant treatment, block, covariate effects (P<0.09 for all), and no significant day or treatment-by-day interaction (P=0.27). The evidence indicates that ANI substantially lowers urine pH compared to Al-DCAD, with ANI urine pH averaging 6.8 on day 3 and dropping to about 6.1-6.0 on study days thereafter. Urine pH across treatment days for high Al-DCAD varies from about 6.8-7.8 and for low Al-DCAD at a higher range of about 7.5-7.8. This demonstrates the ability of Al-DCAD to induce controlled acidification in a dose-dependent manner, aligning with its DCAD-modulating properties to enhance metabolic responses like PTH sensitivity and calcium homeostasis in prepartum dairy cows, while maintaining safety and avoiding toxicity or excessive acid-base disruptions.

FIG. 14 is a bar chart comparing average cow urine pH over the entire study periods for anionic (ANI), low Al-DCAD, and high Al-DCAD treatments in parous cows.

More particularly, the bar chart of FIG. 14, with error bars, presents the overall means of urine pH in the covariate and treatment period of the study. The evidence shows that covariate baseline urine pH ranges from 8.3-8.6. The treatment period ANI yields lowest average urine pH values, around 6.2, while low Al-DCAD and high Al-DCAD maintains a higher level near 7.6 and 7.2 respectively, illustrating a clear dose-response relationship in acidification. All diets decreased urine pH from the covariate to the treatment period. This highlights Al-DCAD's capacity to achieve targeted DCAD reduction and mild metabolic acidosis, promoting improved PTH receptor sensitivity and calcium homeostasis in prepartum dairy cows without inducing toxicity or disrupting overall metabolic balance.

FIG. 15 is a graph comparing average dry matter intake over treatment days for anionic (ANI), low Al-DCAD, and high Al-DCAD treatments in parous cows.

More particularly, FIG. 15 is a graph, with error bars, displaying daily data from study days 1 through 14, revealing no significant treatment effect (P=0.43) or treatment-by-day interaction (P=0.64), but significant covariate (P=0.06) and day effects (P<0.01), with no block effect (P=0.12). The evidence indicates comparable dry matter intake across all groups, generally ranging from approximately 10 to 14 kg per day with natural fluctuations over time, where ANI, low Al-DCAD, and high Al-DCAD maintain similar levels without notable depression in the Al-DCAD treatments. This demonstrates that Al-DCAD supplementation, through its phosphorus-binding and mild DCAD-lowering mechanisms, does not adversely affect feed palatability or consumption in prepartum dairy cows, supporting optimal nutrient intake and metabolic health without toxicity or intake-related compromises.

Effects on DIM Cows on Serum Calcium, Subclinical Hypocalcemia, and Phosphorus

FIG. 16 is a bar chart comparing serum calcium levels of cows on commercial dairies among None (as a control), Anionic (aka ANI), a Dry Phos Binder, and Al-DCAD treatments across days in milk (DIM).

More particularly, FIG. 16 is a bar chart, displaying average serum calcium concentrations for closeup cows at −1 DIM and fresh cows at 1, 2, 3, and 4 DIM, based on sample sizes of None n=354, Anionic n=7,240, Dry Phos Binder n=440, and Al-DCAD n=1,200. The evidence indicates that Al-DCAD consistently achieves the highest serum calcium levels in fresh cows. Serum calcium levels differ between groups in the closeup −1 DIM, with None averaging the lowest serum calcium prior to calving. Al-DCAD cows have the highest serum calcium in the fresh period, with 1 DIM and 4 DIM averaging 8.28 and 8.93 mg/dL respectively. This compares to lower serum calcium values for Anionic (7.97 and 8.85 mg/dL) Dry Phos Binder (8.04 and 8.84 mg/dL), and None (7.48 and 8.58 mg/dL) at 1 and 4 DIM. This demonstrates the superior performance of Al-DCAD in enhancing postpartum calcium homeostasis via its phosphorus-binding elements and controlled DCAD, effectively mitigating hypocalcemia risks in dairy cows.

FIG. 17 is a bar chart comparing the percentage of the cow population on commercial dairies showing subclinical hypocalcemia among None (as control), Anionic (aka ANI), Dry Phos Binder, and Al-DCAD treatments for 1 and 4 days in milk (DIM).

More particularly, FIG. 17 displays incidence rates where cows are classified as hypocalcemic if serum calcium is below 7.10 mg/dL at 1 DIM or below 8.82 mg/dL at 4 DIM, based on criteria from McArt and Neves (2020). The evidence indicates that Al-DCAD results in the lowest incidence of subclinical hypocalcemia, with rates substantially reduced compared to None, Anionic, and Dry Phos Binder at 1 DIM. By 4 DIM, Al-DCAD substantially reduced hypocalcemia compared to None and Dry Phos Binder. This highlights Al-DCAD effectiveness in preventing calcium imbalances postpartum. This underscores the benefits of Al-DCAD's phosphorus-binding and DCAD-modulating approach in enhancing metabolic health and reducing hypocalcemia risks in dairy cows without toxicity or adverse effects. McArt, J. a. A., and R. C. Neves. 2020. Association of transient, persistent, or delayed subclinical hypocalcemia with early lactation disease, removal, and milk yield in Holstein cows. Journal of Dairy Science 103:690-701.

FIG. 18 is a bar chart comparing serum phosphorus levels among of cows on commercial dairies None (as a control), anionic (aka ANI), a Dry Phos Binder, and Al-DCAD treatments across days in milk (DIM).

More particularly, FIG. 18 is a bar chart displaying average serum phosphorus concentrations for closeup cows at −1 DIM and fresh cows at 1, 2, 3, and 4 DIM, based on sample sizes of None n=354, Anionic n=7,233, Dry Phos Binder n=440, and Al-DCAD n=1,200. The evidence indicates that Dry Phos Binders achieve the lowest serum P level in the closeup period, with Al-DCAD following with a more moderate serum P at 3.96 mg/dL. Both Al-DCAD and Dry Phos Binder differ to the higher closeup serum P levels of None and Anionic (>6.20 mg/dL). Al-DCAD strategy averaging 3.96 mg/dL serum P prepartum is close to the normal serum P range in dairy cows (Satter, 2002). This indicates that both the Dry Phos Binder and Al-DCAD modulate serum P prepartum but do so at different levels prior to parturition. This demonstrates the enhanced phosphorus-binding efficacy of Al-DCAD in the closeup period, targeting a more moderate level of serum phosphorus compared to other closeup diet programs. The Al-DCAD and Dry Phos Binder achieve the lowest serum phosphorus levels in fresh cows 1 DIM with 3.45 and 3.91 mg/dL respectively. This contrasts with the higher serum phosphorus values for None (4.66 mg/dL) and Anionic (5.35 mg/dL) at 1 DIM. Both Al-DCAD and Dry Phos Binder increase serum P levels from 1 to 4 DIM reaching 6.47 and 6.49 mg/dL respectively. The None and Anionic group also increase in serum P from 1 to 4 DIM, but the rate of change by DIM is lower and reaches lower levels of serum P by 4 DIM compared to Al-DCAD and Dry Phos Binder. The Al-DCAD effectively reduces serum phosphorus in closeup cows to optimal ranges that support improved calcium metabolism and reduce hypocalcemia risks in postpartum dairy cows through its combined aluminum supplementation and controlled DCAD, without inducing toxicity or metabolic disruptions. Satter, L. 2002. What Goes In Must Come Out: Phosphorus Balance on Dairy Farms. American Association of Bovine Practitioners Conference Proceedings 125-130.

Cows fed Al-DCAD had the highest serum Ca levels postpartum, lowest rate of subclinical hypocalcemia, while at the moderate serum P level before calving. This demonstrates a synergistic balance, that the diet P binder and DCAD hybrid strategy is working better and more efficiently at promoting postpartum cow health than the individual strategies of Dry Phos Binder or Anionic alone.

Prepartum Serum Mineral Levels and Dietary Ratios

FIG. 19 is a graph comparing serum phosphorus levels versus diet phosphorus-to-aluminum ratio for Al-DCAD and Dry Phos Binder treatments in closeup parous dry cows.

More particularly, FIG. 19 is a graph comparing serum phosphorus levels versus diet phosphorus-to-aluminum ratio for Al-DCAD and Dry Phos Binder treatments in closeup parous dry cows on commercial dairies, plotted as a locally weighted linear regression based on samples from closeup diets fed Dry Phos Binder (n=142) or Al-DCAD (n=759). The evidence illustrates a linear relationship between the dietary P-to-Al ratio and closeup serum phosphorus concentrations for Al-DCAD where decreasing the ratio from approximately 2.5 to 1.5 reduces serum P from about 4.6 to 3.6 mg/dL in Al-DCAD-fed cows. This linear relationship does not appear with the Dry Phos Binder. This highlights the impact of dietary P-to-Al ratio of Al-DCAD in phosphorus binding, likely due to its soluble aluminum and mild DCAD-lowering effects. This relationship enables effective management of serum phosphorus to optimal levels that support calcium homeostasis and reduce hypocalcemia risks in prepartum dairy cows without toxicity or metabolic issues.

The target range for this graph is P:(Suppl. Al)=1.5 to 2.5:1, which is the serum range of 3.6 to 4.6 mg/dL. This serum P range results in an ideal serum Ca and health responses around calving for Al-DCAD.

FIG. 20 is a graph comparing closeup serum phosphorus levels versus diet phosphorus-to-(aluminum multiplied by calcium) ratio for Al-DCAD and Dry Phos Binder treatments in closeup parous dry cows.

More particularly, FIG. 20 is a graph comparing closeup serum phosphorus levels versus diet phosphorus-to-(supplemental aluminum multiplied by calcium) ratio for Al-DCAD and Dry Phos Binder treatments in closeup rations for parous dry cows on commercial dairies, plotted as a locally weighted linear regression based on samples from cows fed Dry Phos Binder n=142, or Al-DCAD n=759.

Desired range of P:(Suppl. Al×Ca)=1.8-4.0. It is evident from this graph that adding Ca to the ration can lower serum P for cows on Al-DCAD, however this relationship appears to be inverse for Dry Phos Binders. This linear relationship of Al-DCAD diet phosphorus-to-(supplemental aluminum multiplied by calcium) to serum phosphorus allows for more effective management of prepartum dairy cows.

FIG. 21 is a graph comparing serum strong ion difference (SID) levels versus dietary phosphorus-to-aluminum ratio for Al-DCAD and Dry Phos Binder treatments in closeup parous dry cows.

More particularly, FIG. 21 is a graph comparing serum strong ion difference (SID; [Na]+[K]— [Cl] mEq/L) levels versus dietary phosphorus-to-aluminum ratio for Al-DCAD and Dry Phos Binder treatments in closeup parous dry cows on commercial dairies, plotted as a locally weighted linear regression based on samples from closeup diets fed Dry Phos Binder (n=142) and Al-DCAD (n=759). The evidence illustrates a trend between the dietary P-to-Al ratio and serum SID for Al-DCAD, where increasing the ratio from approximately 1.2 to 2.5 elevates SID from about 41.0 to 43.0 mEq/L, whereas Dry Phos Binder exhibits variation around 43.5 mEq/L at a dietary P-to-Al ratio between 1.2 to 2.5. This highlights Al-DCAD's ability to modulate acid-base balance more dynamically. The positive relationship between serum SID and dietary P-to-Al is modulated through Al-DCAD soluble aluminum and DCAD-lowering effects, facilitating better management of metabolic acidosis and enhancing overall mineral homeostasis in prepartum dairy cows without inducing toxicity or disruptions to electrolyte equilibrium.

Cows fed Al-DCAD had a lower serum SID than Dry Phos Binder cows, this is due to the mild acidification capability of Al-DCAD. Reducing the P:(Suppl. Al) ratio by increasing the feeding rate of Al-DCAD reduced serum SID, mostly due to its acidification capabilities.

FIG. 22 is a graph comparing serum phosphorus levels versus DCAD (dietary cation-anion difference) for Anionic (aka ANI), Dry Phos Binder, and Al-DCAD treatments in closeup parous dry cows.

More particularly, FIG. 22 is a graph comparing serum phosphorus levels versus dietary DCAD (dietary cation-anion difference) for Anionic (aka ANI), Dry Phos Binder, and Al-DCAD treatments in closeup parous dry cows on commercial dairies, plotted as a locally weighted linear regression based on samples from closeup diets fed Dry Phos Binder (n=142), Al-DCAD (n=759), and Anionic (n=1,368). The evidence illustrates the relationship between DCAD and serum phosphorus for Anionic, where altering DCAD from −40 to +10 mEq/100 g DM has minimal influence on serum P. This differs from Al-DCAD, where increasing DCAD from approximately −20 to +5 mEq/100 g DM elevates serum P from about 3.6 to 4.3 mg/dL. The Dry Phos Binder varies in influence of DCAD on serum P, with DCAD from +15 to +40 mEq/100 g DM influence serum P in a negative and positive relationship. The serum P of Al-DCAD measures consistently lower than Anionic, while being consistently higher than Dry Phos Binder. This highlights Al-DCAD's enhanced ability to maintain lower serum phosphorus across a range of DCAD values through its phosphorus-binding elements and mild acidification, optimizing mineral balance to support calcium metabolism and reduce hypocalcemia risks in prepartum dairy cows without toxicity or metabolic disturbances.

Lowering DCAD when using an anionic product has a minimal effect on serum P in prepartum cows. However, lowering DCAD from +10 mEq to −15 mEq/100 g of DM when feeding Al-DCAD reduces serum P in prepartum cows. This response is mostly due to the ability of the Al-DCAD strategy of acidifying the cow and at the same time binding P in the gastrointestinal tract. There is no effect of changing DCAD on serum P in cows fed dry P binder.

FIG. 23 is a graph comparing serum phosphorus levels versus dietary calcium percentage for Al-DCAD and Dry Phos Binder treatments in closeup parous dry cows.

More particularly, FIG. 23 is a graph comparing serum phosphorus levels versus dietary calcium percentage for Al-DCAD and Dry Phos Binder treatments in closeup parous dry cows on commercial dairies, plotted as a locally weighted linear regression based on samples from closeup diets fed Dry Phos Binder (n=142) and Al-DCAD (n=759). The evidence illustrates an inverse relationship between dietary calcium and serum phosphorus concentrations for Al-DCAD, and a direct relationship for Dry Phos Binder. Increasing dietary Ca from approximately 0.45 to 1.10% DM increases serum P from 2.5 to 3.9 mg/dL for Dry Phos Binder, while increasing dietary Ca in the same range decreases serum P from 4.5 to 3.7 mg/dL for Al-DCAD, indicating a different response at equivalent dietary calcium levels. This highlights Al-DCAD's enhanced efficiency in managing phosphorus absorption in the presence of higher calcium, attributed to its soluble aluminum sources and mild DCAD modulation, allowing for optimized dietary formulations that support better calcium homeostasis and mitigate hypocalcemia risks in prepartum dairy cows without inducing toxicity or nutritional imbalances.

Increasing dietary Ca from 0.4% to 0.9% reduces serum P in prepartum cows fed Al-DCAD while the opposite effect occurs in cows fed dry P binders. It appears dietary Ca interferes with the binding capacity of the Dry Phos Binder. However, dietary Ca up to 0.9% DM synergizes with the binding capacity of the Al-DCAD diets.

FIG. 24 is a graph comparing serum phosphorus levels versus dietary calcium-to-phosphorus ratio for Al-DCAD and Dry Phos Binder treatments in closeup parous dry cows.

More particularly, FIG. 24 is a graph comparing serum phosphorus levels versus dietary calcium-to-phosphorus ratio for Al-DCAD and Dry Phos Binder treatments in closeup parous dry cows on commercial dairies, plotted as a locally weighted linear regression based on samples from closeup diets fed Dry Phos Binder (n=142) and Al-DCAD (n=759). The evidence illustrates an inverse relationship between the dietary Ca-to-P ratio and serum phosphorus concentrations for Al-DCAD, where increasing the diet ratio from approximately 1.5 to 3.5 reduces serum P from 4.8 to 3.6 mg/dL. The evidence illustrates a positive relationship for Dry Phos Binder, with serum P increasing from 2.7 to 3.9 mg/dL over the same diet Ca-to-P ratio increase from 1.5 to 3.5. This highlights Al-DCAD's synergistic impact between dietary Ca and dietary P, as well superior efficiency in phosphorus management across varying Ca:P balances. This is likely due to its soluble aluminum sources and mild DCAD modulation, enabling optimized dietary strategies that enhance calcium metabolism and mitigate hypocalcemia risks in prepartum dairy cows without inducing toxicity or nutritional disruptions.

Increasing dietary Ca:P ratio from 1.5:1 to 3.5:1 reduces serum P in prepartum cows fed Al-DCAD while the opposite effect occurs in cows fed dry P binders. The dietary Ca:P ratio appears to be more effective than just dietary Ca as the slopes are better than FIG. 23. This response is due to the ability of dietary Ca to bind dietary P in the gastrointestinal tract.

These prepartum changes set the stage for postpartum outcomes, where serum mineral levels in early lactation further illustrate the strategies' impacts on calcium and phosphorus dynamics.

Postpartum Serum Responses to Dietary Ratios

FIG. 25 is a graph comparing serum calcium levels at 1-2 days in milk (DIM) versus dietary phosphorus-to-aluminum ratio for Al-DCAD and Dry Phos Binder treatments in multiparous cows.

More particularly, FIG. 25 is a graph comparing serum calcium levels at 1-2 days in milk (DIM) versus dietary phosphorus-to-supplemental aluminum ratio for Al-DCAD and Dry Phos Binder treatments in multiparous cows on commercial dairies, plotted as a locally weighted linear regression based on samples from closeup diets fed Dry Phos Binder (n=90) or Al-DCAD (n=186). The evidence illustrates an inverse relationship between the dietary P-to-Suppl. Al ratio and serum calcium concentrations for Al-DCAD, where decreasing the ratio from 2.5:1 to 1.5 elevates serum Ca from about 8.0 to 8.7 mg/dL for Al-DCAD. This relationship between dietary P-to-Suppl. Al ratio and serum calcium is non-linear for Dry Phos Binder. Decreasing the ratio from 1.75 to 1.0 alternates serum Ca from 8.20 to 8.40 mg/dL for Dry Phos Binder. Overall, the Al-DCAD curve reaches higher serum Ca levels at the same dietary P-to-Suppl. Al ratio compared to Dry Phos Binder. This indicates superior calcium support at equivalent ratios. This underscores Al-DCAD's enhanced efficacy in improving postpartum calcium homeostasis through its soluble aluminum-based phosphorus binding and mild DCAD reduction, effectively mitigating hypocalcemia risks in dairy cows without inducing toxicity or nutritional imbalances.

Reducing the P:(Suppl. Al) ratio from 2.5:1 to 1.5 increases average serum Ca from 8.0 to 8.75 mg/dL on DIM 1&2 in cows fed Al-DCAD. Serum Ca also varies from 8.2 to 8.4 mg/dL in cows fed dry P binders when the ratio changes from 1.75:1 to 1.0:1. This indicates that cows fed Al-DCAD are more efficient at maintaining serum Ca in the first 2 DIM than cows fed Dry Phos Binders, especially in the ratios between 1.50 to 1.75 where cows fed Al-DCAD maintain about 0.4 mg/dL more serum Ca.

FIG. 26 is a graph comparing serum calcium levels at 1-4 days in milk (DIM) versus dietary phosphorus-to-aluminum ratio for Al-DCAD and Dry Phos Binder treatments in multiparous cows.

More particularly, FIG. 26 is a graph comparing serum calcium levels at 1-4 days in milk (DIM) versus dietary phosphorus-to-supplemental aluminum ratio for Al-DCAD and Dry Phos Binder treatments in multiparous cows on commercial dairies, plotted as a locally weighted linear regression based on samples from closeup diets fed Dry Phos Binder (n=189) or Al-DCAD (n=372). The evidence illustrates an inverse relationship between the dietary P-to-Suppl. Al ratio and serum calcium concentrations for Al-DCAD, where decreasing the ratio from 2.5 to 1.2 elevates serum Ca from about 8.3 to 8.9 mg/dL for Al-DCAD. Decreasing the ratio from 1.75 to 1.0 has a non-linear relationship on serum Ca for Dry Phos Binder, with the serum Ca levels varying between 8.5 to 8.7 mg/dL. At the same dietary P-to-Suppl. Al ratio, Al-DCAD serum Ca curve is positioned higher overall, indicating superior calcium support at equivalent ratios. This underscores Al-DCAD's enhanced efficacy in sustaining postpartum calcium homeostasis through its soluble aluminum-based phosphorus binding and mild DCAD reduction, effectively mitigating hypocalcemia risks in dairy cows without inducing toxicity or nutritional imbalances.

Reducing the P:(Suppl. Al) ratio from 2.5:1 to 1.5 increases average serum Ca from 8.3 to 8.8 mg/dL on the first 4 days in milk in cows fed Al-DCAD. For Dry Phos Binder, serum Ca stays between 8.5 to 8.6 mg/dL with the ratio changes from 1.75:1 to 1:1. Effects are similar to DIM 1&2.

FIG. 27 is a graph comparing serum calcium levels at 1-2 days in milk (DIM) versus dietary phosphorus-to-(aluminum multiplied by calcium) ratio for Al-DCAD and Dry Phos Binder treatments in multiparous cows.

More particularly, FIG. 27 is a graph comparing serum calcium levels at 1-2 days in milk (DIM) versus dietary phosphorus-to-(aluminum multiplied by calcium) ratio for Al-DCAD and Dry Phos Binder treatments in multiparous cows on commercial dairies, plotted as a locally weighted linear regression based on samples from closeup diets fed Dry Phos Binder (n=90) or Al-DCAD (n=186). The evidence illustrates an inverse relationship between the dietary P-to-(Suppl. Al×Ca) ratio and serum calcium concentrations, where decreasing the ratio from approximately 4.0 to 1.8 elevates serum Ca from 8.1 to 8.7 mg/dL for Al-DCAD. For Dry Phos Binder, the same ratio range from 4.0 to 1.8 results in a serum Ca level between 8.1 to 8.6 mg/dL with no clear relationship between the ratio and serum Ca levels. At a dietary P-to-(Suppl. Al×Ca) ratio<2.0, the Al-DCAD serum Ca curve is positioned higher overall, indicating better calcium maintenance at equivalent ratios. The linear-like trend of the Al-DCAD between serum Ca and dietary P-to-(Suppl. Al×Ca) ratio suggests a more direct relationship between these two variables not demonstrated with the Dry Phos Binder. This highlights Al-DCAD's superior integration of phosphorus binding with calcium dynamics via soluble aluminum and controlled DCAD modulation, optimizing early postpartum calcium metabolism and reducing hypocalcemia risks in dairy cows without toxicity or metabolic disruptions.

Reducing the ratio by increasing dietary Ca or Al increases the serum Ca in cows fed Al-DCAD. The response seems to be neutral or non-existent in cows fed Dry Phos Binders.

FIG. 28 is a graph comparing serum calcium levels at 1-4 days in milk (DIM) versus dietary phosphorus-to-(aluminum multiplied by calcium) ratio for Al-DCAD and Dry Phos Binder treatments in multiparous dry cows.

More particularly, FIG. 28 is a graph comparing serum calcium levels at 1-4 days in milk (DIM) versus dietary phosphorus-to-(supplemental aluminum multiplied by calcium) ratio for Al-DCAD and Dry Phos Binder treatments in multiparous cows on commercial dairies, plotted as a locally weighted linear regression based on samples from closeup diets fed Dry Phos Binder (n=189) or Al-DCAD (n=372). The evidence illustrates an inverse relationship between the dietary P-to-(Suppl. Al×Ca) ratio and serum calcium concentrations in Al-DCAD where decreasing the ratio from 4.0 to 1.8 elevates serum Ca from 8.5 to 8.8 mg/dL. With the Dry Phos Binder, serum Ca ranges from 8.4 to 8.9 mg/dL under a similar dietary P-to-(Suppl. Al×Ca) ratio, with no direct effect of P:(Suppl. Al×Ca) above 2.0. The Al-DCAD curve positioned higher over the range of P:(Suppl. Al×Ca) of 2.0 to 1.5, indicating enhanced calcium support at equivalent ratios.

Reducing the P:(Suppl. Al×Ca) ratio from 4.0:1 to 1.5 increases average serum Ca from 8.5 to 8.8 mg/dL om the first 4 DIM in cows fed Al-DCAD. Serum Ca in cows fed Dry Phos Binder does not seem to have a direct effect by the P:(Suppl. Al×Ca) ratio.

Impact of DCAD on Postpartum Serum Levels

FIG. 29 is a graph comparing the effect of dietary cation-anion difference (DCAD) on serum calcium at 1-2 days in milk (DIM) for Anionic (aka ANI), Dry Phos Binder, and Al-DCAD treatments in multiparous cows.

More particularly, FIG. 29 is a graph comparing the effect of dietary cation-anion difference (DCAD) on serum calcium at 1-2 days in milk (DIM) for Anionic (aka ANI), Dry Phos Binder, and Al-DCAD treatments in multiparous cows on commercial dairies, plotted as a locally weighted linear regression based on samples from closeup diets fed Dry Phos Binder (n=90), Al-DCAD (n=186), and Anionic (n=1,482). The evidence illustrates varying responses to DCAD reduction:

- for Anionic, decreasing DCAD from +10 to −30 mEq/100 g DM increases serum Ca from about 7.7 to 8.4 mg/dL;
- for Dry Phos Binder, it shows a flat or minimal response of serum Ca around 8.3 mg/dL across +20 to +40 DCAD, while once DCAD drops below +20 mEq/100 g DM serum drops below 8.3 mg/dl;
- however, Al-DCAD exhibits a positive effect on serum Ca, elevating serum Ca from 8.4 to 9.0 mg/dL as DCAD drops from +10 to −20 mEq/100 g DM, with a better serum Ca effect as DCAD decreases from 0 to −20 mEq/100 g DM.

This highlights Al-DCAD's synergistic advantage in leveraging mild acidification alongside phosphorus binding to achieve superior calcium elevation postpartum, effectively reducing hypocalcemia risks in dairy cows without toxicity or acid-base excesses.

Reducing DCAD from +10 to −30 mEq/100 g of DM increases serum Ca (average DIM 1&2) from 7.7 to 8.4 mg/dL in cows fed Anionic diets. Reducing DCAD in cows fed Dry Phos Binder has no effect until DCAD drops below +20 mEq/100 g DM, in which serum CA declines. However, reducing DCAD from +10 mEq to −20 mEq/100 g of DM increases serum Ca to the highest levels, from 8.4 to 9.0 mg/dL in cows fed Al-DCAD strategy. The Al-DCAD strategy is improving cows' serum Ca status in the first 2 days after calving to a different level compared to other strategies. The capability of the strategy to mildly acidify cows and potentially improving sensitivity to PTH and Ca metabolism; mildly lower serum P by using more efficient P binding sources and potentially lowering FGF23 and improving the immune system responses; and synergistically working with dietary Ca makes this strategy unique to manage Ca status in dairy cows.

Impact of DCAD on Postpartum Serum Levels

FIG. 30 is a graph comparing the effect of dietary cation-anion difference (DCAD) on serum calcium at 1-4 days in milk (DIM) for Anionic (aka ANI), Dry Phos Binder, and Al-DCAD treatments in multiparous cows.

More particularly, FIG. 30 is a graph illustrating the effect of dietary cation-anion difference (DCAD) on serum calcium at 1-4 days in milk (DIM) for Anionic (aka ANI), Dry Phos Binder, and Al-DCAD treatments in multiparous cows on commercial dairies, plotted as a locally weighted linear regression based on samples from closeup diets fed Dry Phos Binder (n=189), Al-DCAD (n=372), and Anionic (n=2,938). The evidence shows distinct patterns:

- for Anionic, reducing DCAD from +10 to −30 mEq/100 g DM increases serum Ca from about 8.3 to 8.6 mg/dL;
- for Dry Phos Binder, there is a non-linear trend with serum Ca, where Ca levels decline around +20 mEq/100 g DM, but increase at either +10 or +40 mEq/100 g DM;
- whereas Al-DCAD demonstrates the most pronounced improvement, raising serum Ca from 8.6 to 9.0 mg/dL as DCAD decreases from +10 to −20 mEq/100 g DM, with the better serum Ca effect as DCAD decreases from 0 to −20 mEq/100 g DM. This underscores Al-DCAD's unique efficacy in combining phosphorus binding with controlled DCAD modulation to optimize sustained calcium homeostasis postpartum, minimizing hypocalcemia in dairy cows without inducing toxicity or metabolic disturbances.

Reducing DCAD from +10 to −30 mEq/100 g of DM increases serum Ca (average first 4 DIM) from 8.3 to 8.6 mg/dL in cows fed Anionic diets. Reducing DCAD in cows fed Dry Phos Binder has no effect until DCAD drops below +20 mEq/100 g DM. Lowering DCAD below +20 mEq/100 g DM increases serum Ca in cows fed Dry Phos Binder (DIM=1-4) a quite different response than DIM=1-2. However, the Al-DCAD group consistently results in the highest serum Ca outcomes in both DIM evaluations. Reducing DCAD from +10 mEq to −20 mEq/100 g of DM increases serum Ca to the highest levels, from 8.6 to 9.0 mg/dL in cows fed Al-DCAD strategy DIM 1-4.

These controlled findings align with real-world field data, where switching to Al-DCAD strategies has led to measurable reductions in health disorders like milk fever, mastitis, and culling rates across multiple dairies.

Field Incidence of Milk Fever Across Dairies

FIG. 31 A-C are graphs showing milk fever incidence by month for multiparous cows across 3 different dairies (A, B, and C).

More particularly, FIG. 31 A-C are graphs showing milk fever incidence by month for multiparous cows across 3 different dairies (A, B, and C). These graphs show response of three herds in the field supplemented with Anionic strategy and after they started the Al-DCAD strategy. Monthly incidence of milk fever ranged from 0% up to 6.0% and averaging about 2.2% when cows were fed the Anionic strategy. In the period since starting feeding the cows the Al-DCAD strategy, average milk fever rates have ranged from 0 to below 2% and averaging less than 1%. These figures evidence a substantial reduction in milk fever incidence following the transition from Anionic diets to Al-DCAD formulations, demonstrating the efficacy of the disclosed total dietary compositions in improving postpartum metabolic health and reducing clinical hypocalcemia risks in multiparous dairy cows across diverse commercial dairy operations.

Health and Productivity Outcomes Post-Transition

FIG. 32 is a bar chart comparing mastitis incidence in multiparous cows less than 60 days in milk (DIM) after switching from Anionic (aka ANI) to Al-DCAD treatments.

More particularly, FIG. 32 is a bar chart comparing mastitis incidence in multiparous cows less than 60 days in milk (DIM) after switching from Anionic (aka ANI) to Al-DCAD treatments. Mastitis incidence<60 DIM declined from 10.80% (109,234 calvings) in herds fed Anionic diets to 8.43% (28,913 calvings) after these herds started feeding the Al-DCAD strategy. This is a reduction in mastitis events by 22%. This figure evidences a notable reduction in early lactation mastitis rates following the adoption of Al-DCAD diets, suggesting improved immune function and udder health in multiparous cows during the critical transition period, potentially attributable to the combined phosphorus-binding and mild acidification effects of the disclosed dietary compositions.

FIG. 33 is a bar chart showing mastitis incidence in multiparous cows less than 60 days in milk (DIM) after switching from Dry Phos Binder to Al-DCAD treatments.

More particularly, FIG. 33 is a bar chart showing mastitis incidence in multiparous cows less than 60 days in milk (DIM) after switching from Dry Phos Binder to Al-DCAD treatments. In herds fed Dry Phos Binder, the incidence declined from 14.57% (52,487 calvings) to 5.63% (9,677 calvings) after switching to the Al-DCAD diet. This figure evidences a notable reduction in early lactation mastitis rates by 61% following the adoption of Al-DCAD diets, suggesting improved immune function and udder health in multiparous cows during the critical transition period, potentially attributable to the combined phosphorus-binding and mild acidification effects of the disclosed dietary compositions.

FIG. 32 and FIG. 33 evidence a substantial decrease in mastitis occurrence in early lactation multiparous cows upon transitioning to Al-DCAD formulations, highlighting the superior immunomodulatory benefits of the invention's integrated approach to phosphorus management and DCAD control compared to standalone anionic diets and dry phosphorus binders.

FIG. 34 is a bar chart comparing died and sold rates for multiparous cows less than 60 days in milk (DIM) after switching from Anionic to Al-DCAD treatments.

More particularly, FIG. 34 is a bar chart comparing died and sold rates for multiparous cows less than 60 days in milk (DIM) after switching from Anionic to Al-DCAD treatments. This summary of 32 farms shows that Died and Sold<60 DIM decreased from 9.76% (103,160 calvings) to 8.07% (31,073 calvings) when dairy farms switched from feeding cows an only anionic diet to an anionic diet with P binding capabilities (Al-DCAD). This is a reduction of died and sold outcomes by 17%, indicating that the combination of the strategies work better than the individual strategy. This figure evidences improved early postpartum survival and retention rates in multiparous cows following the implementation of Al-DCAD diets, demonstrating the practical on-farm benefits of the disclosed compositions in reducing culling and mortality associated with transition cow disorders.

FIG. 35 is a bar chart comparing died and sold rates for multiparous cows less than 60 days in milk after switching from Dry Phos Binder to Al-DCAD treatments.

More particularly, FIG. 35 is a bar chart comparing died and sold rates for multiparous cows less than 60 days in milk after switching from Dry Phos Binder to Al-DCAD treatments. This summary of 7 farms shows that Died and Sold <60 DIM decreased from 9.66% (52,547 calvings) to 7.79% (9,678 calvings) when dairy farms switched from feeding cows an only Dry Phos Binder diet to an anionic diet with P binding capabilities (Al-DCAD). This is a reduction in died and sold outcomes by 19%, indicating that the combination of the strategies work better than the individual strategy. This figure evidences enhanced cow longevity and reduced early lactation losses in multiparous animals after adopting Al-DCAD strategies, underscoring the synergistic advantages of the invention's phosphorus-binding elements combined with controlled DCAD over conventional dry phosphorus binder approaches.

FIG. 36 is a bar chart comparing milk fever incidence rates for multiparous cows after switching from Anionic (aka ANI) to Al-DCAD treatments.

More particularly, FIG. 36 is a bar chart comparing milk fever incidence rates for multiparous cows after switching from Anionic (aka ANI) to Al-DCAD treatments. Summary of 20 farms shows that incidence of milk fever decreased from 2.24% (109,009 calvings) to 1.56% (27,633 calvings) when dairy farms switched from feeding cows an only anionic diet to an anionic diet with P binding capabilities (Al-DCAD). This is a reduction in milk fever outcomes by 30%, indicating that the combination of the strategies works better than the individual strategy. This figure evidences a significant decline in clinical hypocalcemia cases among multiparous cows transitioning to Al-DCAD diets, illustrating the effectiveness of the disclosed total dietary compositions in mitigating milk fever through optimized mineral balance and metabolic support.

FIG. 37 is a bar chart comparing milk fever incidence rates for multiparous cows after switching from Dry Phos Binder to Al-DCAD treatments.

More particularly, FIG. 37 is a bar chart comparing milk fever incidence rates for multiparous cows after switching from Dry Phos Binder to Al-DCAD treatments. This summary of 6 farms shows that milk fever incidence was very similar when dairy farms switched from feeding cows an only Dry Phos Binder diet 1.49% (50,419 calvings) to an anionic diet with P binding capabilities (Al-DCAD) 1.41% (13,427 calvings), a reduction in milk fever by 5%, indicating that both are effective at controlling milk fever incidence to a similar level. This figure evidences comparable efficacy between Al-DCAD and Dry Phos Binder in controlling milk fever rates, while potentially offering additional benefits in other health metrics, supporting the versatility of the invention's formulations in managing periparturient calcium disorders.

In addition to health improvements, these strategy transitions have positively influenced productivity, particularly in terms of early lactation milk yield.

FIG. 38 is a bar chart comparing daily milk yield by day in multiparous cows after switching from Dry Phos Binder to Al-DCAD treatments.

More particularly, FIG. 38 is a bar chart comparing daily milk yield by day in multiparous cows after switching from Dry Phos Binder to Al-DCAD treatments. The milk yield data is reported over the first 4 weeks of milk. The data is extracted from dairy farm record software. The Dry Phos Binder category is averaging milk yield of multiparous cows at 7, 14, 21 and 28 days in milk for the same period of time in the year prior to switching to Al-DCAD. All 6 of these herds were on a Dry Phos Binder during this time. The Al-DCAD is average milk yield for multiparous cows once the herd switched to feeding Al-DCAD at 7, 14, 21 and 28 days. Milk yield increased in herds the first 4 weeks in milk when they switched to Al-DCAD from Dry Phos Binder. This figure evidences improved early lactation productivity in multiparous cows following the adoption of Al-DCAD diets, indicating better transition success and metabolic health as reflected in enhanced milk production during the critical first month postpartum.

Milk yield is multifactorial, but milk yield over the first 4 weeks of lactation are understood to be indicative of a cows success through the transition period. Cook, J. G., P. T. Pepler, L. Viora, and D. L. Hill. 2024. Assessing transition cow management in dairy cows for improved health, milk production, pregnancy, and culling outcomes. Journal of Dairy Science 107:11381-11397.

Inflammation Thresholds and Transition Success

FIG. 39 is an illustration graphing the effects of lower or higher fibroblast growth factor 23 (FGF23) on inflammation and homeostasis in dairy cows.

Bradford et al. (2015) reported that repeated inflammatory insults even at low doses alter metabolic homeostasis once immune signaling cascade reaches a certain threshold. The concentration of FGF23 in the blood can change by the level of dietary P and the immune response of the cows. The magnitude of the signaling response can influence the risk of reaching the signaling threshold. Without being limited by any theory, it is theorized, that higher dietary P and frequency of insults increases the risk of altering homeostasis by increasing FGF23. Managing the level of FGF23 reduces the risk of altering homeostasis around calving. Bradford, B. J., K. Yuan, J. K. Farney, L. K. Mamedova, and A. J. Carpenter. 2015. Invited review: Inflammation during the transition to lactation: New adventures with an old flame. Journal of Dairy Science 98:6631-6650.

FIG. 40 is a diagram linking dry matter intake and nutrient absorption, mineral metabolism, and immune regulation to transition success in dairy cows. Transition from a dry cow to a successful lactation cow involves many hormonal, metabolic and immune responses. The successful transition is highly dependent on an orchestrated effort among the organs that manage mineral metabolism, the gastrointestinal tract ability to process and absorb nutrients while maintaining its integrity and the ability of the immune system to have a controlled inflammation response around calving.

These integrated metabolic and immune insights underscore the key benefits of the Al-DCAD strategy in enhancing phosphorus binding, DCAD control, and overall cow health.

Key Benefits of Al-DCAD Strategy

Al-DCAD provides more efficient binding of phosphorus, in various preferred embodiments replaces some protein, and contributes to desirable range of DCAD.

Al-DCAD improves fresh cow health and Ca status along with lowering MF incidence.

Various Preferred Embodiments

Leveraging these benefits, the following embodiments detail preferred formulations and methods for implementing the Al-DCAD total dietary compositions in practice.

According to an embodiment, a total dietary composition (TDC) for dairy cows is provided, the TDC comprising:

(A) a basal diet; and (B) a supplemental source of one or more phosphorus-binding elements comprising one or more chemical sources of aluminum(III);

wherein the TDC has:

(i) a phosphorus-to-aluminum weight ratio of 1.5:1 to 2.5:1 based on total dietary phosphorus and aluminum from the chemical sources of aluminum(III), measured on a dry matter basis; and (ii) a Dietary Cation-Anion Difference (DCAD) of −15 to +10 mEq/100 g dry matter calculated as ([Na]+[K])—[Cl]+[S]).

In various embodiments, the TDC has a preferred phosphorus-to-aluminum weight ratio of 1.5:1 to 2.3:1 based on total dietary phosphorus and aluminum from the chemical sources of aluminum(III), measured on a dry matter basis.

According to another embodiment, a total dietary composition (TDC) for dairy cows is provided, the TDC comprising:

(A) a basal diet; and (B) a supplemental source of one or more phosphorus-binding elements comprising one or more chemical sources of aluminum(III);

wherein the TDC has:

(i) a phosphorus-to-(aluminum times calcium) weight ratio of 1.8:1 to 4.0:1 based on total dietary phosphorus, aluminum from the one or more chemical sources of aluminum(III), and total dietary calcium, measured on a dry matter basis; and (ii) a Dietary Cation-Anion Difference (DCAD) of −15 to +10 mEq/100 g dry matter calculated as ([Na]+[K]H—[Cl]+[S]).

In various embodiments, the TDC has a preferred phosphorus-to-(aluminum times calcium) weight ratio of 1.8:1 to 3.0:1 based on total dietary phosphorus, aluminum from the one or more chemical sources of aluminum(III), and total dietary calcium, measured on a dry matter basis.

According to yet another embodiment, a total dietary composition (TDC) for dairy cows is provided, the TDC comprising:

(A) a basal diet; and (B) a supplemental source of one or more phosphorus-binding elements selected from the group consisting of:

(i) one or more chemical sources of aluminum(III), (ii) one or more chemical sources of iron (II), iron(III), and any combination thereof, and (iii) any combination thereof;

wherein the TDC has:

(a) a phosphorus-to-binding-elements stoichiometric ratio of 1.3:1 to 2.2:1 based on total dietary phosphorus and the molar binding capacity of the phosphorus-binding elements from the supplemental source; and (b) a Dietary Cation-Anion Difference (DCAD) of −15 to +10 mEq/100 g dry matter calculated as ([Na]+[K])—[Cl]+[S]).

In various embodiments, the TDC has a preferred phosphorus-to-binding-elements stoichiometric ratio of 1.3:1 to 2.0:1 based on total dietary phosphorus and the molar binding capacity of the phosphorus-binding elements from the supplemental source.

In various embodiments, at least one chemical source of aluminum(III) has a characteristic of dissolving or decomposing in 0.1 M HCl to at least 1 mole of Al/L as determined without stirring after 2 hours at 20° C.

In various embodiments, at least one chemical source of aluminum(III) is a zeolite.

In various embodiments, at least 50% of the aluminum from the chemical sources of aluminum(III) is from one or more chemical sources of aluminum(III) having a characteristic of dissolving or decomposing in 0.1 M HCl to at least 1 mole of Al/L as determined without stirring after 2 hours at 20° C. Zeolites are not so soluble in such a weak acid.

In various embodiments, at least 90% of the aluminum from the chemical sources of aluminum(III) is from one or more chemical sources of aluminum(III) having a characteristic of dissolving or decomposing in 0.1 M HCl to at least 1 mole of Al/L as determined without stirring after 2 hours at 20° C.

In various embodiments, the one or more chemical sources of aluminum(III) comprise aluminum(III) compounds selected from the group consisting of aluminum sulfate, aluminum chloride, aluminum carbonate, aluminum hydroxide, and any combination thereof.

In various embodiments, the chemical sources of aluminum(III) are at concentrations non-toxic to dairy cows, as determined by NRC guidelines.

In various embodiments, the supplemental source of phosphorus-binding elements comprises one or more chemical sources of iron (II), iron(III), and any combination thereof.

In various embodiments, each chemical source of iron(III) has a characteristic of dissolving or decomposing in 0.1 M HCl to at least 1 mole of Fe/L as determined without stirring after 2 hours at 20° C.

In various embodiments, the one or more chemical sources of iron comprise one or more iron(III) compounds selected from the group consisting of iron(III) sulfate, iron (III) chloride, and any combination thereof.

In various embodiments, the concentration of iron(III) from the supplemental source of phosphorus-binding elements in the TDC is at most 250 ppm on a dry matter basis.

In various embodiments, the total iron(II) and iron(III) concentration in the TDC is up to 1,000 ppm on a dry matter basis.

In various embodiments, chemical sources of iron are at concentrations non-toxic to dairy cows, as determined by NRC guidelines.

In various embodiments, the TDC has a preferred DCAD of −15 to 0 mEq/100 dry matter calculated as ([Na]+[K])—[Cl]+[S]).

In various embodiments, the TDC comprises one or more ingredients selected from the group consisting of: non-protein nitrogen; cane molasses; condensed molasses solubles; a clay; and water.

In various embodiments, the non-protein is selected from the group consisting of urea, ammonium sulfate, ammonium chloride, biuret [($C_2H_5N_3O_2$)], and ammonium bicarbonate, and any combination thereof.

In various embodiments, the non-protein nitrogen comprises urea.

In various embodiments, the non-protein nitrogen provides up to 33% of the measured crude protein in the TDC.

In various embodiments, the TDC comprises:

(a) a basal diet; and (b) a supplement for the basal diet, wherein the supplement comprises at least a portion of the chemical sources of aluminum(III).

In various embodiments, the supplement comprises ingredients selected from the group consisting of: at least some of the one or more chemical sources of iron (II), iron(III), and any combination thereof, non-protein nitrogen; cane molasses; condensed molasses solubles; a clay; and water.

In various embodiments, the supplement is in the form of a liquid or a liquid suspension.

In various embodiments, with feeding of the TDC to closeup dairy cows, the TDC maintains the serum phosphorus of the dairy cows in a range of 3.6 to 4.6 mg/dL.

In various embodiments, with feeding of the TDC to prepartum dairy cows, the TDC maintains the serum phosphorus of the dairy cows in a preferred range of 3.6 to 4.2 mg/dL.

In various embodiments, with feeding of the TDC for closeup dairy cows, the TDC reduces the incidence of milk fever in multiparous cows by at least 30% relative to anionic strategies without the one or more phosphorus-binding elements.

In various embodiments, with feeding of the TDC for closeup dairy cows, the TDC reduces the incidence of died and sold cows within 60 days postpartum by at least 17% relative to anionic strategies without the one or more phosphorus-binding elements and 19% relative to Dry Phos Binder strategies with phosphorus-binding elements.

In various embodiments, A method of feeding prepartum dairy cows is provided, the method comprising a step of feeding the cows the TDC according to any of the various embodiments.

In various embodiments, a step of measuring one or more of effects selected from the group consisting of:

(a) serum P;

(b) serum Ca;

(c) milk fever incidence, (d) mastitis incidence;

(e) died and sold cows;

(f) milk yield in first 4 weeks of lactation; and (g) any combination thereof.

In various embodiments, any of the methods comprise the steps of:

(a) obtaining serum phosphorus data measured periodically for the closeup dairy cows;

(b) comparing the serum phosphorus data to a desired target range of serum phosphorus; and (c) recommending an adjustment to the amount of phosphorus-binding elements in the TDC based on the comparison.

In various embodiments, the target range of serum phosphorus is 3.6 to 4.6 mg/dL as determined by a colorimetric method.

In various embodiments, the adjustment comprises increasing the amount of phosphorus-binding elements if the serum phosphorus data exceeds the upper limit of the desired target range or decreasing the amount of phosphorus-binding elements if the serum phosphorus data falls below the lower limit of the desired target range.

In various embodiments, a dietary supplement composition for dairy cows is provided, the supplement comprising one or more chemical sources of aluminum(II) configured to bind phosphorus in a dairy cow diet, wherein the supplement is formulated to contribute to a total dietary composition having:

(a) a phosphorus-to-supplemental aluminum weight ratio of 1.5:1 to 2.5:1, based on total dietary phosphorus and aluminum from the chemical sources of aluminum(III), measured on a dry matter basis; and (b) a Dietary Cation-Anion Difference (DCAD) of −15 to +10 mEq/100 g dry matter, calculated as ([Na]+[K])—[Cl]+[S]).

In various embodiments, a dietary supplement composition for dairy cows is provided, the dietary supplement composition comprising: one or more chemical sources of aluminum(III) configured to bind phosphorus in a dairy cow diet, wherein the supplement is formulated to contribute to a total dietary composition having:

(a) a phosphorus-to-(aluminum times calcium) weight ratio of 1.8:1 to 4.0:1 based on total dietary phosphorus, aluminum from the one or more chemical sources of aluminum(III), and total dietary calcium, measured on a dry matter basis; and (b) a Dietary Cation-Anion Difference (DCAD) of −15 to +10 mEq/100 g dry matter calculated as ([Na]+[K])—[Cl]+[S]).

In various embodiments, a dietary supplement composition for dairy cows is provided, the dietary supplement composition comprising: one or more phosphorus-binding elements configured to bind phosphorus in a dairy cow diet, wherein the phosphorus-binding elements are selected from the group consisting of:

(i) one or more chemical sources of aluminum(III), (ii) one or more chemical sources of iron (II), iron(III), and any combination thereof, and (iii) any combination thereof; and wherein the supplement is formulated to contribute to a total dietary composition having:

(a) a phosphorus-to-binding-elements stoichiometric ratio of 1.3:1 to 2.2:1 based on total dietary phosphorus and the molar binding capacity of the phosphorus-binding elements from the supplemental source; and (b) a Dietary Cation-Anion Difference (DCAD) of −15 to +10 mEq/100 g dry matter calculated as ([Na]+[K])—[Cl]+[S]).

In various embodiments, the ranges or target ranges are critical.

Interpretation, Definitions, and Usages

Principles of Interpretation

The words, terms, phrases, and other symbols used herein have their plain, ordinary meaning to persons of skill in the art of this disclosure, except to the extent explicitly and clearly defined in this disclosure, on the condition that even if explicitly defined in this disclosure, the specific context of a usage could still require a different or more specific meaning. All possible relevant senses of the multitude of words used in this disclosure may not be accounted for in a specific provided definition. The applicable sense or senses can depend on the specific context of the usage.

Initially, as a general aid to interpretation, the possible definitions of the words, phrases, and other symbols used herein are intended to be interpreted by reference to comprehensive general dictionaries of the English language published before or about the time of the earliest filing of this application for patent. A preferred dictionary is the American Heritage Dictionary of the English Language, 5$^{th}$ Edition (Houghton Mifflin Harcourt, 2019). Where several different general definitions are available, it is intended that the broadest definitions or senses be selected that are consistent with this disclosure and the description of the presently most-preferred embodiments, including without limitation as shown in a figure of any drawing.

After initially consulting such general dictionaries of the English language, it is intended that the words, phrases, or other symbols used herein be further interpreted or the most appropriate general definition or definitions be further selected by consulting technical dictionaries, encyclopedias, treatises, or relevant prior art to which the claimed invention pertains. If necessary to resolve any remaining doubt, utilizing the patent prosecution record may be helpful to select from among the possible interpretations.

Terms or phrases made up of more than one word (for example, compound terms or phrases or names) are sometimes not found in general dictionaries of the English language. Compound terms or names are to be interpreted as a whole, and not by parsing the separate words of the compound term, which might result in absurd and unintended interpretations. For example, in the context of railroad technology, a "coal car" does not mean a car made of coal but is well understood to mean the railroad car is for hauling coal. In general, compound terms are to be interpreted as they would be understood in the art and consistent with the usage in this specification.

Examining relevant general dictionaries, encyclopedias, treatises, prior art, and the patent record will make it possible to ascertain the appropriate meanings that would be attributed to the words and terms of the description and claims by those skilled in the art, and the intended full breadth of the words and terms will be more accurately determined. In addition, the improper importation of unintended limitations from the written description into the claims will be more easily avoided.

If there is any conflict in the usages of a word or term in this disclosure and one or more patent(s) or other documents that are incorporated by reference, the definitions that are consistent with the original material of this disclosure should be adopted in interpreting the original material of this disclosure, and the definitions that are consistent with the document incorporated by reference should be adopted in interpreting the material from that document.

Words of language often have multiple different senses. The selection of the applicable sense is usually understood from the particular context in which the word is used. If a word is specifically defined herein in a particular sense that does not reasonably apply in the context of a particular instance of usage elsewhere in the disclosure or claims, an applicable sense definition should be applied, not an inapplicable definition for a different context of usage. If any explicit definition herein is plainly obnoxious both to every ordinary meaning and to every technical meaning in the art for a usage in a particular context, the explicit definition herein should be disregarded as an obvious and unintended error.

It should be understood that an element, part, component, or ingredient can have more than one characteristic and that it can be characterized or classified in different, independent respects.

The headings and subheadings used in herein are intended for convenient reference but are not intended to be limiting.

Patent Terminology

"Art" (noun) a field or branch of technology, applied knowledge, or practical skill, particularly in patent law referring to the body of existing information, techniques, and practices relevant to an invention, including the prior art which encompasses publicly available disclosures in that field.

A patent "claim" (noun) means either: (a) a statement of the subject matter for which legal protection is sought in an application for patent; or (b) a statement of the subject matter for which legal protection has been granted (that is, legally recognized) in an issued patent. A patent claim is distinguishable from other types of legal claims and distinguishable from non-legal claims, such as factual or medical claims.

"Disclosure" (noun) (of an application for patent) means the specification of the written description with any original claims and any drawings, as of the effective filing date of the subject matter of a claim. The purpose of the disclosure is to disclose, that is, to make known. The applicable national law may provide a more particular definition or requirements for a disclosure of a patent.

"Drawing" (noun) means: (1) the act or an instance of drawing; or (2) (a) the art of representing objects or forms on a surface chiefly by means of lines; (b) a work produced by this art. In a patent, a "drawing" may comprise one or more figures.

"Figure" or "FIG." (noun) means an individual illustration, diagram, or representation within the drawings of a patent application or patent, used to depict aspects of the invention such as structures, processes, embodiments, or formulas, and typically labeled sequentially for reference in the specification.

An "original claim" (noun phrase) of a patent is a claim that is filed at the time of filing an application. An original claim is also part of the original disclosure. For the purposes of disclosure, an original claim can be treated as disclosure; however, for the purposes of examination of patentability and interpretation of full scope of an issued patent, any claim should be interpreted as broadly as literally stated except for any obvious error or except as may be interpreted under the doctrine of equivalents. For the purposes of disclosure, all variations, combinations, and permutations in which one or more limitations, elements, clauses, and descriptive terms from one or more of the original claims is introduced into another original claim are part of the disclosure. For example, any original claim that is dependent on another original claim can be amended to include one or more limitations found in any other original claim that is dependent on the same original base claim.

"Patent" (noun) means: (1) a grant made by a government that confers upon the creator (or assignee) of an invention the right to exclude others from making, using, offering to sell, selling, or importing that invention within the territory of the government for a limited period of time; (b) letters patent; or (c) an invention protected by such a patent. The applicable national law may provide more particular requirements. The applicable national law may provide a more particular identification of the patent rights.

"Prior art" (noun) means any evidence or information that was publicly available, disclosed, or known to the public before the effective filing date of a patent application, which may include patents, publications, products, or other disclosures, and is used to assess the novelty or non-obviousness of an invention.

"Specification" (noun) means a written description of the ideas in an application or patent. The applicable national law may provide a more particular definition or requirements for a specification.

Transitional Terminology

The words "comprising," "containing," "including," "having," "characterized by," and all grammatical variations thereof are intended to have an open, non-limiting meaning as to any unstated limitations.

In a claim, the transitional term "comprising," is inclusive or open-ended and does not exclude additional, un-recited elements or method steps. "Comprising" in claim language means the specified elements are essential, but other elements can be added and still form a construct within the scope of the claim. For example, a composition comprising an ingredient does not exclude it from having additional ingredients, an apparatus comprising a part does not exclude it from having additional parts, and a method having a step does not exclude it having additional steps.

In a claim, the transitional phrase "consisting essentially of" and all grammatical variations thereof are intended to limit the scope of a claim to the specified materials or steps and those that do not materially affect the basic and novel characteristic(s) of the claimed invention. A "consisting essentially of" claim occupies a middle ground between fully open claims using a "comprising" format and closed claims that are written in a "consisting of" format.

In a claim, the transitional phrase "consisting of" excludes any element, step, or ingredient not specified in the claim. For example, "consisting of" is defined as closing the claim to the inclusion of materials other than those recited except for impurities ordinarily associated therewith. For another example, a claim for a bone repair kit "consisting of" certain chemicals in a claim was infringed by a bone repair kit including a spatula in addition to the claimed chemicals because the presence of the spatula was unrelated to the subject matter of the claimed invention.

The phrase "selected from the group consisting of" (which is a kind of "Markush" grouping) means a list of alternative species within a grouping, even if the list includes the word "and." For example, "selected from the group consisting of: a, b, and c" means any one or more of "a, b, and c". Unless otherwise stated, the group can be, for example, any one or more of "a, b, and c" in any proportion.

For the purposes of disclosure, however, such transitional phrases additionally subsume and include a disclosure of any more limited meanings. For example, a disclosure using the word "comprising" or like open-ended terms herein is intended to support a claim using any of the transitional terms "comprising," "consisting essentially of," or "consisting of." Similarly, a disclosure using the phrase "consisting essentially of" is intended to support a claim using the narrower phrase "consisting of."

Other Grammar

The indefinite articles "a" or "an" mean at least one of the noun or noun phrase that the article introduces.

The conjunction "and" (in the sense of a listing or grouping) is open to additional elements or steps, unless the context otherwise requires.

"Or" (conjunction) means: (1) (a) indicating an alternative, usually only before the last term of a series: hot or cold; this, that, or the other; (b) indicating the second of two alternatives, the first being preceded by either or whether; or (2) indicating a synonymous or equivalent expression.

For the purposes of disclosure, conjunctions "or" (in the sense of an alternative) and "and" (in the sense of a listing or grouping) can be interpreted first as open and non-limiting to other or additional possibilities, and, interpreted second, as closed and limiting.

For the purposes of disclosure, where elements are presented as groups or lists, for example, in "Markush group" format, each and every possible subgrouping of the grouped or listed elements is also disclosed as if set forth in separate lists. For example, where a disclosed group of three elements is disclosed, any subgrouping of one or two of the three elements is disclosed. For the purposes of disclosure, in various embodiments exactly one member of a group is present in, employed in or otherwise relevant to a given product or process. In various embodiments one, more than one, or all of a group's members are present in, employed in, or otherwise relevant to a given product or process.

The phrase "one or more" of something means an alternative grouping of the something.

"Phrase" (noun) means a sequence of two or more words that have meaning, especially when forming part of a sentence. "Noun phrase" means a phrase formed by a noun and all its modifiers and determiners; broadly any syntactic element (such as a clause, clitic, pronoun, or zero element) with a noun's function (such as the subject of a verb or the object of a verb or preposition), for example, the phrase "coal car" for which the head is the noun "car." A noun phrase can be replaced by a single pronoun without rendering the sentence grammatically unacceptable.

In a "positive" (inclusionary) statement of a patent claim, an alternative grouping is met if any one or more of the statements of the grouping are met.

In a "negative" (exclusionary) statement of a patent claim, however, an alternative grouping is met only if all the statements of the grouping are met.

General Terminology

"Alternative" (adjective) means allowing for a choice between two or more things from which the choice can be made.

"Avoid" (verb) means to refrain from using or doing something.

"Capable" (adjective) means having capacity or ability.

"Capacity" (noun) means the ability or extent of an ability, for example to receive, hold, dissolve, or absorb something or means the maximum amount that can be contained, held, dissolved, or absorbed, depending on the context.

"Carrier" (noun) means a mechanism, device, or composition by which something is conveyed or conducted.

"Characteristic" (noun) means a feature that helps to identify, tell apart, or describe recognizably, for example, a distinguishing mark, trait, or property.

"Combine" (verb) means to bring into a state of unity, to make united, as in to combine ingredients of a recipe.

"Combination" (noun) means the state or result of things being united.

"Component" (noun) means a constituent element or part, as of a system or composition.

"Composition" (noun) means the makeup of a substance or means the result or product of combining or mixing, depending on the context. Of course, a "composition" does not include a container or vessel for mixing, containing, storing, or delivering the composition. In addition, a "composition" does not include any applicator, such as an absorbent solid material (for example, a patch or swab), for applying the composition. A "composition" can be a mixture of ingredients, which may or may not have undergone any chemical reaction.

"Condition" (noun) means: (1) a mode or state of being; or in logic (2) a proposition on which another proposition depends; the antecedent of a conditional proposition.

"Content" (noun) means the proportion of a specified substance or material in a whole.

"Control" (noun) means a comparison for checking or verifying the results of a test or scientific experiment or means a mechanism or other input that controls the operation of a machine, computer device, or process.

"Control" (verb) means to adjust to a requirement.

"Efficacious" (adjective) means producing or capable of producing a desired effect.

"Efficacy" (noun) means power or capacity to produce a desired effect; effectiveness.

"Element" (noun) means a fundamental, essential, or irreducible constituent of a composite entity. In chemistry and physics, an element is a substance composed of atoms having an identical number of protons in each nucleus. Elements cannot be reduced to simpler substances by normal chemical means. See the periodic table of the elements.

"Embodiment" (noun) means a concrete or embodied form of an abstract concept.

"Especially" (adverb) means to an extent or degree deserving of special emphasis; particularly, but not necessarily so limited.

"Essential" (adjective) means constituting or being part of the fundamental nature or essence of something.

"Essentially" (adverb) means constituting or being part of the fundamental nature or essence of something.

In chemistry, "formula" (noun) means a symbolic representation of the elemental or moiety composition of a chemical compound or of the composition and structure of a compound.

In compositions, "formula" (noun) means a specification or prescription of ingredients in fixed proportion; a recipe.

"Formulation" (noun) means the resultant composition of being prepared according to a specified formula.

"General" (adjective) means: (1) affecting or characteristic of the majority of those involved; or (2) involving only the main feature or features rather than precise or particular details.

"Improvement" (noun) means: (1) (a) the act or process of improving; or (b) the state of being improved; or (2) a change or addition that improves.

"Ingredient" (noun) means an element or component of something, usually something that enters as an element or a component into a mixture or composition. An "ingredient" can be used to form a first composition, such as supplement, and then the first composition can be used as an "ingredient" for a second composition, such as a total dietary composition.

"Insignificant" means the opposite of significant.

"Method" (noun) means a manner or way of doing something, especially a structured or systematic way of accomplishing something.

"Minimize" (verb) means to reduce to a smaller or the smallest possible amount, extent, size, or degree as can be practical in the relevant context.

"Mix" (verb) means: (a) to combine or blend into one mass or mixture; (b) to form by combining ingredients; or (c) to add an ingredient or element to another.

"Mixture" (noun) means (1) the act or process of mixing; (2) the condition of being mixed; or (3) something produced by mixing, which may or may not be chemically combined with each other.

"Portion" (noun) means something determined in relation to something that includes it.

"Process" (noun) means: (1) a series of actions, changes, or functions bringing about a result; (2) a series of operations performed in the making or treatment of a product, for example, a manufacturing process; or (3) a process, art, or method, and includes a new use of a known process, machine, manufacture, composition of matter, or material.

"Provide" (verb) means to furnish, supply, make available, or prepare. It can include making available to oneself. It does not require, but can include two or more individuals or actors, that is, it can include, but does not require a provider and a recipient.

"Select" (verb) means to choose from two or more alternatives.

"Significant" (adjective) means relatively large in importance, value, degree, amount, or extent in the relevant context.

"Step" (noun) means one of a series of actions, processes, or measures taken to achieve a goal or purpose.

"Substantial" (adjective) and "substantially" (adverb) mean considerable in importance, value, degree, amount, or extent in the relevant context. "Substantial" is more, as a matter of degree, than "significant."

"System" (noun) means a group of interacting, interrelated, or interdependent elements forming a complex whole.

"Unit" (noun) means an individual, group, structure, or other entity regarded as an elementary structural or functional constituent of a whole, for example, a mechanical part or module; in another sense can mean an entire apparatus or the equipment that performs a specific function.

"Use" (verb) means to put into service; to make work or employ something for a particular purpose or for its inherent or natural purpose.

"Usage" (noun) means the act of using, including usage data such as start time, end time, duration, type of activity, and intensity.

"Various" (adjective) means of diverse kinds purposefully arranged or grouped but not requiring uniformity.

"In various embodiments" (phrase) means one or more of various embodiments have the step, element, or attribute, but not all necessarily have it. Any of the various embodiments can be combined with any other of the various embodiments insofar as can be practical and non-contradictory to each other.

Numbers, Numerical Limits, Numerical Ranges, and Percentages, and Pluralities

"About" or "approximately" (adverbs) when used with a stated value x (where x has n significant figures), indicate that the value falls within the range from $(x-\delta)$ to $(x+\delta)$. Here, $\delta$ is equal to half the place value of the last significant figure in x. For example, "about 4.5" has 2 significant figures (4 and 5). The last significant figure is 5, in the tenths place (place value=0.1). Therefore, δ=half of 0.1=0.05. This would mean the value lies within the interval 4.5±0.05, that is, from 4.45 to 4.55.

"By weight" (adverbial phrase) means according to weight rather than volume or other measure. A concentration by weight can be expressed as a "weight percent" or as a proportion "weight/weight" or abbreviated to "w/w". For example, "by weight" or "w/w" means by weight of the composition.

"Ratio" (noun) means the quantitative relation between two amounts, expressed as the quotient of one divided by the other, such as in weights, moles, or concentrations.

"Weight ratio" (noun phrase) the proportion of the weights of two or more substances, elements, or components in a composition, expressed as a quotient or in the form a:b, where a and b are numerical values representing their respective weights.

Where a numerical limit of degree or measurement is disclosed, any number and any limit falling within the expressly stated limit is also intended to be specifically disclosed. For example, every expressly stated limit (in the form of "less than a" or "at most a" or "greater than b" or "at least b" or any similar expressions, where "a" and "b" represent numerical values of degree or measurement) is to be understood to set forth every number encompassed by the expressly stated numerical limit. For example, "less than 10" is understood to additionally disclose "less than 9.97," "less than 7.2," "less than 0.001," "zero," and, if physically possible in the context, negative numbers, such as "less than minus 29.3."

Where a numerical range of degree or measurement with a lower limit and an upper limit is disclosed, any number and any range falling within the expressly stated numerical range is also intended to be specifically disclosed. Furthermore, unless otherwise indicated or otherwise evident from the context and understanding of one of ordinary skill in the art, values that are expressed as ranges can assume any specific value or sub-range within the stated range, to the hundredth of the unit of the range, unless the context clearly dictates otherwise. For example, every expressly stated numerical range of values (in the form "a to b," or "about a to about b," or "about a to b," or "approximately a to b," or any similar expressions, where "a" and "b" represent numerical values of degree or measurement) is to be understood to set forth every number and range encompassed in the expressly stated numerical range. For example, an expressly stated disclosure of "in the range of 10 to 20" is understood to additionally disclose, for example, "10," and "10 to 10.01," and "11.3," and "14 to 16.95," and "16.4 to 18.6," and "17.43 to 19.7," and "20."

Where a numerical limit is disclosed as a percentage of degree or measurement as a portion of a whole, it is based on the percentage range of 0% (zero or none of the whole) to 100% (all of the whole). For example, every expressly stated numerical limit of a percentage (in the form of "less than a %" or "at most a %" or "greater than b %" or "at least b %" or any similar expressions, where "a" and "b" represent numerical values of the percentage) is to be understood to set forth every number encompassed by the expressly stated limit from 0 (zero) to "a" or from "b" to 100, as indicated by the percentage context, except, however, that the lower limit of none or the upper limit of 100% may be otherwise limited by other requirements of the claim. For example, in a composition comprising "at least 10% by weight of a first ingredient," "at least 20% by weight of a second ingredient," and "less than 30% by weight of a third ingredient," it should be understood the first ingredient can be in the range of 10-80% by weight, the second ingredient can be in the range of 20-90% by weight, and the third ingredient can be in the range of 0-30% by weight.

Where a numerical limit is disclosed as a percentage of degree or measurement as a relation to another degree or measurement, it is to be understood as not limited to 0% or to 100%. For example, a container may have a height that is "at least 200% of its width" or an ingredient can be present in a concentration that is "greater than 120% of the concentration of" another ingredient.

Where numerical limits, ranges, or percentages are disclosed, the endpoint numbers are included. For example, "less than 10%" means and includes 10% or any amount less than 10% and means and includes 0% (none), except in cases where the endpoint would overlap with the endpoint of another numerical limit, range, or percentage, in which case the endpoint of "less than x %" means any percentage at least one hundredth of the unit less than the endpoint. For example, if one range is "10 to 30%" and another is "less than 10%," to avoid overlapping endpoints, then in this case the "less than 10%" means 9.99% or less.

Where a numerical limit of degree or measurement is disclosed with respect to a plurality or grouping of disclosed entities, the numerical limit of degree or measurement is also intended to be specifically disclosed regarding each entity of the plurality or grouping of disclosed entities collectively and independently. For example, if a numerical limit of "less than 10% of alcohols" is disclosed, it includes independent disclosure of "less than 10% of any alcohol," "less than 10% of methanol," "less than 10% of ethanol," "less than 10% of propanol," and less "than 10% of all alcohols." For another example, "less than 10% of alcohols" includes independent disclosure of "less than 10% of methanol," "less than 5% of methanol," "less than 4% of ethanol," "less than 1% of ethanol," "less than 6.5% of propanol," "less than 9% of menthol," and "0% (none) of sorbitol."

Physical Conditions, Properties, and Phases

"Absence" (noun) means the state of being absent or only present at a concentration below the sensitivity of a test.

"Amount" (noun) means a number or a quantity (as of a measurement, such as of a mass, weight, or concentration).

"Aqueous" (adjective) means relating to, similar to, containing, or dissolved in water.

"Concentration" (noun) means the amount of a specified substance in a unit amount of another substance.

"Decompose" (verb) means to break down or cause to break down into simpler compounds or elements, typically through chemical reactions such as hydrolysis or oxidation.

"Dissolve" (verb) means to cause to go into a solution. "Dissolution" is a kinetic process and is quantified by its rate. The solvated state is distinct from dissolution and solubility. Dissolution and solubility can be dependent on temperature and pressure, and may be dependent on other factors, such as salinity or pH of an aqueous phase.

"Liquid" (noun) means, depending on the context: (1) a substance that is liquid (adjective) at room temperature and pressure; (2) the state in which a substance exhibits a characteristic readiness to flow with little or no tendency to disperse and relatively high incompressibility (and not boiling, precipitating, or crystalizing); or (3) a substance in the fluid state of matter having no fixed shape but a fixed volume.

"Liquid" (adjective) regarding a substance means existing as or having characteristics of a liquid; especially tending to flow as a liquid.

"Material" (noun) means the tangible substance that goes into the makeup of a physical object, which can be constituted of one or more phases.

"Precipitate" (noun) means a solid or solid phase that has separated from a solution.

"Precipitate" (verb) means to separate as a solid substance from being dissolved in a solution.

"Room temperature" (noun phrase) means standard laboratory temperature.

"Solid" (noun) means the physical state of matter distinguished from liquid and gaseous by having a definite shape and volume. Unless otherwise stated, the state of a substance is determined under standard laboratory conditions.

"Solid" (adjective) regarding a substance means existing as or having characteristics of a solid; of definite shape and volume; not liquid or gaseous.

"Soluble" (adjective) means capable of being dissolved into a solvent as a solution. As used herein, a substance is considered to be "soluble" in a liquid if at least 10 grams of the substance can be hydrated or dissolved in one liter of the liquid when tested at 77° F. (25° F.) and 1 (one) atmosphere pressure, considered to be "insoluble" if less than 1 gram per liter, and considered to be "sparingly soluble" for intermediate solubility values.

"Solubility" (noun) means the quality or condition of being soluble. Solubility quantifies the concentration of the solute at which there is dynamic equilibrium between the rate of dissolution and the rate of precipitation of the solute. Dissolution and solubility can be dependent on temperature and pressure, and may be dependent on other factors, such as salinity or pH of an aqueous phase.

"Solution" (noun) means a homogeneous mixture of two or more substances; frequently (but not necessarily) a liquid solution. A solution is a special type of homogeneous mixture. A solution is considered homogeneous: (a) because the ratio of solute to solvent is the same throughout the solution; and (b) because the solute will never settle out of the solution (in a liquid state), even under powerful centrifugation, which is due to intermolecular attraction between the solvent and the solute. An aqueous solution, for example, saltwater, is a homogenous solution in which water is the solvent and salt is the solute.

"Solvated" or "dissolved" (verb) means a solute ion or molecule is associated with the solvent molecules by Intermolecular Forces. A chemical that is dissolved in solution is in a solvated state. The solvated state is distinct from dissolution and solubility.

"Solvent" (noun) means a substance, usually a liquid, capable of dissolving another substance or a substance in which another substance is dissolved.

"Standard Laboratory Conditions" (noun phrase) means at a temperature of 77° F. (25° C.), at a pressure of 1 (one) atmosphere (101.325 kPa or 760 mmHg), without applied shear (e.g., any mixing force), and ambient relative humidity in the range of 40-60%.

"Standard laboratory pressure" or "standard pressure" or "normal pressure" (noun phrase) means 1 (one) atmosphere (101,325 Pascal).

"Standard laboratory temperature" or "normal temperature" (noun phrase) means at a temperature of 77° F. (25° C.).

"State" (noun) means a condition or mode of being, as with regard to circumstances. In chemistry and physics, it means the condition of a physical system with regard to phase, form, composition, or structure. The common physical states of matter include solid, liquid, and gas. The physical state of a substance depends on temperature and pressure. If not other otherwise specifically stated, the physical state or phase or condition of a substance (or mixture of substances) and other physical properties are determined under Standard Laboratory Conditions.

"Suspension" (noun) means a dispersion in which minute particles are dispersed throughout a fluid from which they are easily filtered but not rapidly settling because of viscosity or molecular interactions.

"Weight" (noun) means a measure of the heaviness of an object, and more particularly, the force with which a body is attracted to Earth or another celestial body, equal to the product of the object's mass and the acceleration of gravity. In the context of earth's gravitational constant, the weight of an object may be loosely equated to the mass of the object. For example, 2.2 pounds weight is equivalent to 1 kg mass, and grams or kilograms can be referred to as weights.

Chemical Terminology

"Acid" (noun) means: (a) any of a class of substances whose aqueous solutions are characterized by a sour taste, the ability to turn blue litmus red, and the ability to react with bases and certain metals to form salts; or (b) an aqueous solution of an acid.

"Acidic" (adjective) means of, relating to, or containing an acid or having the characteristics of an acid.

"Alkali" (noun) means a base that dissolves in water.

"Anion" (noun) means a negatively charged ion having fewer electrons than protons.

In chemistry, "base" (noun) means: (a) any of a class of substances whose aqueous solutions are characterized by a bitter taste, feeling slippery to touching with the fingers, the ability to turn red litmus blue, and the ability to react with acids to form salts; or (b) an aqueous solution of a base.

In chemistry, "basic" (adjective) means of, relating to, or containing a base or having the characteristics of a base.

"Bicarbonate" (more formally known as "hydrogen carbonate") means the anion $HCO_3^-$, which has a single negative charge.

"Cation" (noun) means a positively charged ion having more electrons than protons.

"Carbonate" (noun) means the anion $CO_3^-$, which has a double negative charge.

"Chemical" (adjective) means of or relating to chemistry or means of or relating to the properties or actions of chemicals, depending on the context. "Chemically" (adverb) means of or relating to chemistry or means of or relating to the properties or actions of chemicals, depending on the context.

"Chemical agent" or "chemical reagent" (noun phrase) means a chemical that is capable of a desired chemical reaction in the relevant context.

"Chemical source of" (noun phrase) means a compound, substance, or material that provides or releases a specified chemical element, ion, or moiety through dissolution, decomposition, or reaction in a relevant context, such as in a dietary composition or physiological environment.

"Compound" (noun) in chemistry means an entity consisting of two or more atoms, at least two from different chemical elements, that associate via one or more chemical bonds, such as ionic or covalent bonds.

"Group" (noun) means a number of individuals or things considered or classed together based on one or more similarities. In chemistry, depending on the context, "group" means two or more atoms behaving or regarded as behaving as a single chemical unit or it means a column in the periodic table of the elements.

"Inorganic" (adjective) means not organic. See definition of "organic" herein.

"Inorganic salt" (noun phrase) means a salt that comprises at least an inorganic cation or anion.

"M" is an abbreviation for molar.

"Molar" (adjective) means a unit of concentration expressing the number of moles of a solute per liter of solution; as an adjective, relating to or denoting such a concentration or to quantities based on moles.

"Mole" (noun), which is sometimes abbreviated to "mol", means Avogadro's number, i.e., $6.022\times10^{23}$. (Because atoms, molecules, or moieties or functional groups of molecules are microscopic, an extremely large number is required to reach an amount that would be observable on the human scale of perception.)

"Molecule" (noun) means a group of atoms bonded together, representing the smallest fundamental unit of a chemical compound. While for some purposes a "molecule" is more narrowly defined as a group of atoms having one or more covalent bonds, for the purposes of this disclosure, an ionic salt of an organic compound, such as sodium acetyl salicylate, is still considered a "molecule."

"Organic" (adjective) means having at least one carbon atom in a molecule, excluding allotropes of carbon (e.g., graphite, diamond, graphene, and fullerenes), carbides, inorganic carbonates (e.g., carbon dioxide, carbonic acid, and calcium carbonate), and inorganic cyanides, where "inorganic cyanide" means a chemical having a CN group but not any other carbon atom. An organic compound may contain other elements (especially H, O, N, S, or one or more halogens.

"pH" (noun), denoting "potential of hydrogen" or "power of hydrogen," is a scale of the acidity or basicity of an aqueous solution. At room temperature, pure water is neutral (neither acidic nor basic) and has a pH of 7. pH values less than 7 correspond to solutions which are more acidic in nature, while pH values greater than 7 correspond to solutions which are more basic or alkaline.

"Salt" (noun) means ionic compounds that result from the neutralization reaction of an acid and a base. A salt is composed of one or more cations (positively charged ions) and one or more anions (negative ions) so that the salt is electrically neutral (without a net charge). Salts include those derived from inorganic or organic acids and bases.

"Stoichiometry" (noun) means the calculation of the relative quantities of reactants and products in chemical reactions, based on the balanced equation and molar ratios.

"Strong" (adjective) in regard to an acid or a base means an acid or a base that completely dissociates in water. For example, the hydroxides of the Group I (alkali metals) and Group II (alkaline earth) metals are considered to be strong bases. The oxides of the Group I and Group II elements react with water to form the hydroxides in aqueous solution, so these can also be considered strong bases. In contrast, "weak" in regard to an acid or base means an acid or base that does not completely dissociate in water. For example, carbonates and bicarbonates are considered to be weak bases.

"Sugar" (noun) means the sweet-tasting, soluble carbohydrates, many of which are used in food, and in some contexts may particularly mean sucrose.

Animal Physiology and Feed

"Animal" (noun) means an animal organism other than a human.

"Animal feed" (noun phrase) or "feed" means a food given to livestock in the course of animal husbandry.

"Basal diet" (noun phrase) means the primary feed ration for an animal, consisting of core ingredients like forages, grains, and proteins, excluding targeted supplements or additives intended to modify specific nutritional parameters such as mineral balance.

"Body" (noun) in pharmacology means the entire material or physical structure of an organism, especially of a human or animal.

"Bulk feed" (noun phrase) means the bulk of an animal feed not including supplements or added ingredients or prior to adding supplements or added ingredients.

"Forage" (noun) means (1) plant material that livestock graze or that is cut and fed to them; or (2) the act of looking or searching for food or provisions.

"Mammal" (noun) means any of various warm-blooded vertebrate animals of the class Mammalia, including humans, characterized by a covering of hair on the skin and, in the female, milk-producing mammary glands for nourishing the young.

"Normal" (adjective) means functioning or occurring in a natural way; lacking observable abnormalities or deficiencies. "Abnormal" (adjective) means not normal.

"System" (noun) in biology means an organism as a whole, especially with regard to its vital processes or functions or means a group of physiologically or anatomically related organs or parts, e.g., the circulatory system, depending on the context.

"Systemic" (adjective) in biology or medicine means relating to or affecting the entire body or an entire organism.

More Specific Terminology

"Al" is an abbreviation for the chemical element aluminum.

"Al(III)" is an abbreviation for the chemical element aluminum in the +3 chemical oxidation state.

"Al(II) compound" (noun phrase) means a chemical compound in which aluminum is present in the +3 oxidation state, such as salts, oxides, hydroxides, or complexes capable of releasing Al{3+} ions in relevant contexts like dissolution or physiological environments.

"Al-DCAD" (noun phrase) is an abbreviation for an aluminum-DCAD composition according to an embodiment of the present disclosure.

"AP" is an abbreviation for adequate dietary phosphorus.

"Avg Anionic" means the average of the data when the cows are eating a TDC including the "Liquid Anionic" product.

"BAL" is an abbreviation for Bronchoalveolar Lavage.

"Blood phosphorus" or "blood P" or "serum P" means the concentration of P in the serum of the blood. Note that blood phosphorus as measured in clinical settings, it refers to inorganic phosphate ($PO_4^{3-}$ or its protonated forms, such as $HPO_4^{2-}$ and $H_2PO_4^-$) rather than elemental phosphorus. Phosphorus in the blood exists primarily as phosphate groups.

"Bronchoalveolar lavage" means a diagnostic procedure where saline is instilled into the lungs (via bronchoscope or catheter) and then aspirated to collect fluid from the alveoli and small airways. The retrieved BAL fluid is analyzed for cells, proteins, or pathogens to assess lung health, inflammation, or infection.

"Ca" is an abbreviation for the chemical element calcium.

"Cl" is an abbreviation for the chemical element chlorine.

"Closeup" (adjective phrase) means the 3-4 weeks prepartum.

"Crude protein" (noun phrase) means the estimated total protein content in a feed or diet, calculated by multiplying the nitrogen content by a factor (typically 6.25), including both true proteins and non-protein nitrogen sources.

"CU" is an abbreviation for "closeup."

"Cytokines" means small signaling proteins secreted by various cells, primarily immune cells, that regulate immune responses, inflammation, and other physiological processes. They act as chemical messengers, facilitating communication between cells to coordinate immune and inflammatory responses.

"Dairy cows" (noun phrase) means female bovine animals (*Bos taurus* or similar species) bred and managed primarily for milk production, including those in prepartum, peripartum, or postpartum stages.

"Days in milk" (adjective phrase) means the number of days that have elapsed since a cow last calved and began her current lactation period, serving as a key metric for tracking lactation stage, reproductive performance, and overall herd management.

"DCAD" is an abbreviation for dietary cation-anion difference.

"Died and sold cows" (noun phrase) means cows that died or were culled from the herd in the first 60 days in milk.

"Dietary cation-anion difference" is a measure of the acid-base balance in an animal's diet, calculated as the difference between positively charged cations (e.g., sodium [$Na^+$] and potassium [$K^+$]) and negatively charged anions (e.g., chloride [$Cl^-$] and sulfur [$S^{2-}$]) in a composition, expressed in milliequivalents per 100 grams (mEq/100 g) on a dry matter basis. The formula is DCAD=([Na]+[K])—([Cl]+[S]).

"DIM" is an abbreviation for "days in milk," which means the day or days postpartum.

"DM" is an abbreviation for "dry matter."

"Dry cow ration" (noun phrase) means a specialized diet formulated for dairy cows during their dry period, the phase when they are not lactating, typically lasting 6-8 weeks before calving. This period allows the cow's udder to rest and prepare for the next lactation cycle.

"Dry matter" (noun phrase) means the portion of a feed, ration, or sample that remains after all water (moisture) has been removed. It represents the total weight of the feed's nutrients—such as proteins, carbohydrates, fats, minerals, and fiber-expressed as a percentage of the original weight. Dry matter is typically determined by oven drying or lyophilization methods.

"Dry matter basis" (noun phrase) means the method of expressing the nutrient content, concentrations, or proportions in a feed, diet, or sample after removing or accounting for the moisture (water) content, calculated as a percentage or ratio relative to the total dry matter weight.

"Dry Phos Binder" (noun phrase) means a previously commercially available products comprising sodium aluminum silicates (aka zeolites), which are insoluble in weak acid.

"Fe" is an abbreviation for the chemical element iron.

"Fe(III)" is an abbreviation for the chemical element iron in the +3 chemical oxidation state.

"Feed" (noun) means any substance or mixture provided to animals for consumption to supply nutrients, energy, or other dietary needs, including forages, concentrates, and supplements.

"Feeding" (verb) means the act of providing or administering feed to animals, typically on a consistent basis to meet nutritional requirements and achieve desired physiological outcomes.

"Ferric" means the chemical element iron in the +3 chemical oxidation state.

"FGF23" is an abbreviation for the hormone Fibroblast Growth Factor 23.

"Fibroblast Growth Factor 23" (noun phrase) is a hormone primarily produced by osteocytes and osteoblasts in bone tissue. It plays a critical role in regulating phosphate and vitamin D metabolism, which are essential for bone health and mineral homeostasis. In animal studies, particularly those involving parathyroid hormone (PTH), multiparous animals, or dry cow rations, FGF23 is often investigated for its interactions with PTH and its impact on calcium and phosphate balance.

"Fresh Cows" (noun phrase) means cows that have recently calved (given birth) and entered the early stages of lactation, typically encompassing the first 1 to 30 days in milk (DIM) postpartum. This period is critical as cows transition from the dry (non-lactating) phase to peak milk production, during which they are more vulnerable to health issues like metabolic disorders, infections, or reduced feed intake, requiring specialized management, monitoring, and nutrition.

"HCl" is an abbreviation for the chemical hydrochloric acid.

"Hypocalcemia" (noun) means blood calcium typically <5.5 mg/dL (<1.4 mmol/L) in serum or plasma or a cow showing clinical symptoms of recumbency, compromised neuromuscular or circulatory function.

"Iron(III) compound" (noun phrase) means a chemical substance containing iron atoms or ions, such as salts or complexes, capable of providing iron(III) for functions like phosphorus binding in dietary or physiological contexts.

"Incidence" (noun phrase) means the rate or frequency of occurrence of a specific event, condition, or disease within a defined population over a given period.

"L" is an abbreviation for liter.

"Lactation" (noun) means the physiological process in female mammals of producing and secreting milk from mammary glands, typically following parturition.

"Liquid Anionic" (noun phrase) means a previously commercially available product comprising magnesium chloride, ammonium chloride, hydrochloric acid, and water [no need to mention other ingredients xanthan gum and caramel flavor].

"LP" is an abbreviation for low, inadequate dietary phosphorus, that is, less than about 0.16% P in dry matter, by weight.

"LPS" means a lipopolysaccharide, specifically here a component of the outer membrane of Gram-negative bacteria, such as *Escherichia coli*. It is an endotoxin that triggers strong immune responses in animals by activating inflammatory pathways.

"LPS injection(s)" means injecting LPS (a bacterial endotoxin from Gram-negative bacteria) into animals (e.g., intravenously, intraperitoneally, or intratracheally) to mimic bacterial infection, trigger systemic inflammation, or study immune-metabolic interactions. Doses are typically low (e.g., 0.1-5 μg/kg body weight) to avoid lethality while eliciting measurable responses.

"Maintains" (verb) means to keep or sustain at a desired level, range, or condition, such as a physiological parameter, without significant deviation."

"Mast" is an abbreviation for "mastitis."

"Mastitis" (noun) means inflammation of the mammary gland in animals, often caused by bacterial infection, leading to reduced milk quality and yield."

"MF" is an abbreviation for "milk fever."

"Milk fever" (noun phrase) means, also known as parturient paresis or hypocalcemia, is a condition in dairy cows where blood calcium levels drop dangerously low (typically <5.5 mg/dL or <1.4 mmol/L in serum) due to the sudden demand for calcium to produce colostrum and milk post-calving. This can lead to muscle weakness, recumbency, and potentially life-threatening complications if untreated. It is most common in multiparous cows (those that have calved multiple times) due to their higher milk production and greater calcium demand compared to primiparous cows. (Subclinical hypocalcemia thresholds in multiparous cows as serum Ca below 7.1 mg/dL on DIM=1 and 8.82 mg/dL on DIM 4.)

"Molar binding capacity" (noun phrase) means the maximum amount of a substance (e.g., phosphorus) that can be bound per mole of a binding agent, based on stoichiometric interactions under relevant conditions.

"Multiparous" means an animal that has given birth multiple times. It describes individuals that have experienced more than one pregnancy and delivery, as opposed to primiparous (having given birth once) or nulliparous (never having given birth).

"Na" is an abbreviation for the chemical element sodium.

"Non-protein nitrogen" (noun phrase) means a class of nitrogenous compounds, such as urea, ammonia, biuret, or ammonium salts, that are not true proteins but can be metabolized by rumen microorganisms in dairy cattle to produce microbial protein, serving as a cost-effective nitrogen source in ruminant diets.

"Non-toxic" (adjective phrase) means materials, such as feed ingredients, additives, or environmental factors, that are safe and do not produce toxic effects, physiological harm, or detrimental health impacts in dairy animals or their products under normal conditions of use, as determined by scientific evaluation or regulatory standards.

"NPN" is an abbreviation for non-protein nitrogen.

"NRC" is an abbreviation for National Research Council, an organization that provides guidelines on nutrient requirements for animals, including dairy cattle.

"P" is an abbreviation for the chemical element phosphorus.

"Parous" means having given birth at least or more than once. In the context of the data presented, parous is used to describe cows in the closeup dry period prior to their second or greater birth event (after which they enter the "multiparous" description).

"Phosphorus binding element" means a chemical element or ion, such as aluminum(III) or iron(III), capable of forming complexes or precipitates with phosphorus compounds to reduce their bioavailability in a dietary or physiological context.

"Phosphorus-to-aluminum weight ratio" means the ratio of the total weight of phosphorus to the weight of supplemental aluminum in a composition, sometimes expressed as P:(Suppl. Al), calculated on a dry matter basis.

"Phosphorus-to-(aluminum times calcium) weight ratio" means the ratio of the total weight of phosphorus to the product of the weights of supplemental aluminum and total weight of calcium in a composition, sometimes expressed as P:(Suppl. Al×Ca), calculated on a dry matter basis.

"Plasma" means the liquid portion of blood obtained when clotting is prevented using an anticoagulant. It is separated by centrifuging blood immediately after collection to isolate the liquid from blood cells.

"Postpartum" (adjective) means the period immediately following calving (parturition), during which the cow undergoes physiological recovery, including uterine involution, metabolic adjustments, and resumption of ovarian cyclicity, typically spanning from birth up to 45-60 days or until fertile estrus resume.

"ppm" is an abbreviation for parts per million, a unit of concentration expressing the number of parts of a substance per million parts of the total mixture, often by weight.

"Prepartum" (adjective) means the period immediately preceding calving (parturition), typically encompassing the final 3 to 4 weeks of gestation (often from dry-off until birth), during which cows undergo physiological changes, nutritional adjustments, and increased management to mitigate risks like metabolic stress and prepare for the transition to lactation.

"PTH" is an abbreviation for parathyroid hormone.

"Ration" is an abbreviation for total mixed ration.

"S" is an abbreviation for the chemical element sulfur.

"Serum" means the liquid portion of blood remaining after it has clotted. It is obtained by allowing blood to clot naturally, then centrifuging to separate the liquid from the clot (which contains red blood cells, white blood cells, and clotting factors).

"Sham" means a control procedure used in experimental designs to mimic the intervention or treatment without delivering the active component. It is used to isolate the effects of the experimental treatment from the effects of the procedure itself.

"SID" is an abbreviation for strong ion difference.

"Stoichiometric ratio" (noun phrase) means the proportion of reactants or components in a chemical reaction or binding interaction, as determined by the balanced equation or molar equivalences.

"Strong ion difference" means a quantitative measure of acid-base balance in serum (the liquid portion of blood without clotting factors), based on the Stewart physicochemical approach to acid-base physiology. It represents the net difference between the concentrations of strong cations (positively charged ions) and strong anions (negatively charged ions) that are fully dissociated in solution and do not participate in acid-base reactions. Basic Formula: $SID=([Na^+]+[K^+])—[Cl^-])$, often expressed in mEq/L or mmol/L. This is sometimes denoted as "$SID_3$" or simply "SID" (for the three primary ions: sodium, potassium, and chloride).

"Subclinical hypocalcemia" is a decrease in serum Ca concentration around parturition without clinical disease.

"Supplement" (noun) means an additive to a basal diet intended to provide specific nutrients, minerals, or functional ingredients to enhance nutritional balance or achieve targeted physiological effects.

"Supplemental" (adjective) means provided as an addition to a primary or basal component, such as a diet, to supply deficiencies or enhance effects.

"Target range" (noun phrase) means the optimal or desired range of values for a specific dietary, nutritional, or physiological parameter in dairy cows (particularly during the prepartum or periparturient period) that is associated with improved calcium homeostasis, reduced risk of hypocalcemia (clinical or subclinical), and enhanced overall health and performance outcomes.

"TDC" is an abbreviation for total dietary composition.

"TMR" is an abbreviation for total mixed ration.

"Total dietary aluminum" (noun phrase) means the aggregate concentration or amount of aluminum in the complete diet provided to an animal, including contributions from the basal diet, supplements, and any other dietary components, typically measured on a dry matter basis.

"Total dietary calcium" (noun phrase) means the aggregate concentration or amount of calcium in the complete diet provided to an animal, including contributions from the basal diet, supplements, and any other dietary components, typically measured on a dry matter basis.

"Total dietary composition" (noun phrase) means the total composition of the diet, including all dietary components—such as forages (e.g., hay, silage), grains, protein supplements, minerals, and additives (e.g., NPN sources like urea). A TDC can be fed as a total mixed ration (TMR).

"Total dietary iron" (noun phrase) means the aggregate concentration or amount of biologically available iron in the complete diet provided to an animal, including contributions from the basal diet, supplements, and any other dietary components, typically measured on a dry matter basis.

"Total dietary phosphorus" (noun phrase) means the aggregate concentration or amount of phosphorus in the complete diet provided to an animal, including contributions from the basal diet, supplements, and any other dietary components, typically measured on a dry matter basis.

"Total dietary sulfur" (noun phrase) means the aggregate concentration or amount of sulfur in the complete diet provided to an animal, including contributions from the basal diet, supplements, and any other dietary components, typically measured on a dry matter basis.

"Total mixed ration" means a feeding system used in dairy and beef cattle management where all dietary components—such as forages (e.g., hay, silage), grains, protein supplements, minerals, and additives (e.g., NPN sources like urea)—are blended into a single, uniform mix. This ensures that each bite provides a balanced intake of nutrients, including energy, protein, fiber, and minerals.

"Transition success" means the success of going from a cow that is dry and pregnant to a cow that is production milk at the beginning of her lactation, where success is defined as having the miming amount of disease incidence and maximum rate off survival.

"Zeolite" means a microporous aluminosilicate mineral, natural or synthetic, capable of ion exchange and adsorption, often used in feed as a binder for minerals or toxins in feed. Zeolites include aluminosilicates such as clinoptilolite or synthetic Zeolite A.

CONCLUSION

Therefore, the disclosure can be understood by a person of skill in the art to obtain the purposes and advantages mentioned as well as those that are inherent therein.

The various disclosed embodiments are illustrative only, as the disclosure can be modified and practiced in different but equivalent manners apparent to those skilled in the art having the benefit of the teachings herein. It is, therefore, evident that the particular illustrative embodiments disclosed above can be altered or modified and all such variations are considered within the scope of the disclosure.

The various elements or steps according to the disclosed elements or steps can be combined advantageously or practiced together in various combinations or subcombinations of elements or sequences of steps to increase the efficiency and benefits that can be obtained from the disclosure.

It should be understood that one or more of the above and various embodiments can be combined with one or more of the other various embodiments, unless explicitly stated otherwise.

The illustrative disclosure can be practiced in the absence of any element or step that is not specifically disclosed or claimed.

Any particular embodiment of the disclosure that falls within the prior art can be explicitly excluded from any one or more of the claims. Because such embodiments are deemed to be known to one of ordinary skill in the art, they can be excluded even if the exclusion is not set forth explicitly herein.

Any particular embodiment of the disclosure can be explicitly excluded from a particular patent claim, for any reason, whether or not related to the existence of prior art. Where elements are presented as lists, for example, in Markush group format, each subgroup of the elements is also disclosed, and any element or elements can be removed from the claimed group.

Those of ordinary skill in the art will recognize or be able to ascertain using no more than routine experimentation many equivalents to the specific embodiments of this disclosure. Those of ordinary skill in the art will appreciate that various changes and modifications to this description can be made without departing from the spirit or scope of the disclosure.

The description of the specific examples herein does not necessarily point out what an infringement would be but are to provide at least one explanation of how to make and use the disclosure.

Furthermore, no limitations are intended to the details of composition, design, construction, or steps of the disclosure, other than as set forth in a specific claim.

What is claimed is:

1. A total dietary composition (TDC) for dairy cows, the TDC comprising:

(A) a basal diet; and (B) a supplemental source of one or more phosphorus-binding elements comprising one or more chemical sources of aluminum(III);

wherein the TDC has:

(i) a phosphorus-to-(aluminum times calcium) weight ratio of 1.8:1 to 4.0:1 based on total dietary phosphorus, aluminum from the one or more chemical sources of aluminum(III), and total dietary calcium, measured on a dry matter basis; and (ii) a Dietary Cation-Anion Difference (DCAD) of −15 to +10 mEq/100 g dry matter calculated as ([Na]+[K])—[Cl]+[S]).

2. The TDC of claim 1, wherein the TDC has a phosphorus-to-(aluminum times calcium) weight ratio of 1.8:1 to 3.0:1 based on total dietary phosphorus, aluminum from the one or more chemical sources of aluminum(III), and total dietary calcium, measured on a dry matter basis.

3. The TDC of claim 1, wherein at least one chemical source of aluminum(III) has a characteristic of dissolving or decomposing in 0.1 M HCl to at least 1 mole of Al/L as determined without stirring after 2 hours at 20° C.

4. The TDC of claim 1, wherein at least 50% of the aluminum from the chemical sources of aluminum(III) is from one or more chemical sources of aluminum(III) having a characteristic of dissolving or decomposing in 0.1 M HCl to at least 1 mole of Al/L as determined without stirring after 2 hours at 20° C.

5. The TDC of claim 1, wherein at least 90% of the aluminum from the chemical sources of aluminum(III) is from one or more chemical sources of aluminum(III) having a characteristic of dissolving or decomposing in 0.1 M HCl to at least 1 mole of Al/L as determined without stirring after 2 hours at 20° C.

6. The TDC of claim 1, wherein the one or more chemical sources of aluminum(III) comprise aluminum(III) compounds selected from the group consisting of aluminum sulfate, aluminum chloride, aluminum carbonate, aluminum hydroxide, and any combination thereof.

7. The TDC of claim 1, wherein the chemical sources of aluminum(III) are at concentrations non-toxic to dairy cows, as determined by NRC guidelines.

8. The TDC of claim 1, wherein the supplemental source of phosphorus-binding elements comprises one or more chemical sources of iron (II), iron(III), and any combination thereof.

9. The TDC of claim 8, wherein the concentration of iron(III) from the supplemental source of phosphorus-binding elements in the TDC is at most 250 ppm on a dry matter basis.

10. The TDC of claim 1, wherein the total iron(II) and iron(III) concentration in the TDC is up to 1,000 ppm on a dry matter basis.

11. The TDC of claim 1, wherein the TDC has a DCAD of −15 to 0 mEq/100 dry matter calculated as ([Na]+[K])—[Cl]+[S]).

12. The TDC of claim 1, wherein the TDC comprises one or more ingredients selected from the group consisting of: non-protein nitrogen; cane molasses; condensed molasses solubles; a clay; and water.

13. The TDC of claim 12, wherein the non-protein nitrogen is selected from the group consisting of urea, ammonium sulfate, ammonium chloride, biuret [($C_2H_5N_3O_2$)], and ammonium bicarbonate, and any combination thereof.

14. The TDC of claim 1, wherein the TDC comprises:

(a) a basal diet; and (b) a supplement for the basal diet, wherein the supplement comprises at least a portion of the chemical sources of aluminum(III).

15. The TDC of claim 14, wherein the supplement is in the form of a liquid or a liquid suspension.

16. The TDC of claim 1, wherein, with feeding of the TDC to closeup dairy cows, the TDC maintains the serum phosphorus of the dairy cows in a range of 3.6 to 4.6 mg/dL.

17. The TDC of claim 1, wherein, with feeding of the TDC for closeup dairy cows, the TDC reduces the incidence of milk fever in multiparous cows by at least 30% relative to without the one or more phosphorus-binding elements.

18. A method of feeding prepartum dairy cows, the method comprising a step of feeding the cows the TDC of claim 1.

19. The method of claim 18, comprising a step of measuring one or more of effects selected from the group consisting of:

(a) serum P;

(b) serum Ca;

(c) milk fever incidence, (d) mastitis incidence;

(e) died and sold cows;

(f) milk yield in first 4 weeks of lactation; and (g) any combination thereof.

20. A dietary supplement composition for dairy cows, comprising: one or more chemical sources of aluminum(III) configured to bind phosphorus in a dairy cow diet, wherein the supplement is formulated to contribute to a total dietary composition having:

(a) a phosphorus-to-(aluminum times calcium) weight ratio of 1.8:1 to 4.0:1 based on total dietary phosphorus, aluminum from the one or more chemical sources of aluminum(III), and total dietary calcium, measured on a dry matter basis; and (b) a Dietary Cation-Anion Difference (DCAD) of −15 to +10 mEq/100 g dry matter calculated as ([Na]+[K])—[Cl]+[S]).

* * * * *